US012227778B2

(12) United States Patent
Koglin et al.

(10) Patent No.: US 12,227,778 B2
(45) **Date of Patent: *Feb. 18, 2025**

(54) CELL-FREE EXPRESSION SYSTEM HAVING NOVEL INORGANIC POLYPHOSPHATE-BASED ENERGY REGENERATION

(71) Applicant: NTxBio, LLC, Santa Fe, NM (US)

(72) Inventors: Alexander Koglin, Santa Fe, NM (US); Michael Humbert, Santa Fe, NM (US)

(73) Assignee: NATURE'S TOOLBOX, INC., Rio Rancho, NM (US)

(*) Notice: Subject to any disclaimer, the term of this patent is extended or adjusted under 35 U.S.C. 154(b) by 780 days.

This patent is subject to a terminal disclaimer.

(21) Appl. No.: 17/039,575

(22) Filed: Sep. 30, 2020

(65) Prior Publication Data

US 2021/0024912 A1 Jan. 28, 2021

Related U.S. Application Data

(63) Continuation-in-part of application No. 16/309,074, filed as application No. PCT/US2018/012121 on Jan. 2, 2018, now Pat. No. 11,136,586.

(60) Provisional application No. 62/440,975, filed on Dec. 30, 2016.

(51) Int. Cl.

| | |
|---|---|
| ***C12N 9/52*** | (2006.01) |
| ***C12N 9/04*** | (2006.01) |
| ***C12N 9/12*** | (2006.01) |

(52) U.S. Cl.

CPC ............. *C12N 9/52* (2013.01); *C12N 9/0006* (2013.01); *C12N 9/1205* (2013.01); *C12N 9/1229* (2013.01); *C12N 9/1247* (2013.01); *C12Y 101/01014* (2013.01); *C12Y 207/0102* (2013.01); *C12Y 207/04001* (2013.01); *C12Y 207/07006* (2013.01); *C12Y 304/24068* (2013.01)

(58) Field of Classification Search

None

See application file for complete search history.

(56) References Cited

U.S. PATENT DOCUMENTS

| | | | | |
|---|---|---|---|---|
| 5,830,694 | A | 11/1998 | Studier | |
| 8,101,732 | B2 | 1/2012 | Mahmud | |
| 2005/0032086 | A1 | 2/2005 | Sakanyan et al. | |
| 2009/0209032 | A1* | 8/2009 | Kudlicki ................ | C12N 15/70 435/320.1 |
| 2010/0042375 | A1 | 2/2010 | Philips, Jr. et al. | |
| 2014/0328801 | A1 | 11/2014 | Prentice et al. | |
| 2015/0140603 | A1 | 5/2015 | Gerrits et al. | |
| 2016/0028101 | A1 | 1/2016 | Zhang et al. | |
| 2017/0058056 | A1 | 3/2017 | Mattoussi et al. | |
| 2017/0292138 | A1 | 10/2017 | Blake | |

FOREIGN PATENT DOCUMENTS

| | | | |
|---|---|---|---|
| CN | 105861598 | A * | 8/2016 |
| EP | 1652934 | A1 | 5/2006 |
| EP | 1842910 | A1 | 10/2007 |
| JP | 2013-66446 | A | 4/2013 |
| JP | 2016-518833 | A | 6/2016 |
| WO | 1998030591 | A1 | 7/1998 |
| WO | 1998/048031 | A1 | 10/1998 |
| WO | 2004081033 | A2 | 9/2004 |
| WO | 2005/045005 | A1 | 5/2005 |
| WO | 2006109751 | A1 | 10/2006 |
| WO | 2012038950 | A1 | 3/2012 |
| WO | 2016/160936 | A1 | 10/2016 |
| WO | 2017176963 | A1 | 10/2017 |

OTHER PUBLICATIONS

Shimizu, Y., Inoue, A., Tomari, Y. et al. Cell-free translation reconstituted with purified components. Nat Biotechnol 19, 751-755. (Year: 2001).*

Roche. Safety Data Sheet. tRNA, from *E.coli* MRE 600; Version 1.8; first published Oct. 20, 2015. (Year: 2015).*

Notification of Substantive Examination Stage I Result from Ministry of Law and Human Rights of the Republic of Indonesia Directorate General of Intellectual Property in Patent Application No. P00201905488 mailed on Nov. 17, 2020.

Office Action issued by JPO in application No. 2019-534965 mailed on Oct. 13, 2020.

Shin J. et al. , Journal of Biological Engineering, 4:8 (2010)—"Efficient cell-free expression with hen endogenous *E.coli* rna Polymerase and Sigma Factor 70".

Carlson, Erik D. et al. "Cell-Free Protein Synthesis: Applications Come of Age" Biotechnology advances 30.5 (2012): 1185-1194. PMC. Web Jan. 1, 2018.

Shih et al., Self-cleavage of fusion protein in vivo using TEV protease to yield native protein, 2005, Protein Science, vol. 14, 936-941. (Year: 2005).

Karig et al., Expression optimization and synthetic gene networks in cell-free systems, 2011, Nucleic Acids Research, vol. 40, 3763-3774, (Year: 2011).

EP Substantive Examination Report dated Mar. 18, 2021 in EP Application No. 18734006.2, 5 pages.

International Search Report and Written Opinion dated Apr. 26, 2018 in International Application No. PCT/US18/12121 filed Jan. 2, 2018.

(Continued)

*Primary Examiner* — Neil P Hammell
*Assistant Examiner* — Khaleda B Hasan
(74) *Attorney, Agent, or Firm* — Berg Hill Greenleaf Ruscitti LLP

(57) ABSTRACT

The invention relates to an in vitro cell-free expression system incorporating a novel inorganic polyphosphate-based energy regeneration system. In certain embodiments, the invention includes a cell-free expression system where the cellular energy source, ATP, is regenerated from inorganic polyphosphate using a dual enzyme system. In this embodiment, this dual enzyme system may include thermostable Adenosyl Kinase, and/or Polyphosphate Kinase enzymes.

30 Claims, 16 Drawing Sheets

Specification includes a Sequence Listing.

(56) References Cited

OTHER PUBLICATIONS

Calhoun, et al., "Energy Systems for ATP Regeneration in Cell-Free Protein Synthesis Reactions", In Vitro Transcription and Translation Protocols, Methods in Molecular Biology, 2007, Chapter 1, pp. 3-17, vol. 375, Second Edition, Grandi, Humana Press Inc., Totowa, NJ.
Minakhin, et al., "Recombinant Thermus aquaticus RNA Polymerase, a New Tool for Structure-Based Analysis of Transcription", Journal of Bacteriology, Jan. 2001, pp. 71-76, vol. 183, No. 1, American Society for Microbiology.
Restiawaty, et al., "Reasibility of thermophilic adenosine triphosphate-regeneration system using Thermus hermophilus polyphosphate kinase", Process Biochemistry, May 20, 2011, pp. 1747-1752, vol. 46, Elsevier Lid.
Cao, et al., "Sorbitol Can Fuel Mouse Sperm Motility and Protein Tyrosine Phosphorylation via Sorbitol Dehydrogenase", Biology of Reproduction, Sep. 17, 2008, pp. 124-133, vol. 80, the Society for the Study of Reproduction, Inc.
NCBI, adenylate kinase [Geobacillus stearothermophilus], downloaded from the internet https://www.ncbi.nlm.nih.gov/protein/WP _053414240 on Dec. 11, 2018; one page.
Counago, et al., "Gene replacement of adenylate kinase in the gram-positive thermophile Geobacillus , tearothermophilus disrupts adenine nucleotide homeostasis and reduces cell viability", Extremophiles, Jan. 13, 2005, pp. 135-144, vol. 9, Springer-Verlag.
NCBI, polyphosphate kinase [Thermus aquaticus], downloaded from the internet https://www.ncbi.nlm.nih.gov/protein/NP_053768191 on Dec. 11, 2018; pp. 1-2.
Kinfu, et al., "Recombinant RNA Polymerase from *Geobacillus* sp. GHH01 as tool for rapid generation of metagenomic RNAs using in vitro technologies", Biotechnology and Bioengineering, Aug. 21, 2017, pp. J739-J2752, vol. 114, Wiley Periodicals, Inc.
Yousefi et al., Avicenna Joernal of Medical Biotechn., 5, 4, 220-226 (Year: 2013).
EP Search Report dated May 15, 2020 in EP Application No. 18 73 4006, 8 pages.

* cited by examiner

| Sequence ID | RNAP subunit | Additional aa native protein sequence | |
|---|---|---|---|
| SEQ ID. NO: 1 | alpha | GS | |
| SEQ ID. NO: 2 | beta | GS | |
| SEQ ID. NO: 4 | beta'(opt) | GSAHHHHHH | SEQ ID NO. 24 |
| SEQ ID. NO: 5 | delta | GS | |
| SEQ ID. NO: 6 | omega | GS | |
| **Sequence ID** | **Transcription factor** | **Additional aa protein sequence** | |
| SEQ ID. NO: 7 | RpoD | M-His6-V5-TEV | |

Fig. 3

SEQ ID NO. 10

SEQ ID NO. 25

CELL-FREE EXPRESSION SYSTEM HAVING NOVEL INORGANIC POLYPHOSPHATE-BASED ENERGY REGENERATION

The application is a continuation-in-part of U.S. application Ser. No. 16/309,074, filed Dec. 11, 2018, which claims the benefit of and priority to International Application No. PCT/US18/12121, filed Jan. 2, 2018; which claims the benefit of and priority to U.S. Provisional Patent Application No. 62/440,975, filed Dec. 30, 2016, all of which are incorporated herein by reference.

SEQUENCE LISTING

The instant application contains a Sequence Listing which has been submitted electronically in ASCII format and is hereby incorporated by reference in its entirety. Said ASCII copy, created on Aug. 30, 2020, is named "90125-00210-Sequence-Listing-AF.txt" and is 95,682 bytes in size.

TECHNICAL FIELD

The invention relates to a cell-free expression system, the reaction mixture containing all the cell-free reaction components necessary for the in vitro transcription/translation mechanism, amino acids, nucleotides, metabolic components which provide energy and which are necessary for protein synthesis. The invention further relates to an in vitro cell-free expression system incorporating a novel inorganic polyphosphate-based energy regeneration system which may result in higher yields of subject expression products, such as proteins. The invention further relates to a device for in vitro cell-free gene expression. Additionally, the invention relates to a novel inorganic polyphosphate-based energy regeneration system which may be incorporated into diagnostic applications and/or assays.

BACKGROUND

Cell-free expression systems (also known as in vitro transcription/translation, cell-free protein expression, cell-free translation, or cell-free protein synthesis) represent a molecular biology technique that enables researchers to express functional proteins or other target molecules in vitro. Compared to in vivo techniques based on bacterial or tissue culture cells, in vitro protein expression is considerably faster because it does not require gene transfection, cell culture or extensive protein purification. Another advantage of such systems is that often the target protein to be expressed may be toxic to a host cell, or generally incompatible with cellular expression, making in vivo systems impractical if not wholly ineffective vehicles for protein expression.

More specifically, cell-free expression systems generate target molecules and complexes such as RNA species and proteins without using living cells. A typical cell-free expression system may utilize the biological components/machinery found in cellular lysates to generate target molecules from DNA containing one or more target genes. Common components of a typical cell-free expression system reaction may include a cell extract generally derived from a cell culture lysate, an energy source such as ATP, a supply of amino acids, cofactors such as magnesium, and the nucleic acid synthesis template with the desired genes, typically in the form of a plasmid synthesis template, or linear expression (or synthesis) template (LET or LST). A cell extract may be obtained by lysing the cell of interest and removing the cell walls, genomic DNA, and other debris through centrifugation or other precipitation methods. The remaining portions of the lysate, or cell extract may contain the necessary cell machinery needed to expresses the target molecule.

A common cell-free expression system involves cell-free protein synthesis (CFPS). To produce one or more proteins of interest, typical CFPS systems harness an ensemble of catalytic components necessary for energy generation and protein synthesis from crude lysates of microbial, plant, or animal cells. Crude lysates contain the necessary elements for DNA to RNA transcription, RNA to protein translation, protein folding, and energy metabolism (e.g., ribosomes, aminoacyl-tRNA synthetases, translation initiation and elongation factors, ribosome release factors, nucleotide recycling enzymes, metabolic enzymes, chaperones, foldases, etc.). Common cell extracts in use today are made from *Escherichia coli* (ECE), rabbit reticulocytes (RRL), wheat germ (WGE), and insect cells (ICE), and even mammalian cells (MC).

Despite many advantageous aspects of cell-free expression systems, several obstacles have previously limited their use as a protein production technology. These obstacles have included short reaction durations of active protein synthesis, low protein production rates, small reaction scales, a limited ability to correctly fold proteins containing multiple disulfide bonds, and its initial development as a "black-box" science. One significant limitation found in traditional cell-free expression systems is the difficulty in supplying the intense energy and substrate needs of protein synthesis needed for transcription/translation without deleterious concomitant changes in the chemical environment. Furthermore, expensive reagent costs, particularly high energy phosphate chemicals in the form of nucleotides and secondary energy sources, limit the practical uses of such traditional cell-free expression systems.

One of the major limiting factors for in vitro cell-free expression systems is energy regeneration. For example, after initiation of cell-free protein synthesis, production typically continues until one of the substrates (e.g., ATP, cysteine, etc.) is depleted, or byproduct accumulation (e.g., inorganic phosphate) reaches an inhibitory concentration. As such, the inability of any cell-free expression system to efficiently regenerate an appropriate energy source can act as a limiting factor, reducing the overall run-time and ultimate yields of the system. Moreover, it is impracticable, in addition to being prohibitively expensive, to simply add additional ATP into a cell-free expression system as high levels of ATP may actually inhibit protein expression.

To address these issues, traditional cell-free expression systems rely on the addition of supplementary energy sources, primarily in the form of Phosphoenolpyruvate (PEP) and Pyruvatekinase (PK) or Creatinephosphate (CP) and Creatinekinase (CK) or other similar compounds. However, such energy supplementation has significant limitations. First, both substrates PEP and CP have only a functional limited lifetime under in vitro conditions, and their reaction by-product pyruvate is inhibitory to in vitro translation. Second, as noted above, these substrates significantly increase the costs for in vitro applications. Third, both enzymes PK and CK have been demonstrated to have only a limited total turnover number of 3-4 times prior to degradation/inactivity further limiting their usefulness as an energy regeneration source. A protein "turnover" or turnover number (also termed $k_{cat}$) may be defined as the maximum number of chemical conversions of substrate molecules per second that a single catalytic site will execute for a given enzyme concentration. As a result, because of its poor turnover number, both PK and CK enzymes must be added in significant amounts which limit the run-time of in vitro applications while also increasing costs.

In a more specific example, current *E. coli*-based cell-free systems primarily rely on creatine phosphate/creatine kinase or on phosphoenolpyruvate (PEP) and Pyruvate Kinase (PK) as the main energy regenerating system, though it is established that PK has a total turnover number in the low single digits and the side-product pyruvate is an inhibitor of the translation reaction. In this manner, not only does the current invention's cellular energy regeneration system teach away from traditional cell-free expression systems, but indeed, represents a demonstrable improvement over traditional cell-free expression systems known in the art.

As a result, there exists a need for a more energetically efficient and robust cell-free expression system that may, for example, have longer reaction duration and increased protein synthesis rates, ultimately producing higher protein yields. Indeed, the foregoing problems regarding the cell-free expression systems, and in particular energy regeneration within these systems, represent a long-felt need for an effective—and economical—solution to the same. While implementing elements may have been available, actual attempts to meet this need may have been lacking to some degree. This may have been due to a failure of those having ordinary skill in the art to fully appreciate or understand the nature of the problems and challenges involved. As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field.

As will be discussed in more detail below, the current inventive technology overcomes the limitations of traditional cell-free expression systems, in particular their energy use limitations, while meeting the objectives of a truly energetically efficient and robust in vitro cell-free expression system that results in longer reaction durations and higher product yields.

BRIEF SUMMARY OF THE INVENTION

Generally, the inventive technology relates to cell-free expression systems. One aim of the invention may be to provide methods of cell-free expression that include novel compositions, apparatus and procedures that result in longer reaction times, higher reaction efficiency, and improved reaction stability that ultimately produce higher yields of a desired expression product.

Another aim of the invention may be to provide an improved cell-free expression system, which in one embodiment may include novel systems and methods of energy regeneration. For example, in one preferred embodiment, the inventive technology may include an in vitro cell-free expression system incorporating a novel inorganic polyphosphate-based energy regeneration system. In this preferred embodiment, energy regeneration may be achieved through the addition of inorganic polyphosphate and synergistic high efficiency kinase proteins isolated and purified from select bacterial strains. These kinase proteins may drive the high-efficiency chemical regeneration of the cellular energy source adenosine triphosphate (ATP) within the cell-free expression system. This improved energy regeneration allows for continued activity of the cell-free expression system resulting in higher yields of subject expression products, such as proteins.

In certain embodiments this inorganic polyphosphate-based energy regeneration system may be applied to a variety of cell-free expression systems. For example, in one preferred embodiment the novel energy regeneration system may allow for longer run-time of the system prior to chemical energy depletion and higher yields of expression products, such as proteins, from cell-free translation systems.

Another aim of the inventive technology may relate to energy dependent processes and/or diagnostic assays. Specifically, the inventive technology may include improved in vitro ATP-dependent processes and/or assays having an inorganic polyphosphate-based energy regeneration system. In one preferred embodiment, the inventive energy regeneration system may include an in vitro ATP-dependent protein activity assay having an inorganic polyphosphate-based energy regeneration system. In this embodiment, energy regeneration within the assay may be achieved through the addition of synergistic high-efficiency kinase proteins isolated and purified from select bacterial strains. These kinase proteins may drive the high-efficiency chemical regeneration of ATP in an ATP-dependent assay. This embodiment may allow for longer assay run-time prior to chemical energy depletion, which in-turn may allow for improved assay performance and sensitivity.

Additional aim of the inventive technology may include the identification, isolation, purification and/or modification of RNA polymerase (RNAP) proteins from certain bacterial strains that exhibit increased stability, thermostability and enzymatic activity and/or turnover in cell-free in vitro systems such as those described herein. In one embodiment, a thermostable bacterial RNA polymerase may allow the biosynthesis of messenger RNA (mRNA) from DNA constructs at a higher stability and at higher than traditional temperatures which may aid the unfolding of genomic or Cosmid DNA under, or without the control of, a specific promoter. In one preferred embodiment, this highly stable RNAP may be used to generate expression products in a cell-free expression system, such as in vitro transcription, in vitro cDNA production, and in vitro transcription/translation expression systems. This highly stable RNAP may be used in cell-free expression systems having specific enzymes to regenerate energy sources/substrates such as Uridine triphosphate (UTP), Guanosine triphosphate (GTP), and/or Cytidine triphosphate CTP, as well as an inorganic polyphosphate energy regeneration system as generally described herein. In this embodiment, the increased stability of the RNA polymerase proteins may allow for increased run-time and higher yields in cell-free expression systems as generally described herein. Naturally, reference to certain energy substrates include all forms of such substrates. By way of example, disclosure of GTP includes reference to GTP encompasses guanosine diphosphate (GDP) and guanosine monophosphate (GMP).

Yet another aim of the invention may be to provide one or more genetically modified strains of bacteria that may be optimized for use in cell-free expression systems. Examples of such modifications may include the elimination of certain genes that may, for example, have proteolytic, ribonuclease, and/or sporulation activity to name a few. Additional embodiments may include genetically engineered bacteria that overexpress certain sigma factors that may facilitate promotor recognition in vitro of linear PCR products, as well as resulting in the upregulation of RNAP.

Another aim of the current invention may provide for a novel cell-free expression system growth medium. In certain embodiments, the invention relates to a modified growth medium that may be used in a cell-free expression system. This novel medium may allow optimal bacterial grown without the presence of toxic metal salts and or metal ion chelators.

Additional aims of the inventive technology may become apparent from the detailed disclosure, figures and claims set forth below.

BRIEF DESCRIPTION OF THE FIGURES

The accompanying figures, which are incorporated into and form a part of the specification, illustrate one or more embodiments of the present invention and, together with the description, serve to explain certain aspects of the inventive technology. The drawings are only for the purpose of illustrating one or more preferred embodiments of the invention and are not to be construed as limiting the invention.

FIG. 3: listing of additional amino acids added to native RNAP protein subunits and RpoD.

MODE(S) FOR CARRYING OUT THE INVENTION(S)

Figure 1A:
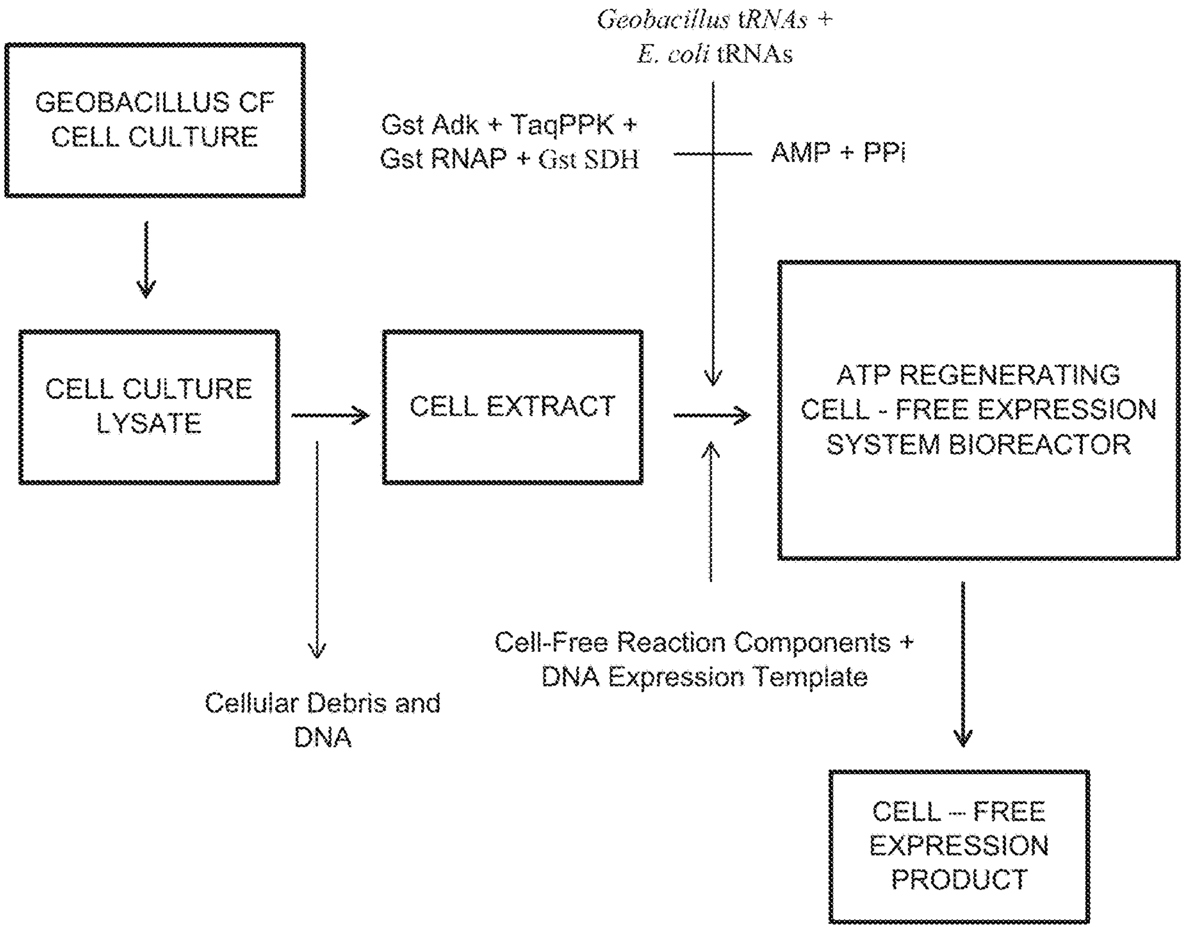
FIG. 1*a*: shows a general diagram of a thermotolerant cell-free expression system fermenter in one embodiment thereof.
Figure 1B:
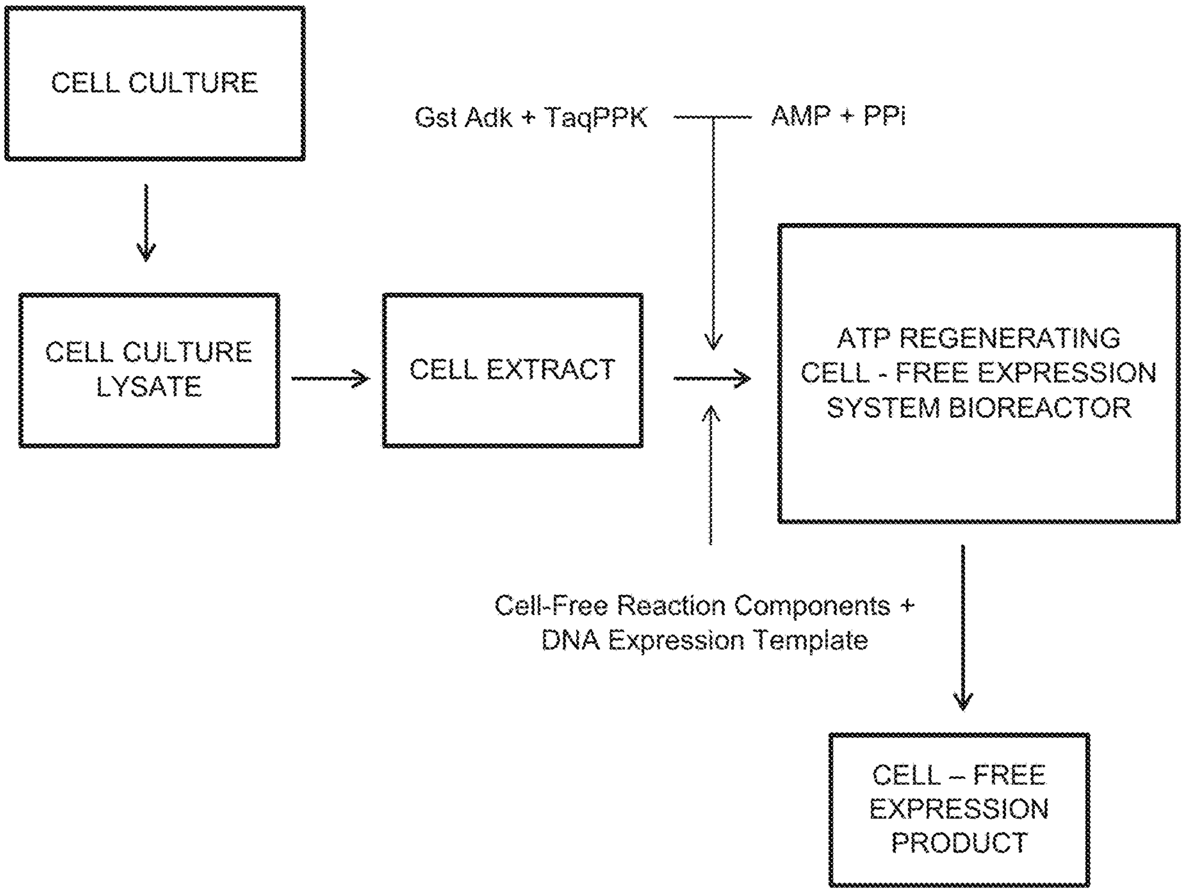
FIG. 1*b*: shows a general diagram of a cell-free expression system fermenter in one embodiment thereof.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The current technology includes a novel inorganic polyphosphate-based energy regeneration having applications for cell-free expression systems including but not limited to: in vitro transcription systems having for example, cell extracts and/or supplemented substrates and enzymes providing for the regulation of UTP, GTP, CTP; in vitro translation systems; in vitro (ATP-dependent) protein activity assay systems; and combined in vitro transcription/translation systems.

In certain embodiments, such energetically synergistic gene products utilized in a cell-free expression system may include, but not be limited to, Adenosyl Kinase (AdK), and/or Polyphosphate Kinase (PPK).

Generally, PPK catalyzes the reversible formation of ATP and inorganic polyphosphate:

$$ADP+PP_i \leftrightarrow ATP+PP_{i-1}$$

Generally, Adk catalyzes the interconversion of adenine nucleotides, namely 2 ADP may be converted into one ATP and one AMP.

$$2ADP \leftrightarrow 1ATP+1AMP$$

In some instances, such energetically synergistic gene products may be generally thermostable, and in some instances, genetically modified for their use in a cell-free expression system. This AdK/PPK coupled energy regulation system may be utilized in a cell-free expression system, as well as other ATP-dependent reactions, diagnostic application and/or assays.

As will be detailed below, the AdK/PPK energy regulation system may include AdK and/or PPK proteins derived from a variety of sources, such as various bacterial species as well as recombinant expressions. As such, while in some embodiments, certain AdK and/or PPK genes or proteins may be specifically identified, however it should be noted that the identification of AdK and/or PPK may generally encompass all AdK and/or PPK genes or proteins and their homologs, paralogs and orthologs as well as all genetically modified versions. Such genetic modification may include mutations, such as one or more point mutations, that may enhance the protein's activity.

In one embodiment, the inventive technology may include the identification and isolation of one or more energetically synergistic gene products from selected bacterial species. Generally referring to FIG. 4, in one preferred embodiment AdK may be cloned from gDNA from *Geobacillus stearothermophilus* utilizing techniques generally described above. In addition, PPK may be cloned from gDNA from *E. coli* (ecPPK) (SEQ ID NO. 9), or as will be discuss below, in one preferred embodiment, PPK may be cloned and/or modified from a thermophilic and/or thermotolerant bacteria, such a *Thermus aquaticus* (TaqPPK).

For example, in one preferred embodiment gDNA from *G. stearothermophilus* was isolated from an approximately 20 ml overnight culture. The *G. stearothermophilus* culture may be pelleted and the gDNA isolated using, for example a commercially available kit, such as Macherey-Nagel NuceloSpin Microbial DNA Kit. The gDNA may then be concentrated using ethanol precipitation. This may generally be accomplished by adding a salt and ethanol to a solution containing the gDNA which may precipitate the gDNA which may again be pelleted for example, with a centrifuge and then resuspended in DNase-/RNase-free water. The isolation of gNDA containing a PPK gene in *T. aquaticus* may be isolated and concentrated by similar means as described above.

Similar to the above referenced description, in one preferred embodiment, both Gst AdK and/or TaqPPK may be cloned using specific primers which may be designed based on the nucleotide sequences of each gene. In this embodiment, both forward and reverse primers may be generated that contain specific restriction sites for the introduction of the subject genes into a selected expression vector(s). In one preferred embodiment, forward and reverse primers may be generated that contain restriction sites to specifically introduce the Gst AdK and/or TaqPPK genes into IBA StarGate Expression Vectors. The subject primers and gDNA from Gst and *E. coli* may be subject to individual polymerase chain reactions (PCR) to amplify the Gst AdK and/or TaqPPK genes respectively. In one embodiment, individual PCR's for both the Gst AdK and/or ecPPK genes may be performed using standard MasterMix reactions and 50 ng of input gDNA isolated from *G. stearothermophilus* and *E. coli* (Table 1) respectively.

Figure 2A:
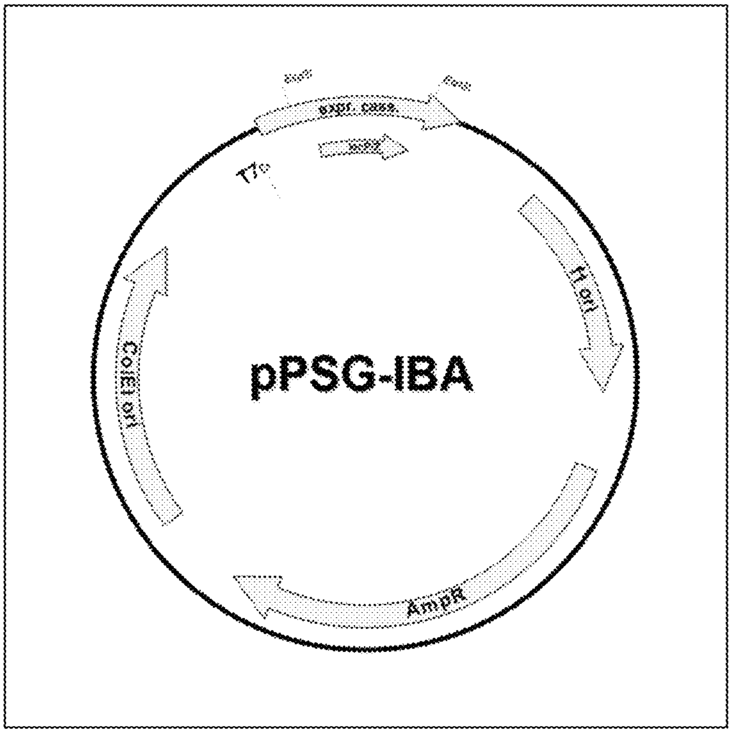
FIG. 2*a*: shows a Gst AdK expression vector in one embodiment thereof.
Figure 2B:
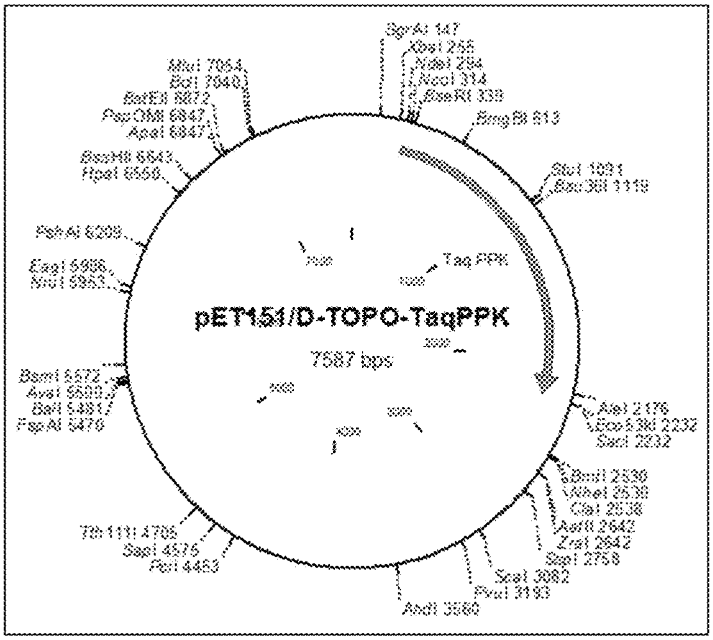
FIG. 2*b*: shows a TaqPPK expression vector in one embodiment thereof.
Figure 12:
FIG. 12: is a comparison of a literature and recombinant PPK protein sequences.

In a preferred embodiment, a thermostable PPK enzyme may be derived from the thermophilic *T. aquaticus* (TaqPPK) and may further be coupled in the inventive cell-free expression system with the Gst AdK (SEQ ID NO. 8) generally identified above. In this embodiment, the PPK literature protein sequence (SEQ ID NO. 10; FIG. 12) was used to back translate into DNA. The sequence was then codon-optimized for *E. coli* and the gene was subcloned into pET151/D-TOPO for expression (FIG. 2*b*). In this embodiment, the subcloned PPK gene, generally identified as TaqPPK, from *Thermus aquaticus* was genetically modified to contain additional non-naturally occurring amino acids at the N-terminus. These additional non-naturally occurring amino acids include: 1) a 6×His-Tag; 2) a V5 epitope tag and 3) a TEV cleavage site (SEQ ID NO. 11). As noted in Table 1, these three genetic modifications are part of the pET151 backbone and may facilitate expression and purification. TaqPPK was expressed in BL21(DE3) and purified using the methods generally described herein.

In one embodiment, the Gst AdK and TaqPPK gene DNA sequences that have been amplified through the PCR process may be isolated. In one preferred embodiment, PCR reactions may be analyzed on 1% Ethidium Bromide agarose gels and the Gst AdK and/or PPK genes may be isolated by agarose gel extraction and/or PCR purification methods known within the industry such as Macherey-Nagel NucleoSpin Gel and/or PCR Clean-up. These isolated genes may then be inserted into an appropriate delivery vector. For example, in one embodiment the previously generated genes fragments and a selected vector, in this embodiment an appropriate vector (see e.g. FIG. 2*a-b* respectively), may be digested with selected restriction enzyme(s) and ligated through, for example, a 3:1 T4 DNA ligase reaction which may be available commercially as a Thermo Fisher Scientific Rapid DNA Ligation Kit. It should be noted that for this, and all other embodiments, each gene fragment may be separately ligated into an individual delivery vector and transformed into a select bacterial strain or other appropriate cell. Other embodiments may include ligation of multiple gene fragments into a delivery vector and transformed into a select bacterial strain to be co-expressed.

In this embodiment the ligated Gst AdK and TaqPPK genes and plasmid vector may be individually or collectively transformed into a selected bacterial strain. In a preferred embodiment the individual ligated vector(s) may be transformed into Top10 competent *E. coli* that may be configured to have a high rate of transformation efficiency. In this embodiment, Top10 competent *E. coli* may include mutations in the recA gene which may reduce DNA recombination promoting plasmid vector stability and may further include an endA gene knockout which may reduce non-specific endonuclease activity improving plasmid vector yield and quality.

Successfully transformed bacteria may be identified, for example through positive gene detection PCR, or other known methods, and may then be subsequently cultured to generate multiple copies of the plasmid vector within the growing bacterial colony. In a preferred embodiment, the plasmid vector DNA may be isolated and sub-transformed into another select bacterial strain. In a preferred embodiment, the prepared plasmid vector DNA may be sub-transformed into a high expression strain of *E. coli*, such as BL21(DE3) for optimal protein expression.

In one embodiment the inventive technology may include individual expression of both the Gst AdK and TaqPPK proteins each having a selected molecular tag. In this embodiment, Gst AdK and/or PPK proteins may each be configured to contain a poly-His or His-6 tag, which may be used later for protein purification. In this embodiment, the expressed Gst AdK and/or PPK proteins may be detected and purified because the string of histidine residues bind to several types of immobilized metal ions, including nickel, cobalt and copper, under appropriate buffer conditions.

In one embodiment, a tagged Gst AdK (SEQ ID. NO. 8) and/or TaqPPK (SEQ ID. NO. 11) protein may be individually expressed and purified. In this preferred embodiment, the individually His-6 tagged Gst AdK and/or PPK proteins may be expressed in a BL21(DE3) strain of *E. coli*. In this embodiment, the BL21(DE3) strain of *E. coli* may be cultured in NYZ medium, which among other things, may lack lactose which may induce certain proteases that could potentially degrade any expressed proteins, reducing overall yields. Protein expression may be induced at a certain optical density (OD) of bacterial growth. In a preferred embodiment, at approximately OD 0.7, protein expression may be induced by the addition of 0.25 mM isopropyl β-D-1-thiogalactopyranoside (IPTG) for 6-8 hours at 30-32° C. IPTG is a molecular reagent that mimics allolactose, a lactose metabolite that triggers transcription of a lac operon in the plasmid vector DNA, thereby inducing protein expression where the subject gene, in this case the Gst AdK and/or TaqPPK genes respectively, which may be under the control of a lac operator.

In this preferred embodiment, the individual BL21(DE3) cultures may be lysed and a lysate may be prepared and passed through a metal ion-charged resin. The individual lysates may pass through a Ni-charged IMAC resin, where the His-6 tags on the Gst AdK and/or TaqPPK proteins may bind to the immobilized nickel-ion on the resin. Non-binding and non-specific binding proteins may further be removed, in this embodiment through the addition of 5 mM Imidazole, the non-binding and non-specific binding proteins may be removed while the Gst AdK and TaqPPK proteins remain bound to the resin. Again, as noted above, the aforementioned protein purifications steps may be accomplished individually for both Gst AdK and TaqPPK proteins.

The Gst AdK and/or TaqPPK proteins may then be individually eluted by the addition of 300 mM Imidazole or other known methods. The presence of the proteins may be demonstrated through SDS-PAGE and protein purity may be additionally shown by FPLC UV-profiles. In a preferred embodiment the individually purified proteins may be stored in in vitro transcription/translation compatible buffer conditions at a concentration of 13 mg/ml for Gst AdK and 10 mg/ml for PPK at −20° C. for later use.

Further, ATP determination assays may be performed to verify functionality of the Gst AdK and/or PPK proteins in the presence of a polyphosphate. Such an assay may quantify the levels of adenosine triphosphate (ATP) as well as ATP production. ATP (see FIG. 6) is an adenine nucleotide comprised of three phosphate groups esterified to the sugar moiety, found in all living cells. Adenosine triphosphate is involved in energy production for metabolic processes as well as RNA and protein synthesis.

In a preferred embodiment, inorganic polyphosphate, in this case sodium polyphosphate, may be provided as an energy source for the system in an in vitro ATP-dependent system. Isolated and purified Gst AdK and/or TaqPPK may be added to this cell-free expression system. In one preferred embodiment Gst AdK to TaqPPK may be added to a cell-free expression system, or other assay, diagnostic or system, wherein the ratio of Gst AdK to TaqPPK may include higher amounts of Gst AdK as compared to TaqPPK. In in one embodiment, Gst AdK to TaqPPK may be added to this system in an approximate molar ratio of between approximately 3:1-4:1. It should be understood that such ratios are merely exemplary and other ratios are within the scope of this invention. For example, in other embodiments, Gst AdK to TaqPPK may be added to this system in an approximate molar ratio including, but not limited to [See concentration email]1:1, 2:1, 3:1, 5:1, 5:1, 7:1, 8:1, 9:1, 10:1 and the like.

Figure 8:
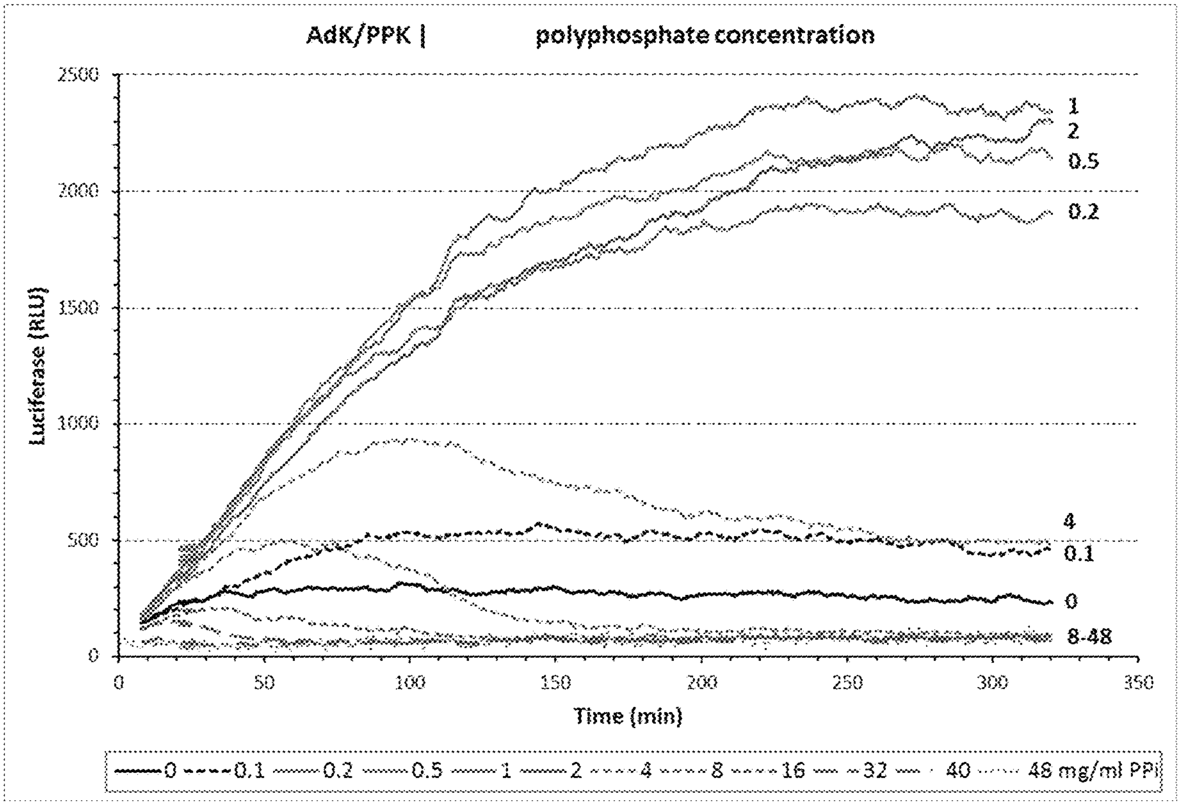
FIG. 8: demonstrating ATP energy regeneration system at varied polyphosphate concentrations.

As generally shown in FIG. 8, in another preferred embodiment, isolated and purified Gst AdK and/or TaqPPK may be added to this cell-free expression system with a quantity of inorganic polyphosphate. In one embodiment, this quantity of inorganic polyphosphate may include an optimal polyphosphate concentration range. In this preferred embodiment, such optimal polyphosphate concentration range being generally defined as the concentration of inorganic polyphosphate (PPi) that maintains the equilibrium of the reaction stable. In this preferred embedment, optimal polyphosphate concentration range may be approximately 0.2-2 mg/ml PPi.

As noted above, PPK can synthesize ADP from polyphosphate and AMP. In this preferred embodiment the coupled action of Gst AdK and PPK, may remove adenosine diphosphate (ADP) from the system by converting two ADP to one ATP and one adenosine monophosphate (AMP):

Gst AdK

2 ADP → 1 ATP + 1 AMP

This reaction may be sufficiently fast enough to drive an equilibrium reaction of PPK towards production of ADP:

TaqPPK

AMP + (phosphate)$_n$ → ADP + (phosphate)$_{n-1}$

In this system, the presence of higher concentrations of AMP may further drive the TaqPPK reaction towards ADP.

Figure 4:
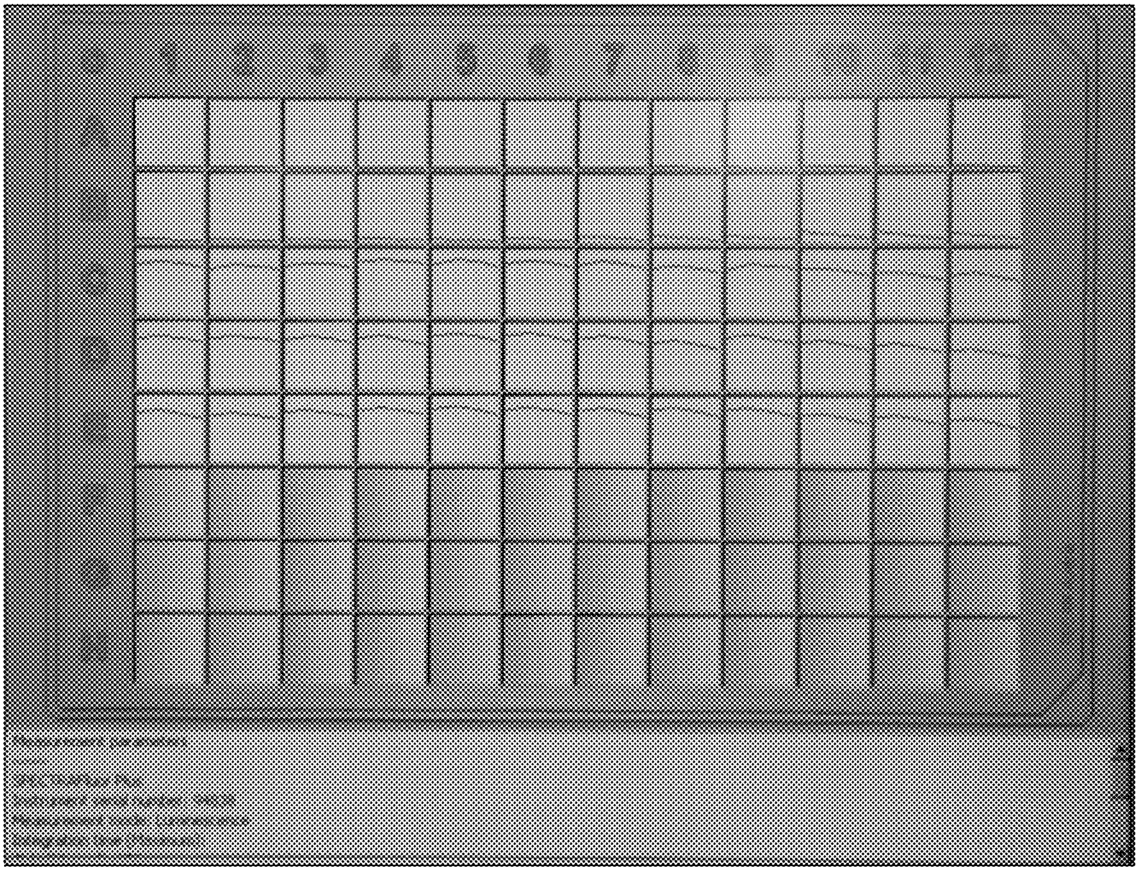
FIG. 4: ATPase Luciferase assay demonstrating ATP regeneration utilizing Gst AdK/PPK coupled energy regeneration system. The data specifically showing: row A: 10 uM ATP in 200 ul standard ATPase Luciferase assay in each well; row B: 10 uM ATP, standard PEP/PK conditions (200 uM PEP, 0.02 U/ml PK), row C: 10 uM ATP, ratio PPK/Gst AdK (4:1) total of 1 ug/ml; row D: 10 uM ATP, ratio PPK/Gst AdK (1:1) total of 1 ug/ml; row E: 10 uM ATP, ratio PPK/Gst AdK (1:4) total of 1 ug/ml; columns 1-3: 1 ul (10 mg/ml polyPhosphate); columns 4-6: 3 ul (10 mg/ml polyPhosphate); columns 7-9: 6 ul (10 mg/ml polyPhosphate); columns 10-12: 10 ul (10 mg/ml polyPhosphate). All reactions were recorded continuously for 137 minutes in 96-well plates in a Tecan plate reader (X axis for each well). The total relative luminescence was recorded and is shown for each well (Y axis).
Figure 5:
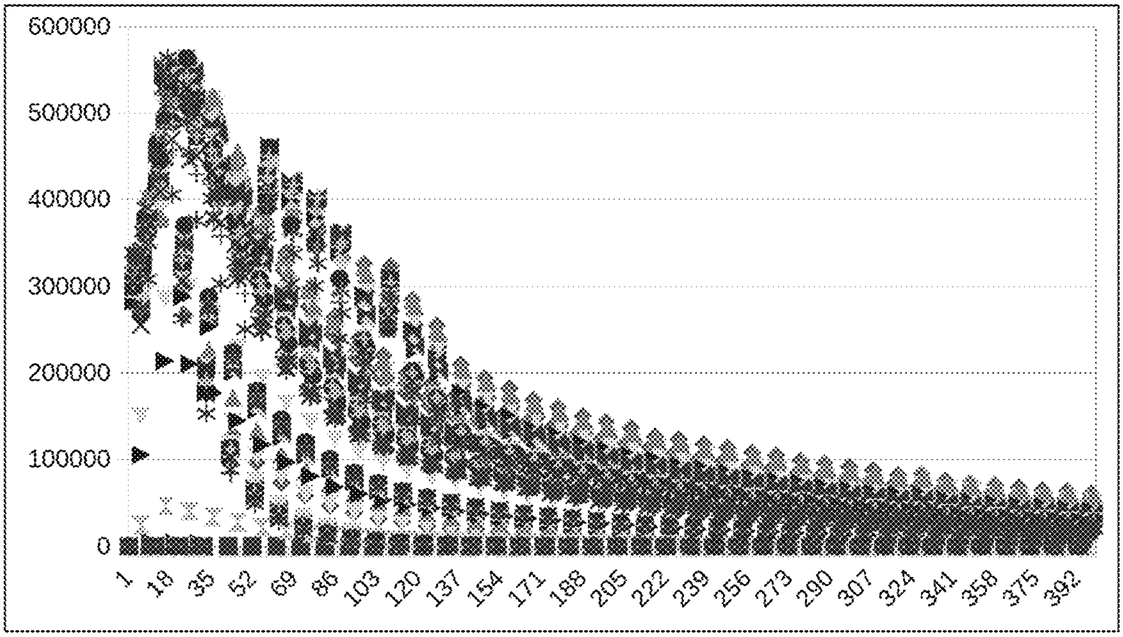
FIG. 5: Under same conditions as for FIG. 4, ATPase Luciferase assay reactions are presented in linear representation of all recorded data points of relative luminescence of Luciferase/D-Luciferin based ATPase assays of ATP, PEP/PK and of the Gst AdK/PPK PPi system for the continuously recorded 392 minutes (X axis). The relative luminescence (same scaling, same reading, same plate) are represented by the Y axis. A separation of all three systems becomes very distinct over time.
Figure 6:
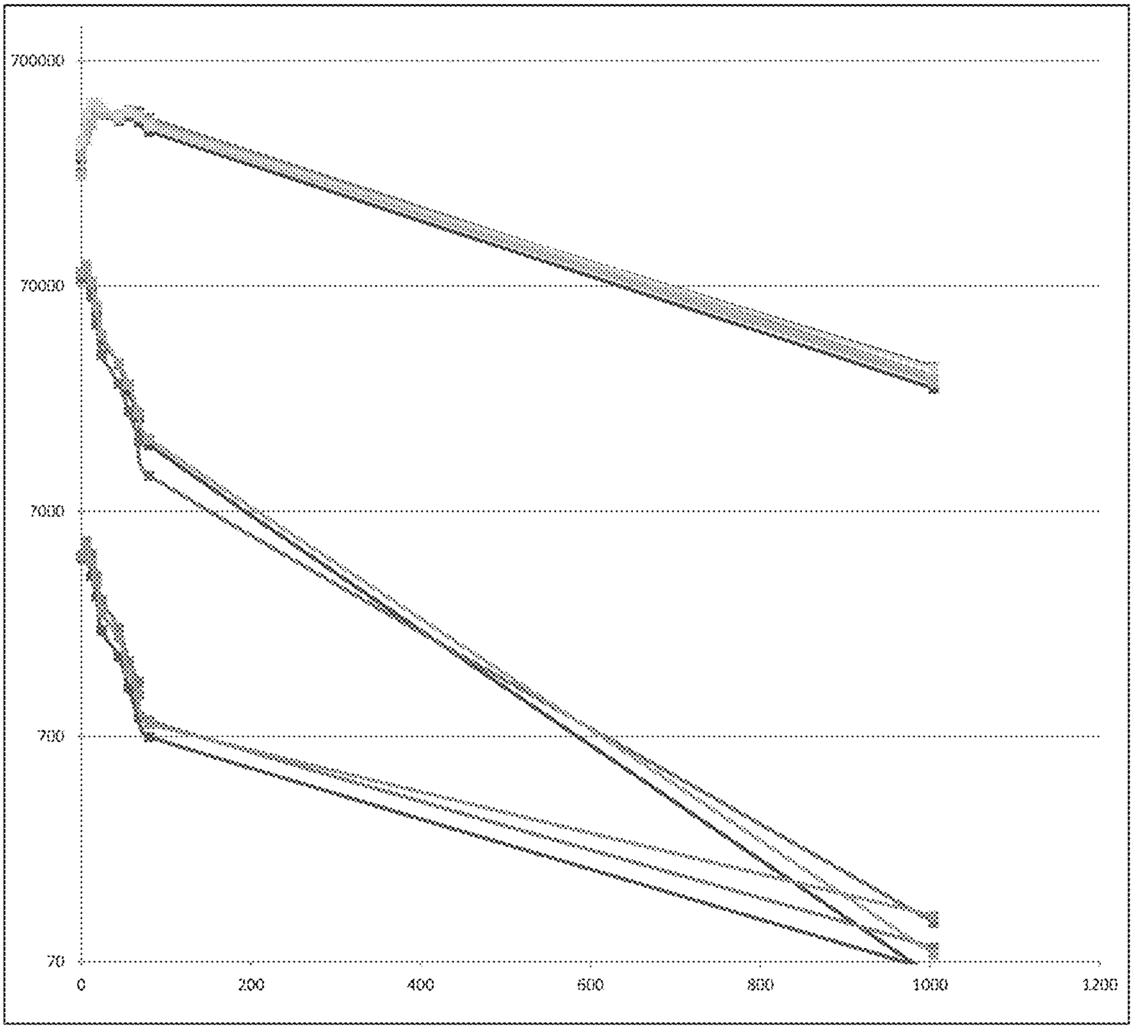
FIG. 6: Logarithmic representation of the relative luminescence in Luciferase/D-Luciferin based ATPase assays as an average of all recorded data points (5 independent experiments) of the 3 repeats of: 10 uM ATP in 200 ul assay, 10 uM ATP with PEP/PK conditions (200 uM PEP, 0.02 U/ml PK), 10 uM ATP, ratio PPK/AdK (4:1) total of 1 ug/ml protein and 3 ul (10 mg/ml polyPhosphate). Experiments were recorded for an additional data point after 1008 minutes. All plates stayed in the plate reader to prevent photo bleaching.

Again, as demonstrated in FIGS. 4-6, in ATP determination assays the ATP regeneration rate of the PPK/AdK energy (ATP) regeneration system is significantly higher compared to the traditional PEP/PK energy production systems. In some embodiments the initial ATP conversion rate may be approximately 10-times higher compared to traditional PEP/PK systems under comparable conditions. Additionally, the Gst AdK and PPK further demonstrated in FIGS. 4-6, may have a higher total turnover number which results in a detectable ATP regeneration for an extended period, which in this embodiment was up to 12 hours.

Incorporation of TaqPPK may further result in a detectable ATP regeneration in excess of 12 hours. Such ATP regeneration turnover being significantly higher than traditional in vitro ATP regeneration systems described above. In other embodiments, Gst AdK and/or TaqPPK may include improved salt tolerance allowing continued enzymatic activity and/or turnover in salt concentrations that would be inhibitory for other AdK proteins. As such, it can be seen how Gst AdK and TaqPPK, (as well as AdK and/or PPK and their homologs derived from various other bacteria, including but not limited to, thermophilic and/or thermotolerant microbial strains) in the presence of a polyphosphate may work synergistically within a cell-free expression system to regenerate the cellular energy source ATP:

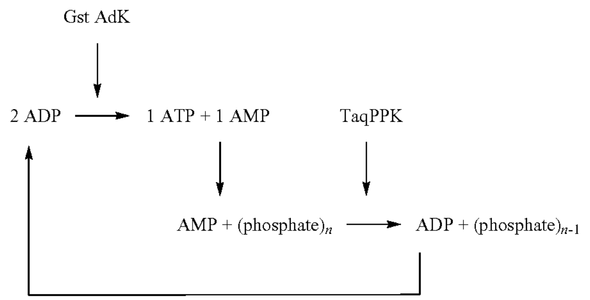

As noted above, in certain embodiments ribosomes, and ribosomal factors may be included in a cell-free expression system. Notably, ribosomes, and ribosomal factors are dependent on guanosine triphosphate (GTP) for their energy, not ATP. As such, in certain preferred embodiments, a cell-free expression system may include one or more nucleotide kinase enzymes NDPK that may convert ATP into GTP which may be utilized by the ribosomes, and ribosomal factors in a cell-free expression system incorporating such factors. As used herein, the term "NDPK" means an enzyme having the activity of the enzyme classified as EC 2.7.4.6, namely the transfer of the γ-phosphate group of a nucleoside triphosphate ($N_1TP$) to a nucleoside diphosphate ($N_2DP$) via a ping-pong mechanism where each step is part of a reversible process, such that the multistep equilibrium is of the following form.

NDPK+NTP↔NDPK~NTP↔NDPK-P~NDP↔NDPK-P+NDP

A ping-pong mechanism integrates phosphorylation of a histidine residue by transferring terminal phosphate group (γ-phosphate) from ATP to NDP β-phosphate in order to produce an NTP, and NDPK catalyzes such reversible reactions. NTP phosphorylates a histidine, which in turn phosphorylates NDP. NDPK are involved in the synthesis of nucleoside triphosphates (NTP), such as guanosine triphosphate (GTP), cytidine triphosphate (CTP) and uridine triphosphate (UTP), thymidine triphosphate (TTP). The ping-pong mechanism can further be visualized as:

the NDPK may only need to be added at low concentrations, for example 1/20 to 1/5 of the concentration of ADK, and preferably 1/10 of the concentration of Adk. (See Table 2, and FIG. 16)

Certain embodiments of the inventive technology may include cell-free expression systems having an improved energy regeneration system. In one preferred embodiment, a cell-free expression system, such as an in vitro transcription and/or translation system may be configured to include an inorganic polyphosphate energy regeneration capability that may further include thermostable RNA polymerase (RNAP) from select bacterial strains.

In one preferred embodiment, RNAP subunits alpha (SEQ ID NO. 1), beta (SEQ ID NO. 2), beta' and or beta' (opt) (SEQ ID NO. 3 and SEQ ID NO. 4 respectively), delta (SEQ ID NO. 5) and omega (SEQ ID NO. 6) from the bacterial species *Geobacillus stearothermophilus* were identified, cloned, purified and prepared for use in a cell-free protein expression system. It should be noted that *G. stearothermophilus* is a gram positive thermophilic bacteria characterized by an inner cell membrane and a thick cell wall. *G. stearothermophilus* is a rod shaped anaerobe found in thermophilic habitats like thermal vents or hot springs.

An RNAP from *G. stearothermophilus* (Gst RNAP) may be identified, cloned, expressed and then purified as generally described herein. In this embodiment the Gst RNAP may be more stable than, for example, standard RNAP from non-extremophile bacteria such as *E. coli*. The Gst RNAP may have improved thermostability, as well as improved kinetic stability, such that it may remain viable to catalyze the production of mRNA in an in vitro system for a longer period of time than other RNAP variants used in traditional cell-free expression systems.

In one preferred embodiment, a thermostable Gst RNAP may be cloned and transformed into a high expression *E. coli* strain. This thermostable Gst RNAP may be cloned, isolated and purified then introduced into a cell-free expression system in the presence of a target genetic material, such as plasmid and/or linear DNA containing one or more select genes, and allowed to produce mRNA transcripts of the select genes. In one embodiment, these mRNA transcripts may be introduced to, or combined with a bacterial or other cellular extract. The extract may contain the necessary elements for DNA to RNA transcription, RNA to protein translation, protein folding, and energy metabolism. As

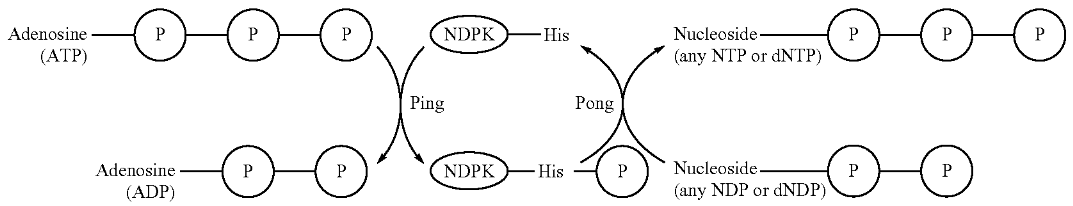

In one preferred embodiment, a quantity of NDPK may be isolated and included in a cell-free expression system, and preferably a cell-free expression system configured to produced peptides. In this embodiment, the NDPK may convert ATP to GTP in an equilibrium. In a preferred embodiment, a thermostable NDPK, or NDPK derived from a thermophile may be used, for example, in one embodiment a thermostable NDPK derived from *Thermus thermophilus* according to SEQ ID NO. SEQ ID NO. 23 may be used to convert ATP to GTP in a cell-free expression system. In this embodiment, noted above, in this embodiment, isolated and purified TaqPPK and Gst AdK may be added to, for example, a cell extract of a cell-free expression system, as well as a quantity of one or more polyphosphates during protein translation to provide a mechanism of improved ATP regeneration.

In this preferred embodiment, translation of the target mRNA transcripts may generate one or more select protein (s) while synergistic activity of the TaqPPK, Gst AdK and polyphosphate provide enhanced ATP regeneration, allowing longer run-times of the cell-free expression system, at possibly higher temperatures if desired, and having a higher turnover number resulting in overall higher protein yields. In this embodiment, the presence of a highly stable Gst RNAP allows for longer run-times for the production of mRNA transcripts, at possibly higher temperatures without being denatured and having a higher turnover number resulting in higher mRNA transcripts and ultimately protein yields within the cell-free expression system.

The invention further relates to an improved in vitro transcription/translation system, generally referred to as a cell-free expression system. In one embodiment, this cell-free expression system may include one or more genetically modified strains of thermophilic or thermotolerant bacteria that may be developed for use in cell-free extract preparation. In a preferred embodiment, a genetically modified strain of a thermophilic bacteria, such as a *Geobacillus* strain, may be developed and used for cell-free (CF) extract preparation and for in vitro transcription/translation. *Geobacillus* strains generally exhibit a high growth temperature (52-55° C.) compared to *E. coli* (35-37° C.). This thermal differential may allow for higher protein stability and toleration of higher protein densities in CF extract preparations. Further, *Geobacillus* strains' thermophilic attributes may allow for increased stability for other enzyme-, and enzymatic functions, such as, but not limited to: amino acid-synthases; ribosomes; DNA-dependent RNA polymerase; sigma factor(s); and ATP regenerating and glycolytic enzymes.

Bacteria from the genus Geobacillae are also advantageous for CF extract preparations. Being firmicutes, they are $O_2$-tolerant or strictly aerobic, under specific conditions. Handling, fermentation and extract preparations of anaerobic thermophiles may be significantly more complex, costlier, and have additional uncertainties related to enzyme stability due to oxidizing conditions of the atmosphere. Moreover, Geobacilli are known to have no known health implications to humans, and as such, are suitable to produce clinical material from a CF system.

With respect to the invention's genetically modified *Geobacillus* strain, it was determined that the ribosome binding site (RBS) was predicted and demonstrated by genetic analysis to be identical to, or comparable to, the standard RBS of expression constructs for *E. coli* protein expression strains, allowing the inventive technology in a preferred embodiment to preserve and utilize existing genetic constructs.

In another preferred embodiment, the invention's genetically modified *Geobacillus* strain demonstrated favorable coverage of tRNA codon usage. In one embodiment, bioinformatic analysis was performed using a proprietary software tool with tRNA population distribution to identify strains that cover all or most all potential codons to prevent stalling of the in vitro translation reaction due to rare or not covered tRNA codons. Extracts of this *Geobacillus* strain may be also utilize purified *E. coli* tRNAs, which are recognized by the strain's amino acid synthases. This may allow complete and almost equally distributed codon coverage. This embodiment takes the natural unequal distribution of tRNA codon usage of varying strains, such as *Geobacillus stearothermophilus*, and *Thermophilus aquaticus* into account in favor of a thermodynamically balanced distribution.

As generally discussed above, in one preferred embodiment, a genetically modified bacterial strain was developed for use in a cell-free expression system. In a preferred embodiment, a *Geobacillus* strain was genetically modified to remove and/or reduce the expression of certain enzymes, and to constitutively overproduce enzymes during the fermentation process to facilitate the use of CF extract preparations. (This genetically modified strain may sometimes be generally referred to as "*Geobacillus* CF"). In this embodiment, a Geobacilli was genetically modified to knock-out the strong protease OmpT-homologue, RNaseI, and the DNA-methylation dependent DNase. In this embodiment, the genetic knock-out modifications were accomplished through the selective removal of the transcription control of these genes from the bacterial genome. Other knock-out methods may also be employed, as they are generally known and understood in the art. In this embodiment, the activity of the culture density-dependent sporulation operon was reduced by genetic modification (knocked down) to slow the sporulation process and to increase the bacterial density in culture allowing for higher efficiency and improved CF extract yield.

Again, as generally discussed above, in certain embodiments a genetically modified bacterial strain was developed to overexpress sigma factor, RpoD, to recognize a specific promoter for favored in vitro transcription from linear PCR products. In a preferred embodiment, a *Geobacillus* CF was genetically modified to overexpress sigma factor, RpoD during the fermentation of the strain. This genetically modified overexpression of RpoD elevated expression of this sigma factor above the natural cellular concentration of sigma 70, which in turn resulted in an increased concentration of the bacterial RNAP in the genetically modified *Geobacillus* strain. Finally, the genetically modified bacterial *Geobacillus* strain exhibits growth rates comparable to *E. coli* protein expression strains known in the art. Additional advantages of using the genetically modified Geobacilli strain for CF extract preparation include: 1) a high growth temperature (approximately 52-55° C.) which significantly reduces the potential contamination of the culture; and 2) "spent" fermentation media are simple and non-hazardous, reducing the need for waste treatment, as it would be required for anaerobic thermophiles.

In additional embodiment, a cell extract may be generated from a number of different micro-organisms. For example, cell extracts may be generated from *Escherichia coli* (ECE), rabbit reticulocytes (RRL), wheat germ (WGE), and insect cells (ICE), and even mammalian cells (MC). In additional embodiment, cell-extracts from microalgae may be generated. Such an embodiment may be advantageous, as bacteria do not provide any mechanism to recognize and remove introns. On the other hand, microalgae, like nanochloropsis, have introns and the cellular machinery remove them—which would naturally be a constituent of an microalgae cell extract making the current invention applicable for the production of plant proteins and other expression products.

In vitro cell-free expression, as used herein, refers to the cell-free synthesis of polypeptides in a reaction mixture or solution comprising biological extracts and/or defined cell-free reaction components. The reaction mix may comprise a template, or genetic template, for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. The cell-free synthesis reaction, and/or cellular adenosine triphosphate (ATP) energy regeneration system components may be performed/added as batch, continuous flow, or semi-continuous flow.

As noted above, the current invention may be applicable to a number of assays, and other diagnostic applications. For example, in one embodiment, the addition of the dual enzymes Adk/PPK, along with PPi and AMP may allow for ATP regeneration within any ATP energy dependent assay or diagnostic application, such as a luciferase assay. In one preferred embodiment, a first quantity of Gst AdK, and a first quantity of TaqPPK, may be added to an ATP dependent assay or diagnostic, along with a first quantity of PPi and a first quantity AMP. In this preferred embodiment, cellular ATP energy regeneration may be achieved allowing for improve assay and/or diagnostic run-time, output, sensitivity, as well as loser cost due to the inexpensive nature of the components compared to traditional energy supplementation techniques. Each of the above referenced components may further be supplemented over a specified time-course.

Examples of such ATP-dependent application may include, but not be limited to energy-dependent light reactions or enzyme reactions could benefit; Epimerases, Dehydratases, NADPH-Hydrate-Dehydratases, Cellulases, Chromatin-remodeling-enzymes, ATP-dependent peptide ligases, DNA ligation, and traditional cell-free expression systems. The inventive system may be applied in the generation of. Synthestases; Phosphorylation processes; CoA dependent enzymes (detergents, flavor industry); Deaminoacide amides (Deala-Deala-Ligases)

As noted above, in one embodiment of the present invention a cell-free expression system having a coupled Adk/PPK energy regeneration system may include the addition of inorganic polyphosphate (PPi). In another embodiment, a cell-free expression system having a coupled Adk/PPK energy regeneration system may include the addition of a first quantity of PPi, while still other embodiments may include the addition of a plurality of quantities of PPi. In this embodiment, a plurality of quantities of PPi may be added at a pre-determined time interval.

In one preferred embodiment, a cell-free expression system having a coupled AdK/PPK energy regeneration system may include a concentration range sufficient to maintain the energy regulation reaction at the approximate state of equilibrium, and/or produce the maximum, or desired level of ATP. In yet another preferred embodiment, a cell-free expression system having a coupled AdK/PPK energy regeneration system may include concentration approximately between 0.1 and 50 mg/m lPPi or higher. In yet another preferred embodiment, a cell-free expression system having a coupled AdK/PPK energy regeneration system may include a concentration range sufficient to maintain the energy regulation reaction at an approximate state of equilibrium, such range being approximately between 0.3-4 mg/mlPPi.

In yet another preferred embodiment, a cell-free expression system having a coupled AdK/PPK energy regeneration system may include a concentration range sufficient to maintain the energy regulation reaction at an approximate state of equilibrium, such range being approximately between 0.2-2 mg/ml PPi. In yet another preferred embodiment, a cell-free expression system having a coupled AdK/PPK energy regeneration system may include a concentration range sufficient to maintain the energy regulation reaction at the approximate state of equilibrium, such range being approximately between 0.5-0.6 mg/ml PPi. Naturally, all such ratios may be scaled up or down as may be required based on the size, duration, and energy requirements of a cell-free expression reaction. In some other embodiments, a functional range may also include no additional PPi, or 0 mg/ml.

Figure 13A:
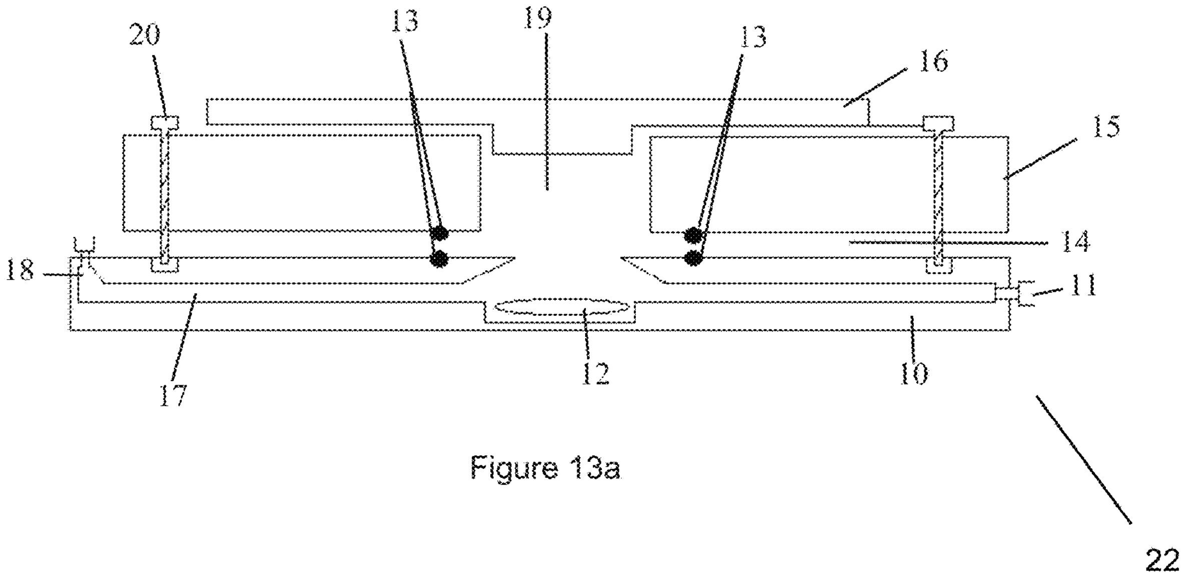
FIG. 13*a-b*: is a cell-free expression bio-reactor for a cell-free expression system in one embodiment thereof.
Figure 13B:
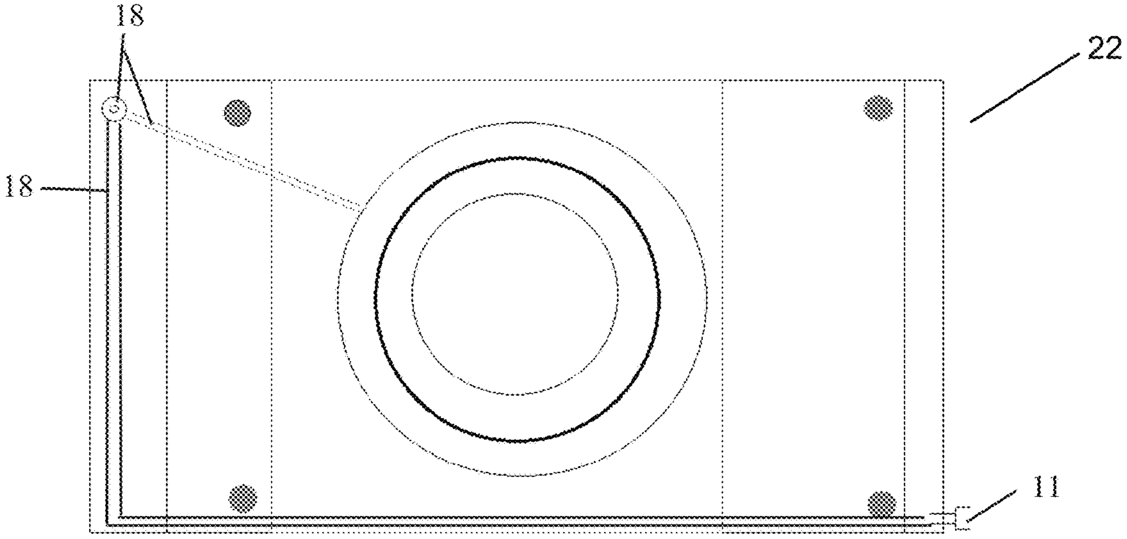

Generally referring to FIGS. 13*a-b*, in one embodiment the invention relates to a cell-free expression bioreactor (22) (see elements 10-20, including a Reactor vessel, a feeding solution reservoir (10) an Inlet (11), a Stir bar (12), a plurality of seals (13), a Dialysis membrane (14), a Reaction vessel (15), a Lid (16), a Feeding solution (17), an Outlet with groove for air bubble removal (18) a Reaction mixture (19), and a plurality of Tighteners (20)). It should be noted that such a bioreactor is exemplary only as multiple cell-free systems may be implemented with this invention. The inventive bio-reactor may allow cell-free expression at higher than traditional temperatures and may be configured to run as a batch, continuous or semi-continuous, from for example a feeder reaction solution.

Figure 14:
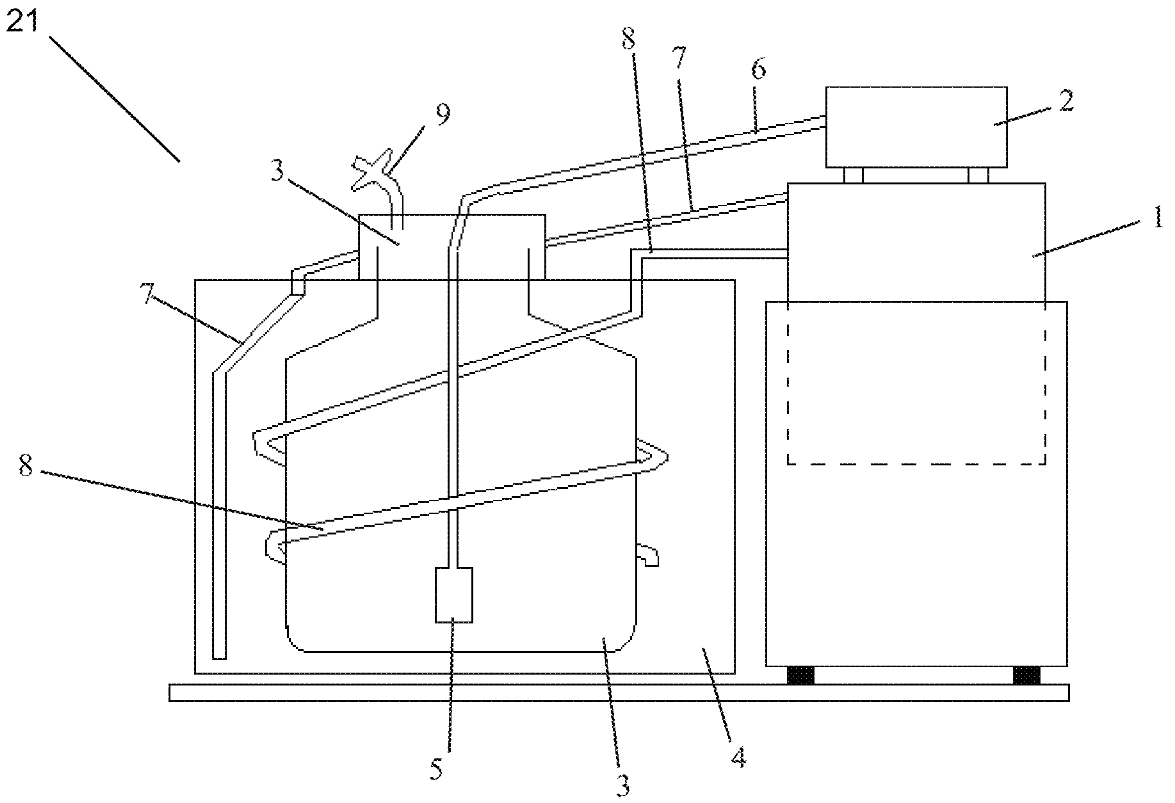
FIG. 14: is a cell culture apparatus for generating cell cultures in one embodiment thereof.
Figure 15:
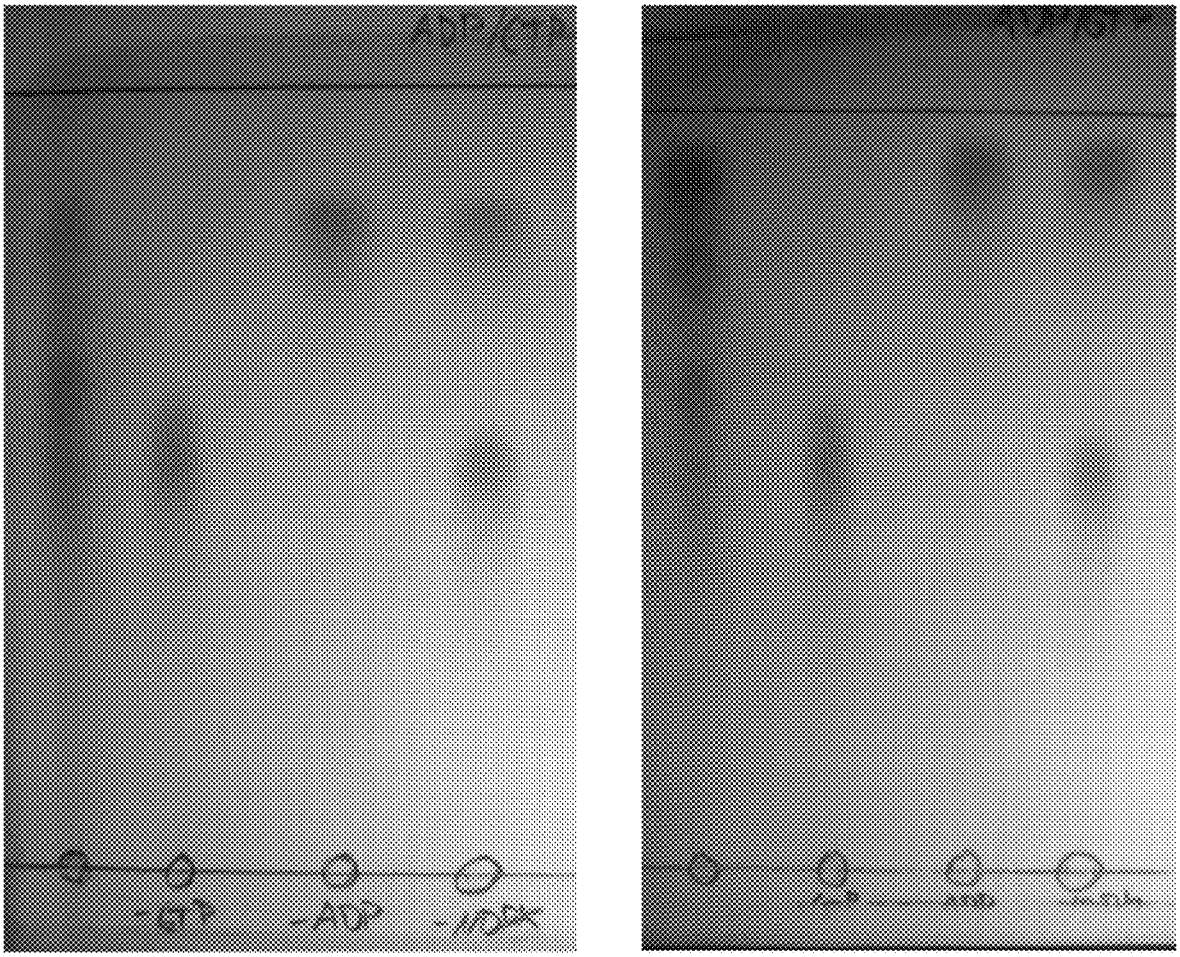
FIG. 15: TLC plates demonstrating use of NDPK. As shown from left to right. us eof NDPK shows formation of an intermediate species, reflective of the ping-pong mechanism of XDP+YTP→XTP+TDP in one embodiment thereof.

Again, referring to FIG. 14, in this embodiment the invention may further include a cell-free culture apparatus (21) (see elements 1-9, including a Recirculation bath (1), and Air compressor; alternate air/gas supply (2), a fermentation vessel (3), and Insulated water bath (4), and Air stone (5), and Air supply line (6), a Water return (7), a Hot water supply (8), and a Sterile filtered air vent (9)). This cell culture apparatus may be configured to culture, in certain preferred embodiment thermophilic bacteria. A fermentation vessel may be removable and separately autoclavable in a preferred embodiment. Additionally, this cell-free culture apparatus (21) may be configured to accommodate the growth of aerobic as well as anaerobic with organisms. Moreover, both the cell-free expression bioreactor (22) and cell-free culture apparatus (21) may accommodate a variety of cell cultures, such a microalgae, plant cells and the like.

It should be noted that the following cell-free protein expression system is exemplary in nature and different configurations and systems may be incorporated with the aforementioned inorganic polyphosphate energy regeneration system. In addition, the novel inorganic polyphosphate energy regeneration system may be adapted to a variety of known cell-free expression systems and may further be configured into an adaptable kit.

Because this invention involves production of genetically altered organisms and involves recombinant DNA techniques, the following definitions are provided to assist in describing this invention. The terms “isolated”, “purified”, or “biologically pure” as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term “purified” denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term “nucleic acid” as used herein refers to a polymer of ribonucleotides or deoxyribonucleotides. Typically, “nucleic acid” polymers occur in either single- or doublestranded form but are also known to form structures comprising three or more strands. The term “nucleic acid” includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein. For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Exemplary conservative amino acid substitutions are known by those of ordinary skill in the art. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

Homology (e.g., percent homology, sequence identity+sequence similarity) can be determined using any homology comparison software computing a pairwise sequence alignment. As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff JG. [Amino acid substitution matrices from protein blocks. Proc. Natl. Acad. Sci. U.S.A. 1992, 89(22): 10915-9], According to a specific embodiment, the homolog sequences are at least 60%, 65%, 70%, 75%, 80%, 85%, 90%, 95%, 99% or even identical to the sequences (nucleic acid or amino acid sequences) provided herein. Homolog sequences of SEQ ID Nos 1-22 of between 50%-99% may be included in certain embodiments of the present invention.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid but must be sufficiently complementary to hybridize with the template. The design of suitable primers for the amplification of a given target sequence is well known in the art and described in the literature cited herein.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "reaction mixture," or "cell-free reaction mixture" as used herein, refers to a solution containing reagents necessary to carry out a given reaction. A cell-free expression system "reaction mixture" or "reaction solution" typically contains a crude or partially-purified extract, (such as from a bacteria, plant cell, microalgae, fungi, or mammalian cell) nucleotide translation template, and a suitable reaction buffer for promoting cell-free protein synthesis from the translation template. In some aspects, the CF reaction mixture can include an exogenous RNA translation template. In other aspects, the CF reaction mixture can include a DNA expression template encoding an open reading frame operably linked to a promoter element for a DNA-dependent RNA polymerase. In these other aspects, the CF reaction mixture can also include a DNA-dependent RNA polymerase to direct transcription of an RNA translation template encoding the open reading frame. In these other aspects, additional NTPs and divalent cation cofactor can be included in the CF reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention. Moreover, those of ordinary skill will understand that some components in a reaction mixture, while utilized in certain embodiments, are not necessary to generate cell-free expression products.

The term "cell-free expression products" may be any biological product produced through a cell-free expression system.

The term "about" or "approximately" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" or "approximately" will depend upon the particular system under study. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The term "recombinant" or "genetically modified" when used with reference, e.g., to a cell, or nucleic acid, protein, or vector, indicates that the cell, organism, nucleic acid, protein or vector, has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed, over-expressed, under-expressed or not expressed at all.

As used herein, the term "transformation" or "genetically modified" refers to the transfer of one or more nucleic acid molecule(s) into a cell. A microorganism is "transformed" or "genetically modified" by a nucleic acid molecule transduced into the bacteria or cell or organism when the nucleic acid molecule becomes stably replicated. As used herein, the term "transformation" or "genetically modified" encompasses all techniques by which a nucleic acid molecule can be introduced into a cell or organism, such as a bacteria.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor or binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "genome" refers to chromosomal DNA found within the nucleus of a cell, and also refers to organelle DNA found within subcellular components of the cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

The term "expression," as used herein, or "expression of a coding sequence" (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term “vector” refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria.

An “expression vector” is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an “expression cassette.” In contrast, as described in the examples herein, a “cassette” is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

The terms “expression product” as it relates to a protein expressed in a cell-free expression system as generally described herein, are used interchangeably and refer generally to any peptide or protein having more than about 5 amino acids. The polypeptides may be homologous to, or may be exogenous, meaning that they are heterologous, i.e., foreign, to the organism from which the cell-free extract is derived, such as a human protein, plant protein, viral protein, yeast protein, etc., produced in the cell-free extract.

A “cell-free extract” or “lysate” may be derived from a variety of organisms and/or cells, including bacteria, thermophilic bacteria, thermotolerant bacteria, archaea, firmicutes, fungi, algae, microalgae, plant cell cultures, and plant suspension cultures.

As used herein the singular forms “a”, “and”, and “the” include plural referents unless the context clearly dictates otherwise. Thus, for example, reference to “a cell” includes a plurality of such cells and reference to “the culture” includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Generation of Thermostable Gst RNAP from *G. stearothermophilus*

In this preferred embodiment, the present inventors have demonstrated that RNA polymerase from *G. stearothermophilus* (Gst RNAP) may be cloned from genomic DNA (gDNA) isolated from a *G. stearothermophilus* culture. In this embodiment, approximately 20 ml *G. stearothermophilus* may be grown in an overnight culture and then pelleted, for example with a centrifuge. The gDNA may then be isolated, in this instance by using commercially available gDNA purification kits, such as a Macherey-Nagel NuceloSpin Microbial DNA Kit. The gDNA may then be concentrated using ethanol precipitation. This may generally be accomplished by adding a salt and ethanol to a solution containing the gDNA which may precipitate the gDNA which may again be pelleted for example with a centrifuge and then resuspended in DNase-/RNase-free water.

In this preferred embodiment, the subunits of the Gst RNAP may be cloned using specific primers which may be designed based on the nucleotide sequences of each gene. Forward and reverse primers that contain specific restriction sites to introduce the subunit genes into an expression vector may be utilized. In one preferred embodiment, forward and reverse primers that contain restriction sites to specifically introduce the subunit genes into an IBA StarGate Expression Vector(s) may be generated. Next the subject primers and gDNA may be subject to a polymerase chain reaction (PCR) to amplify the Gst RNAP subunit genes. In one preferred embodiment PCRs may be performed using standard MasterMix reactions and 50 ng of input gDNA isolated from *G. stearothermophilus.*

As noted above, it may be preferred to select a Gst RNAP subunit to act as an optimized gene sequence, perhaps due to the presence of in internal restriction site. Generally referring to FIG. 3, Gst RNAP subunit beta' (opt) (SEQ ID NO. 4) may be identified and cloned in a manner similar to that described above. Also referring to FIG. 3, a transcription factor, in this case RpoD (SEQ ID NO. 7), may be used from a commercially available codon optimized gene synthesis (Invitrogen) and cloned directly into an expression vector.

In one embodiment, the Gst RNAP subunit DNA sequences that have been amplified through the PCR process may be isolated. In one preferred embodiment, PCR reactions may be analyzed on 1% Ethidium Bromide agarose gels and the subunit fragments may be isolated by agarose gel extraction and/or PCR purification methods known within the industry such as Macherey-Nagel NucleoSpin Gel and PCR Clean-up. These gene fragments may then be inserted into an appropriate delivery vector. For example, in one embodiment, the previously generated gene fragments and a selected vector, in this embodiment a commercially available StarGate vector (see e.g. FIG. 2), may be digested with selected restriction enzyme(s) and ligated through, for example, a 3:1 T4 DNA ligase reaction which may be available commercially as a Thermo Fisher Scientific Rapid DNA Ligation Kit.

Next, in this embodiment the ligated gene fragments and plasmid vector may be transformed into a selected bacterial strain. In a preferred embodiment the ligated vector(s) may be transformed into the bacteria *Escherichia coli*, in particular Top10 competent *E. coli* that may be configured to have a high rate of transformation efficiency. In this embodiment, Top10 competent *E. coli* may include mutations in the recA gene which may reduce DNA recombination promoting plasmid vector stability and may further include an endA gene knockout which may reduce non-specific endonuclease activity improving plasmid vector yield and quality.

Successfully transformed bacteria may be identified, for example, through positive gene detection PCR, or other known methods, and may then be subsequently cultured to generate multiple copies of the plasmid vector within the growing bacterial colony. In a preferred embodiment, the plasmid vector DNA may be isolated and sub-transformed into another select bacterial strain. In a preferred embodiment, the prepared plasmid vector DNA may be sub-transformed into a high expression strain of *E. coli*, such as BL21(DE3) for optimal protein expression.

In one embodiment, one or more expressed RNAP subunit proteins may be configured with a molecular tag. Referring now to FIG. 3, the RNAP beta' (opt) subunit may be configured to contain a poly-His or His-6 tag, which may be used later for protein purification. In this embodiment, the expressed His-tagged RNAP beta' (opt) subunit can be purified and detected easily because the string of histidine residues binds to several types of immobilized metal ions, including nickel, cobalt and copper, under appropriate buffer conditions.

In one embodiment, a tagged Gst RNAP may be expressed and purified. In this preferred embodiment, the His-6 tagged beta' (opt) subunit may be expressed in a BL21(DE3) strain of *E. coli*. In this embodiment, the BL21 (DE3) strain of *E. coli* may be cultured in NYZ medium, which among other things, may lack lactose that may induce certain proteases that could potentially degrade any expressed proteins, reducing overall yields. Protein expression may be induced at a certain optical density (OD) of bacterial growth. In a preferred embodiment, at OD 0.7, protein expression may be induced by the addition of 0.25 mM isopropyl β-D-1-thiogalactopyranoside (IPTG) for 6-8 hours at 30-32° C. IPTG is a molecular reagent that mimics allolactose, a lactose metabolite that triggers transcription of a lac operon in the plasmid vector DNA, thereby inducing protein expression of the Gst RNAP subunit gene under the control of a lac operator (see FIG. 2*a*).

In this preferred embodiment the BL21(DE3) cultures may be lysed and a lysate prepared and passed through a metal ion-charged resin. This lysate may pass through a Ni-charged IMAC resin, where the His-6 tag on the beta' (opt) subunit may bind to the immobilized nickel ion on the resin. Non-binding and non-specific binding proteins may further be removed in this embodiment through the addition of 5 mM Imidazole, while the beta' (opt) subunit remains bound to the resin.

Figure 7:
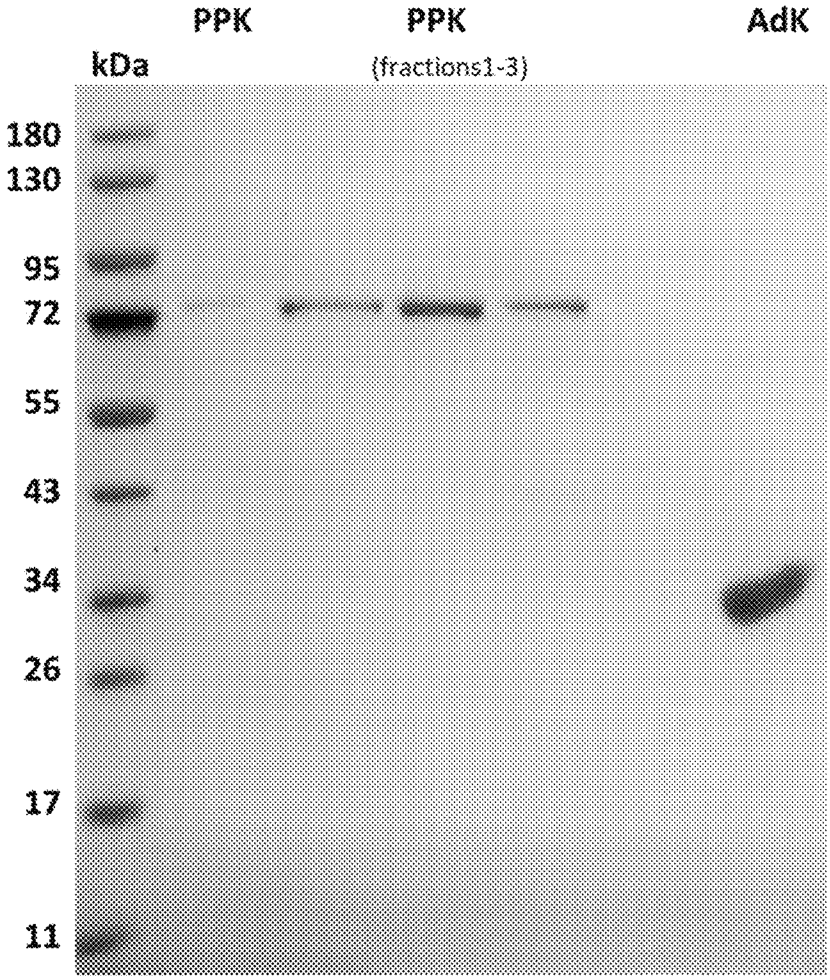
FIG. 7: demonstrating the isolation and purification of recombinant proteins Gst AdK and TaqPPK.

Next, expression and isolation of the remaining Gst RNAP subunits may occur. In a preferred embodiment, a combined lysate of protein expression strains for the remaining Gst RNAP subunits may be prepared and incubated with beta' (opt)-loaded resin for approximately 2-3 hours. Non-binding and non-specific binding proteins may again be removed through the addition of 5 mM Imidazole. The expressed subunits may assemble to form a RNAP complex bound to the resin through the beta' (opt) subunit, and the assembled Gst RNAP may then be eluted by the addition of 300 mM Imidazole or other known methods. The assembly of the Gst RNAP may be demonstrated by SDS-PAGE and further stored in in vitro transcription/translation compatible buffer conditions at a concentration of 10 mg/ml at −20° C. for later use. Further, protein activity assays may be performed to verify assembly and functionality of the GSt RNAP complex. The presence of mRNA transcripts being indicative of successful Gst RNAP isolation and assembly. In one embodiment, a 25 μl assay may be performed comprising:

4 mM each ribonuclease tri-phosphate (rNTP);
250 ng DNA;
2 μl Gst RNAP;
20 U RNase inhibitor; and
5 μl 5× reaction buffer Example 2: Gst AdK/TagPPK Isolation and Purification The present inventors demonstrated the isolation and purification of Gst AdK and TaqPPK, which purified proteins were utilized in subsequent assays as described below. Specifically, Gst AdK and TaqPPK were expressed and isolated utilizing the methods as generally described herein. Referring to FIG. 7, the purified, recombinant proteins were analyzed on a 4-20% SDS PAGE. The gel being stained with coomassie dye.

Specifically, aliquots of the purified proteins were analyzed on SDS PAGE for purity and correct size. A previously test-purified PPK protein (PPK) was used as an additional size marker for the lot purification of the recombinant TaqPPK (PPK fractions 1-3). All fractions eluted from the purification column are demonstrated as pure and show the correct size of around 74 kDa. The purified Gst AdK shows no contaminant proteins and has the correct size of around 25 kDa.

Example 3: Coupled AdK/PPK ATP Energy Regeneration

The present inventors demonstrated the coupled AdK/PPK ATP regeneration capability of the invention through a commercially available ATP determination assay. Here, the present inventors employed Life technologies, D-Luciferin, A22066 to verify functionality of the Gst AdK and/or PPK proteins, (in this embodiment derived from *E. coli*), in ATP regeneration.

In this embodiment, in addition to the standard 200 μl assay components, the following materials may be added to the assay, with the results being provided in FIGS. 4-6.

i) 10 μM ATP
ii) 5 μl Gst AdK
iii) 5 μl PPK derived from *E. coli* (exemplary only)
iv) 50 μl polyphosphate (1 mg/ml stock solution)

As demonstrated in FIGS. 4-6, these data generally demonstrate the enhanced ATP regeneration capabilities of the invention's AdK/PPK-PPi ATP energy regeneration system, and its improvement over ATP alone, as well as traditional PEP/PK energy supplementation. Specifically, the data clearly separate: lowest: ATP, middle: PEP/PK, and upper: AdK/PPK-PPi Example 4: AdK/PPK Energy Regeneration at Variable Polyphosphate Concentrations The present inventors demonstrated coupled Gst AdK/TaqPPK energy regeneration may be achieved at variable polyphosphate concentrations through a commercially available ATP determination assay. Specifically, a standard reaction setup was varied in the amount of added PPi. The luciferase signal (RLU) was measured over time (min).

As demonstrated in FIG. 8, one concentration range that maintained the equilibrium of the reaction was determined to be between approximately 0.2-2 mg/ml PPi. Other concentration ranges were determined to maintain the equilibrium of the reaction. Specifically, such ranges were determined to be between 0.1-4 mg/ml PPi, and/or 0.5-0.6 mg/ml, and/or 0.1-7 mg/ml. As demonstrated in FIG. 8, some additional ATP regeneration was found within the functional ranges, including, but not limited to approximately 0-48 mg/ml and higher.

In one embodiment, a standard reaction setup for 100 μl luciferase assay may include:

| | standard | final conc. |
|---|---|---|
| 20× buffer | 5 | 1× |
| 100 mM DTT | 1 | 1 mM DTT |
| 3 mg/mL D-luciferin | 5 | 150 μg/ml luciferin |
| 5 mg/mL luciferase | 0.2 | 10 mg/ml luciferase |
| 25 mM AMP | 10 | 2.5 mM AMP |
| 0.34 mg/ml TaqPPK | 67 | 228 μg/ml PPK |
| 13 mg/ml Gst AdK | 0.2 | .226 mg/ml AdK |
| 100 mg/ml Sodium polyphosphate | 0.5 | 0.5 mg/ml |
| dH2O | 11.1 | |
| TOTAL | 100 | |

Again, as demonstrated in FIG. 8, ATP regeneration was sustained for more than five hours, at which point the measurements were stopped. As shown, the present inventors demonstrate that higher or lower inputs of PPi may disturb a stable reaction cycle of Gst AdK/TaqPPK and, while functional, do not result in the highest levels of continuous energy regeneration. Naturally such ranges are approximations and not intended to be limiting.

Example 5: Decoupled AdK/PPK ATP Energy Regeneration Out of AMP/PPi

The present inventors demonstrated that the Gst AdK/TaqPPK system can generate energy (ATP) out of inexpensive materials, such as PPi and AMP as a source. To further confirm this novel ATP regeneration system, the present inventors decoupled the reaction of Gst AdK/TaqPPK from the luciferase assay. Specifically, the present inventors first generated ATP from AMP/PPi using purified Gst AdK and TaqPPK ATP proteins, purified the reactions and used samples to run a luciferase assay—which as noted above, requires ATP to emit light.

Figure 9:
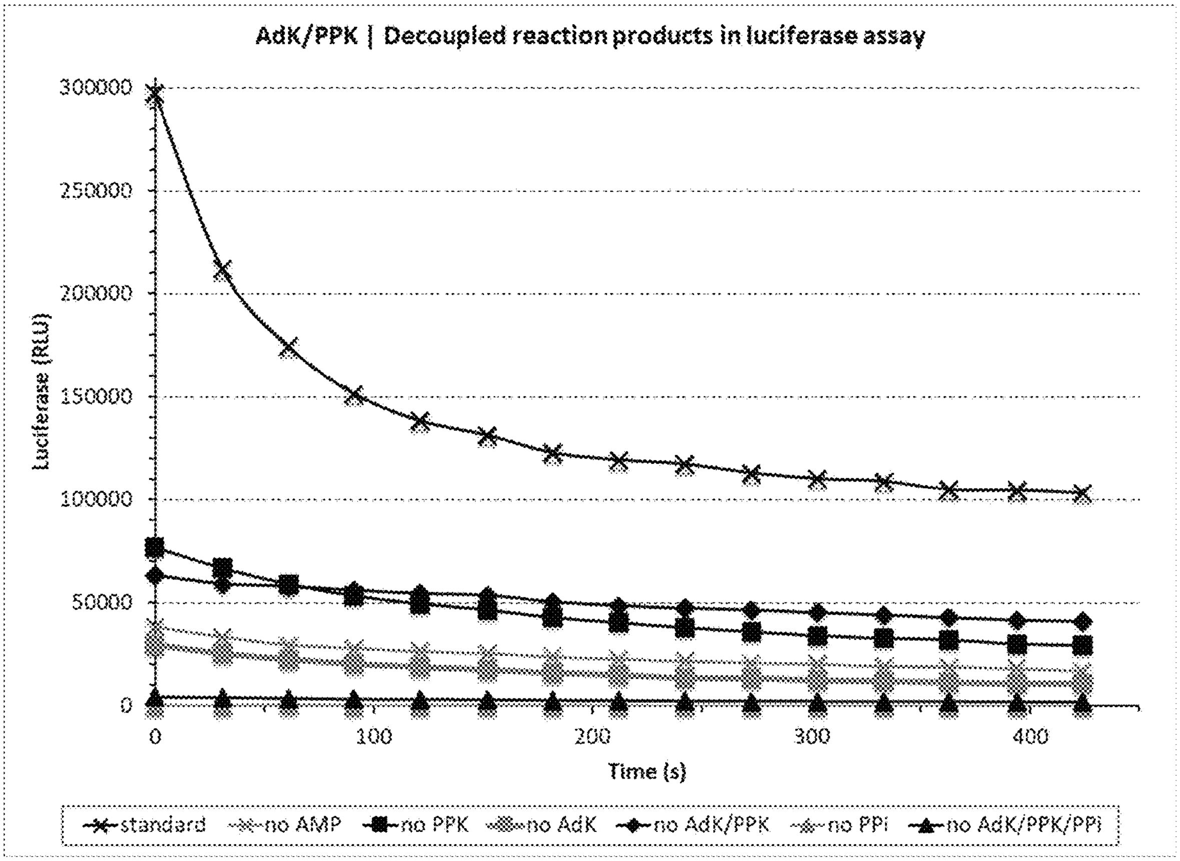
FIG. 9: luciferase assay showing decoupled ATP energy generation reaction products.

As shown in FIG. 9, the present inventors show that only a standard setup with all reaction components provided sufficient ATP for a luciferase light-emitting reaction. The controls which had individual compounds/enzymes or combinations thereof missing, did not provide ATP for a successful luciferase reaction. Since the ATP energy was not regenerated in this assay, the luciferase signal drops over time and reaches almost background after around seven minutes at which point all previously generated ATP was used up.

Example 6: Generation of ATP Energy Out of AMP/PPi and its Regeneration by Gst AdK/TaqPPK The present inventors demonstrated the generation of ATP energy out of AMP and PPI and that the ATP regeneration, through at least one embodiment of the Gst AdK/TaqPPK energy regeneration system. Specifically, the present inventors performed a luciferase assay, replacing the usually needed ATP by AMP and added the energy regeneration system components, namely Gst AdK, TaqPPK, and PPi). In control experiments, the present inventors omitted each component and combinations thereof.

Figure 10:
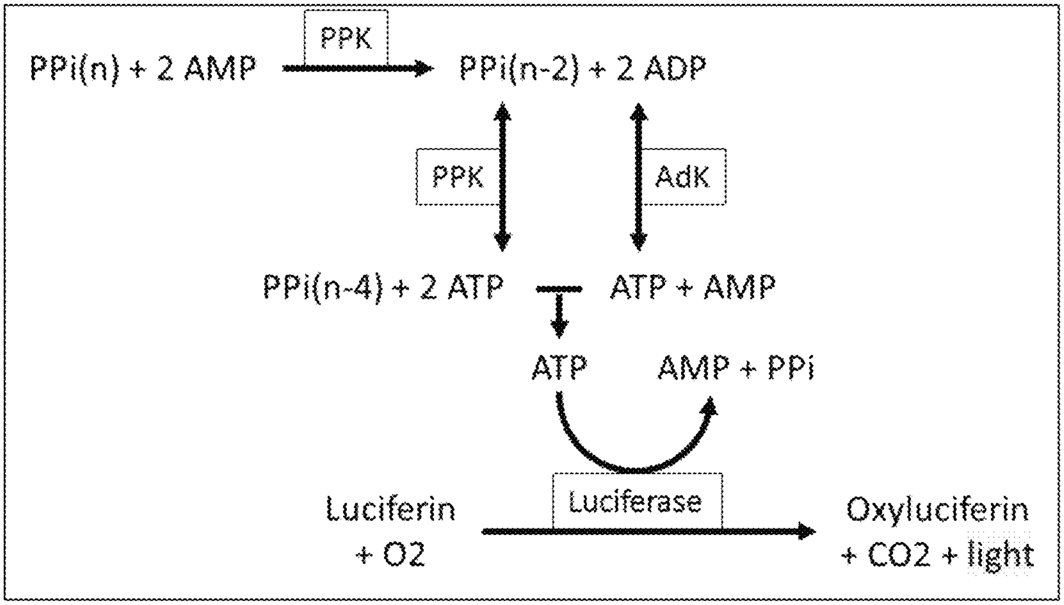
FIG. 10: general reaction scheme of the Gst AdK/TaqPPK ATP energy regeneration system as employed in a luciferase assay.

The reaction scheme of the Gst AdK/TaqPPK ATP energy regeneration system, in the context of an ATP-using luciferase reaction to emit light, is generally demonstrated in FIG. 10. In a first step, ADP is generated in an irreversible reaction by PPK using AMP and PPi as a source. ADP can be converted into ATP by PPK and AdK, both in reversible reactions keeping the amounts of AMP, ADP and ATP balanced. ATP is then used by luciferase to convert luciferin and emit light.

Figure 11:
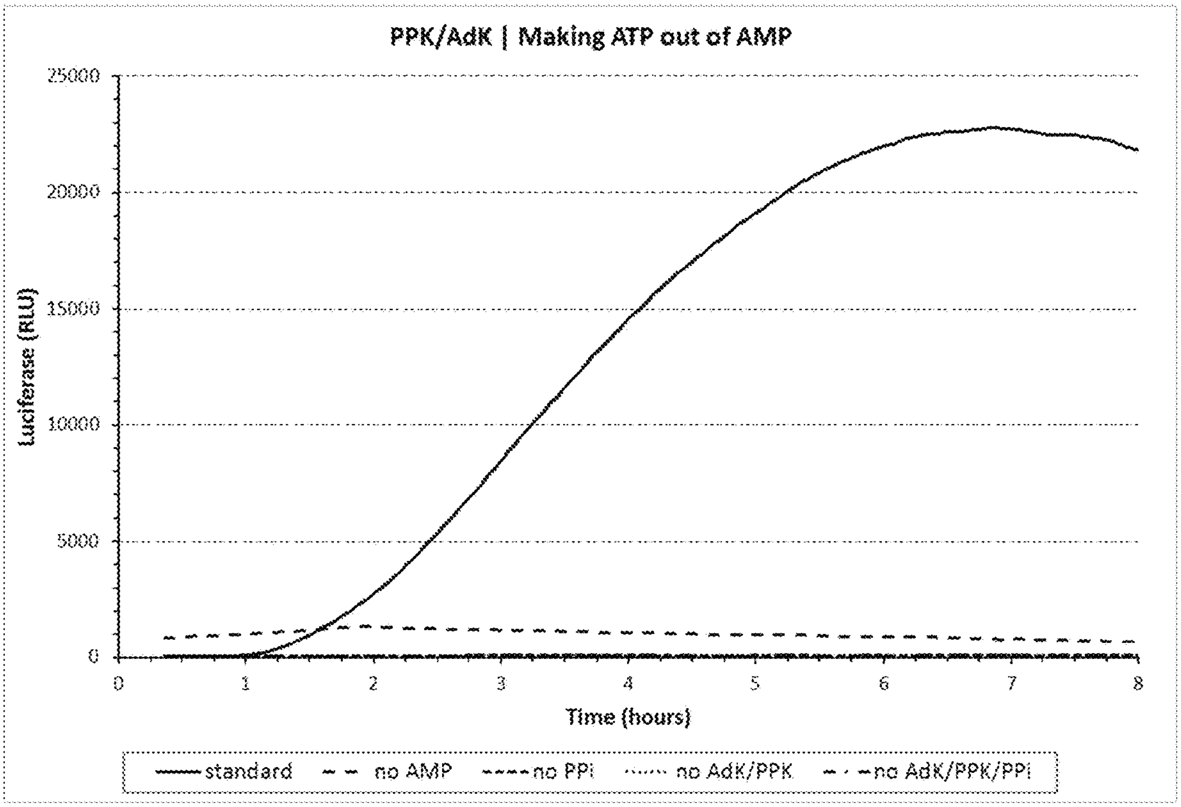
FIG. 11: synergistic Gst AdK and TaqPPK enzymes generating ATP energy out of inorganic polyphosphate and AMP as a substrate source.

As shown in FIG. 11, the standard energy regeneration system components showed an increasing luciferase signal (RLU) after enough ATP is made to support the light emitting reaction. The signal increases over time until it reaches a maximum after around 7 hours. Control reactions with the energy regeneration system missing do not show any RLU. A such, the present inventors demonstrate that it is the coupled, or synergistic Gst AdK and TaqPPK enzymes generating energy (ATP) out of inexpensive polyphosphate and AMP as a substrate source. The present inventors were able to measure a light emitting reaction for approximately 20 hours (not shown), further demonstrating the robust energy regeneration possible from their novel system.

Example 7: Cell-Free Extract Preparation

A defined, non-toxic, non-hazardous medium based on genetically modified organism-free (GMO-free), purified soy peptone and animal-sourced materials free (ASM-free) casein tryptone was developed by the present inventors for fermentation of the genetically modified *Geobacillus* strains. This medium does not require the addition of potentially toxic metal salts or metal ion chelators, (e.g., Trinitrileacetic acid, etc.), for a productive fermentation of the genetically modified *Geobacillus* strains. The fermentation temperature range may be set and kept stable at approximately 52-55° C., although larger temperature ranges are also contemplated and enabled. The culture may be maintained at an approximate pH of 7.2-7.6, although larger pH ranges are also contemplated and enabled. The addition of 10 mM of HEPES buffer, may be added as needed. Non-toxic, silicone-based anti-foaming agents may be added, as needed, for a controlled fermentation process.

Ribosomal RNA (rRNA) was isolated from growing cultures at different stages of the fermentation process and their concentration determined as a measure of ribosome concentration per culture unit. A maximum concentration of rRNA was observed after 6-7 hours of growth in fresh media. In some embodiments, cultures may be grown in multiple phases with increasing volumes, and the final 7.5 L. culture is inoculated to $OD_{600}$ 0.5 and grown for 6-8 hours to a final $OD_{600}$ of 2.5-2.8 at 52-55° C. and pH 7.2-7.6.

The lysate is prepared after a single freeze/thaw cycle overnight at −80° C. from collected washed cells (3×). After the freeze/thaw cycle, the cells are re-suspended in a HEPES buffer saline buffer containing RNase and protease inhibitors (1.25:1 cells to buffer ratio) and are disrupted by ultrasound at 2-4° C. using an established protocol for less than 5 mins (10 sec "on", 30 sec "off" cycling). The used lysis buffer, CF-L1, is non-toxic, non-hazardous. Particulates are removed from the lysate by centrifugation (12,000 g, 4° C., 10 mins), and dialyzed against a non-toxic storage buffer, CF-St, which is similar in composition to the reaction buffer CF-1 but does contain 20% v/v glycerol and no protease inhibitors. A 30-minute run-off reaction (shaking in a closed tube at 250 rpm and at 30° C.) and additional centrifugation (same conditions) to further clarify the extract, is not usually required. Potential surviving bacteria and/or bacterial and fungal contaminations are determined by streaking samples of the lysate and of the pelleted debris on agar plates of mLB/CS-medium, NB, ISP2, blood-brain agar and are incubated at 30° C. and 55° C. for two days. The cell disruption rate is consistently above 99.95% (<1 survivor per 200 μL of resuspended debris and <1 colony forming unit (CFU) per mL of lysate). In one embodiment, processing of a 7.5 L fermenter may produce approximately 30 ml of extract. Naturally, based on the operator's desire and/or need, these amounts/volumes may be scaled up and/or down accordingly.

Total RNA extractions of cleared lysates may be used to determine the ribosome concentration. The total protein concentration of the lysate is determined by UV/Vis spectroscopy and is consistently in the range of 150-160 mg/mL. Aliquots of the lysate are stored at −80° C. and may be stable for 6 months or longer, as demonstrated by determining the stability of the extract (no precipitation) and consistent in vitro transcription/translation rates of a Cas9-sfGFP construct (determined by UV/Vis absorption and fluorescence measurements). The lysate and in vitro transcription/translation reactions may be maintained in an approximate range of pH 7.8-8.0. The salt concentrations for the CF reaction conditions may be variable. Each lysate batch may be evaluated by the in vitro transcription/translation activity of a Cas9-sfGFP linear construct (production of a larger protein with consistent folding) and of a luciferase construct (enzymatic activity).

Example 8: Cell-Free Extracts Generated Utilizing Genetically Modified *Geobacillus* Strains As noted above, the present inventors observed that the over-expression of the sigma factor RpoD (from *Geobacillus*) up-regulated the bacterial RNA polymerase (RNAP) in bacterial cultures of *E. coli* and *Geobacillus*. Recombinant genetic constructs were generated to constitutively express $RpoD_x$, an engineered version, in Geobacilli. The functional reliability of the genetic construct and the protein expression levels were determined and are monitored using a sfGFP construct transformed into the same *Geobacillus* strain and are monitored by 510 nm fluorescence readings of prepared lysates.

The present inventors further utilized the RhIII promoter for in vitro transcription together with the bacterial RNAP. A recombinant modified RhIII promoter for tighter RpoD/promoter recognition may be utilized in some embodiments. Alternatively, a T7 promoter can be used, if, for example, a T7 RNAP polymerase is added to the CF reaction. In some embodiments, a proprietary genetically modified T7 RNAP (T7x) having one or more single point mutations compared to the native RNAP from bacteriophage T7 may be utilized. Such point mutations may allow a faster melting of the double stranded DNA and increase the complex stability of the RNAP with the single stranded template DNA. In this embodiment, a T7x may cause significantly fewer incomplete transcripts and produce consistently higher mRNA concentrations compared to commercial T7-RNAP. The present inventors have demonstrated that both RNAPs perform reliably, with reproducible and predictable results, for constructs up to 45,000 bases in length.

Example 9: In Vitro Cell-Free Expression System Having Novel ATP Energy Regeneration System As detailed above, the invention relates, in certain embodiments to a cell-free expression system where the cellular energy source, ATP, is regenerated from inorganic polyphosphate using a dual enzyme system. One enzyme for the system was developed utilizing a thermostable polyphosphate kinase (PPK) from *Thermophilus aquaticus* (TaqPPK), after demonstrating that a polyphosphate hydrolyzing activity was observed for a homologue enzyme cloned and produced from *E. coli* (ecPPK or PPK). Other than the reported PPK activity, isolated from *Vibrio cholerae*, TaqPPK and ecPPK preferably generate ADP from AMP and the hydrolysed inorganic polyphosphates ($iPP_i$). For the second enzymatic step, two molecules of ADP are then rearranged by a thermostable Adenosine Kinase (AdK) to form one unit of ATP and AMP.

This system has proven to operate effectively for at least 32 hours, as determined by measurements of luciferin luminescence after adding luciferase to a solution of 10 nM AMP, 150 μg/ml luciferin, 1 mg/ml $iPP_1$ and catalytic amounts of the enzymes. A total enzyme turnover number was determined for the Gst AdK/TaqPPK pair of at least 300. This enzymatic loop may remain active for at least 72 hours and up to at least 1 week or longer. In one embodiment, the ATP concentration in the feeding solution may be maintained at a stable 1.5 mM ATP. The present inventors have further demonstrated that TaqPPK may have a maximum total turnover number of approximately 3,000, hence, allowing the further reduction of the protein concentration of TaqPPK in the inventive cell-free expression system. This may prevent or minimize random hydrolysis of polyphosphate, which causes a feedback inhibition by accumulating pyrophosphate to the cell-free reactions, while producing/maintaining the desired levels of ATP.

Such novel energy regeneration characteristics are important, as current *E. coli*-based cell-free systems primarily rely on creatine phosphate/creatine kinase or on phosphoenolpyruvate (PEP) and Pyruvate Kinase (PK) as the main energy regenerating system, though it is established that PK has a total turnover number in the low single digits and the side-product pyruvate is an inhibitor of the translation reaction. In this manner, not only does the current invention teach away from such traditional cell-free expression systems, but indeed, represents a demonstrable improvement that traditional cell-free expression systems known in the art.

The redox potential of the present inventor's cell-free expression system may be stabilized by a Sorbitol-dehydrogenase (SDH). In one embodiment, this SDH may be thermostable (tSDH) (such t designation being applicable generally to other molecules referenced herein). Enzymatic assays using the 340 nm absorption for NADH with purified protein samples demonstrated that the forward conversation from sorbitol and NAD/NAD(P) to fructose and NADH/NAD(P)H is 8 times faster compared to the back reaction. The present inventors cloned and produced this genetically modified thermostable enzyme from *Geobacillus stearothermophilus*, which was also optimized for expression in *E. coli* as previously described here (Gst SDH), which may be added to the feeding solution along with 200 mM sorbitol. The reaction product also provides an additional energy resource via glycolysis and does not accumulate in the reaction mix.

In certain embodiments, the cell-free expression system may include an initial volume of 5 ml for the cell-free reaction volume, and 80 ml for the feeding solution to ensure a continuous exchange and homogeneous reaction conditions in the vessels. Cell-free expression systems between 0.5 ml and 2 liter reaction volumes and higher may further be contemplated.

Example 10: Cell-Free Expression System Reaction Set Up

In one embodiment, the CF system may be adjusted and stabilized in the range of pH 7.9-8.0 with a TRIS-acetate buffer (CF-1) in the feeding and reaction compartments. The final concentration of the lysate in the reaction vessel may be between 100-110 mg/ml total protein, while template DNA (alternatively also together as a pre-run RNA/RNAP reaction) are added together with cofactors, amino acids and nucleotides to the lysate. The feeding solution contains equal concentrations of the nucleotides and all natural amino acids. Cofactors, sorbitol and the aforementioned enzymes are added as well. A detailed list of materials is provided below and may generally be referred to as cell-free reaction components. Additionally, the general components of the dual-enzyme ATP regeneration system may be included. Such components in one preferred embodiment may include but are not limited to, a quantity of Gst AdK, a quantity TaqPPK, and/or a quantity of PPi, and/or a quantity of AMP. Additional embodiments may include a quantity of Gst SDH and sorbitol.

This exemplary cell-free reaction may run in an incubator at approximately 35-37° C., while the reactor is agitated at approximately ~300 rpm for 16 hours. In certain embodiments, this reaction setup or reaction mixture of the combined in vitro transcription/translation reactions may be suitable to produce the target protein for more than 3 days. In one exemplary embodiment, the inventive cell-free expression system may provide the stability to produce proteins for more than 36 hours.

In on specific embodiment, cell-free reaction components may include, but not be limited to:

amino acids
polyphosphate
Tris-Acetate
$Mg(OAc)_2$
$K^+$-glutamate
amino-acetate
NaCl
KCl
$MgCl_2$
DTT
octyl-b-glycoside
NAD (converted to NADH in the system)
NADP (converted to NADPH in the system)
sorbitol
FADH (regenerated by NADH/FADH cellular processes)
ATP
GTP, UTP, CTP each
CoA
PLP
SAM In one specific embodiment, cell-free reaction components may include, but not be limited to:

2 mM of each natural amino acid
1 mg/ml polyphosphate
5 mM Tris-Acetate
4 mM $Mg(OAc)_2$
12 mM $K^+$-glutamate
1 mM amino-acetate
100 mM NaCl
10 mM KCl
5 mM $MgCl_2$
0.1 mM DTT
0.2% octyl-b-glycoside
0.8 mM NAD (converted to NADH in the system)
0.4 mM NADP (converted to NADPH in the system)
200 mM sorbitol
0.5 mM FADH (regenerated by NADH/FADH cellular processes)
1.5 mM ATP
1 mM GTP, UTP, CTP each
1 mM CoA
2 mM PLP
0.2 mM SAM All amounts, concentrations, volumes and ratios of any cell-free reaction component are exemplary only, as they may be variable based on reaction volume, duration, or expression product to be produced, and other variables. Cell-free reaction components may further include, but not be limited to, all other components necessary for transcription/translation mechanism, amino acids, nucleotides, metabolic components which provide energy and which are necessary for the synthesis, whether provided by the cell extract, and or added to the cell-extract. Cell-free reaction components may further include a quantity of tRNA specific for the strain of bacteria, algae, microalgae archaea, fungi and/or firmicute that may be employed. For example, in this embodiment described above, natural *Geobacillus* tRNAs may be added. Additionally, cell-free reaction components may further include a quality of tRNA that may overcome stalling of translation due to rare codons. For example, in some embodiments, tRNAs from *E. coli* mre600 may be included in the cell-free reaction to overcome stalling of translation due to rare codons.

Example 11: High-Efficiency Generation of *Clostridium tetani* E88 Tentoxilysin by In Vitro Cell-Free Expression The present inventors demonstrate, as an exemplary embodiment, the in vitro expression of Tentoxilysin (tetanus neurotoxin) utilizing at least one embodiment of the inventive cell-free expression system that utilizes a coupled Gst AdK/TaqPPK ATP energy regeneration as generally described herein.

Tentoxilysin (TetNT) is naturally produced as a 150 kDa single chain protoprotein. TetNT coordinates with a $Zn^{2+}$ cation at the endopeptidase motif, $M_{232}HELIHVL_{239}$, which enables the proteolytic cleavage of the full-length polypeptide between $A_{457}$ and $S_{458}$. The selective oxidation of two Cysteine residues ($C_{439}$ and $C_{467}$) forms a disulfide bridge between both chains and allows the formation of the active tetanus toxin protein complex consistent of a short chain, $M_1$-$A_{457}$, and a long chain, $S_{458}$-$A_{1319}$. This protein is then selectively exported by the natural producing strains of the *Cl. tetani* family.

TetNT is an internalizing $Zn^{2+}$-dependent endopeptidase, which hydrolyzes Synaptobrevin-2 between $Gln_{76}$ and $Phe_{77}$ via a toxin/ganglioside receptor complex formation. The hydrolysis of the Synaptobrevin-2 receptors on synaptic vesicles prevents the release of the inhibitory neurotransmitter gamma-aminobutyric acid (GABA) into the synaptic cleft. This ultimately causes rigid muscular spasms, besides other symptoms, of the patient described as Tetanus. The tetX gene was localized in the *Cl. tetani* E88 genome and was previously further encoded on the *E. coli* protein expression plasmid CTC_p60. The gene product was previously cloned and expressed, as a heterologous protein to confirm the protein activity and to conduct high-resolution structural protein studies. A potential N-acetyl-b-neuraminic acid modifying activity of TetNT was previously described and known in the art as well.

According to FDA regulations, currently tetX toxoid, suitable for human vaccination, is derived from active *Cl. tetani* culture. The completely folded and exported toxin is removed from the active culture by flocculation resulting from the addition of aluminum sulfate and ammonium sulfate. The extracted toxin is subsequently inactivated by the addition of formaldehyde to gain toxoid suitable for vaccinations. FDA suggests quality control measures in the form of SDS-PAGE, FPLC or HPLC profiles and purifications, which are currently not required.

The established isolation and preparation protocol currently known in the art carries risks. These risks have been acknowledged by the FDA, as the agency recommends tetanus vaccinations for children of 7 years of age and older, and adults only. The vaccination carries a 5% risk of infections with *Cl. tetani*. The biggest challenges for fermentation-based production of Tet toxoid are the control of formaldehyde concentrations to ensure the complete deactivation of the toxin and the control of the toxoid concentration in the final product resulting in 40% of all vaccinations being ineffective.

As an exemplary embodiment, these challenges and the production limitations can be addressed by replacing the fermentation process with the inventive in vitro transcription/translation based production method. The carry-over of spores and any other colony formers is not existent and ensures full sterility of the Active Pharmaceutical Ingredient (API). The total protein concentration is monitored during the whole process and the final product may be controlled by standard laboratory methods.

The present inventors generated a genetic construct for TetNT expression. In this embodiment, the genetic construct was designed for gene synthesis and, specifically, to be fed into the in vitro transcription/translation, or cell-free expression reaction as a linear PCR template. The use of linear DNA in the present cell-free expression system may be preferable in some embodiments as it cannot be transferred, as it is unable to recombine, replicate or be transfected. The linear genetic construct may include the following basic configuration: ((promoter)-(RBS)–(start)(expression product cleavage site-detection tag+purification tag)(stop). In one specific embodiment, this configuration may include: (promoter)-(RBS)–(start)(TetNT TEV mCherry H6)(stop).

In this embodiment, the promoter may include: a RhIII promotor sequence (SEQ ID NO. 18), or alternatively a T7 promotor sequence (SEQ ID NO. 19). An RBS (ribosomal binding site) may be derived from a T7 gene phage consistent with *Geobacillus* sequences (SEQ ID NO. 20) (naturally a number of promotors may be utilized apart from these exemplary examples). A recombinant TetNT gene may include SEQ ID NO. 21. In this recombinant TetNT gene, the stop sequence is removed. Finally, a TEVsite, mCherry, His6 may include SEQ ID NO. 22, again, with the stop removed from the mCherry. As should be noted, while provided as separate sequences, the genetic construct may be presented as a single linear PCR fragment of DNA generally described.

In this instance, due to safety and security concerns, the DNA coding for the full-length tetanus toxin, in a preferred embodiment, gene synthesis may proceed as two separate circular constructs, which will be recombined in the laboratory to a single plasmid for amplification purposes. For example, a first construct coding for the TetNT light chain (SEQ ID NO. 12) with the autocatalytic protease site (SEQ ID NO. 13) and disulfide bridge forming cysteines. A second construct will code for the TetNT heavy chain (SEQ ID NO. 14), containing the partially integrated TEV site (SEQ ID NO. 15) and mCherry-His6 (SEQ ID NO. 16). While the recombinant protein is presented as individual genetic constructs and amino acids sequences, such sequences may be part of a single construct that ultimately produce a single linear polypeptide (SEQ ID NO. 17), which may correspond to a polynucleotide sequence, as a PCR amplified linear DNA construct. Additional embodiments may include disparate constructs that may form a single linear polypeptide.

The present inventors demonstrate expression of a full-length 150 kDa pro-toxin by cell-free protein synthesis further utilizing the previously described dual enzyme ATP regeneration system. In this specific embodiment, expression of a full-length 150 kDa pro-toxin by cell-free protein synthesis may occur in the 5 ml reactor according to described conditions. The reaction progress may be monitored by daylight fluorescence of tagged mCherry with an excitation wavelength of 587 nm and red-shifted fluorescence. After no further increase in protein concentration is observed, the content of the reaction vessel will be transferred into a 50 ml reaction tube. The reaction times and protein concentrations attained can be determined continuously.

A 10 mM HEPES buffer pH 8.0, containing lactose, 200 mM NaCl, 1 mM DTT, may be added to dilute the reaction mix 10-fold. 1-2 mL of a Ni-IDA resin will be added to this solution and incubated at approximately 20-25° C. for 1 hour with limited agitation. The binding capacity of this resin may be sufficient for up to 60 mg of His6-tagged protein. After the His6-tagged pro-toxin is bound to the resin, the resin will be collected, and the supernatant wash buffer removed. Fluorescence will immediately confirm that no TetNT pro-toxin is present in the supernatant.

The collected protein-charged resin may be washed with 50 ml of HEPES buffer at pH 8.0, containing lactose, 200 mM NaCl, and incubated at ambient temperature, with no reducing agent present. Under exposure to $O_2$ in various concentrations (from 2% to atmospheric) and for various times and in absence of reducing agents, the spontaneous folding/refolding, oxidative formation of the native disulfide bridges, will be initiated within the long chain of TetNT and in between the long and short chain of TetNT.

Subsequent to the folding/refolding, $ZnCl_2$ may be added to a final concentration of 2 mM to the protein solution. This activates the internal autoproteolytical activity to cleave the peptide bond between the long chain and short chain of the resin-adsorbed TetNT. An incubation time of approximately 2 hours at 20-25° C. may be used initially. To this point the toxin is inert, as the engineered modifications with mCherry and a His6-tag will prevent its activity due to steric hinderance of the recognition and binding sites of its natural target. Furthermore, the bead size of the resin increases the total particle size significantly and reduces the risk of the protein being aerosolized or absorbed. The easy to detect fluorescence of mCherry helps to keep track of the protein and to prevent unwanted exposure or unintended disposal of potentially toxic material at this stage. The buffer may be exchanged to remove all incompletely folded toxin fragments that did not form disulfide bridges and will remove access $ZnCl_2$ from the solution.

A purified His6-tagged TEV protease may be added to the reaction mix and the sample is incubated for several hours at approximately 20-25° C. The TEV protease may be adsorbed to the resin as well and will remain bound, while the activated Tetanus toxin is released from the resin by cleaving the TEV protease site. This process can be monitored, by the quenching of the mCherry fluorescence, due to the cleavage of the TEV site overlapping with the missing N-terminus of mCherry and the resulting partial unfolding of the fluorescing protein. After no fluorescence can be detected, the resin, which is still charged with unfolded mCherry-His6 and TEV-His6 protease, is collected and the supernatant should contain only pure TetNT in a sterile and desired buffer.

The supernatant may be tested by the present inventors with a proprietary anti-Tet Fab, to confirm the correct protein folding in ELISA and western blot assays, while SDS-PAGE and FPLC profile confirm purity of the sample. After the protein concentration is determined the required amount of formaldehyde can be added to gain the inactivated toxoid. Animal assays to determine effective doses to confirm the degree of correctly folded and active protein in the final sample may further be conducted. Naturally, as described above, this protocol is exemplary in nature. Those of ordinary skill in the art will recognize that such protocols may be similarly employed, without undue experimentation to produce similar proteins from other Clostridia as well as other proteins of interest.

REFERENCES

The following references are hereby incorporated in their entirety by reference:

[1] Carlson, Erik D. et al. "Cell-Free Protein Synthesis: Applications Come of Age." *Biotechnology advances* 30.5 (2012): 1185-1194. PMC. Web. 1 Jan. 2018.

SEQUENCE LISTINGS

The instant application contains a Sequence Listing which has been submitted electronically in ASCII format and is hereby incorporated by reference in its entirety. In some cases, single letter designations for amino acids is provide in this specification, while three-letter designations have been provided in the electronically submitted format. All prior sequence data disclosed in U.S. Provisional Application No. 62/440,975 is hereby incorporated by reference.

TABLE 1

| Sequence Listings |
|---|
| SEQ ID NO. 1 |
| SGSSMIEIEKPKIETVELSEDAKYGKFVVEPLERGYGTTLGNSLRRILLSSLPGAAVTSVQIDG |
| VLHEFSTIDGVVEDVTAIILNIKKLALKIYSDEEKTLEIDVQGEGVVTAADITHDSDVEILNPD |
| LHIATLAEGGRLRMRMTAKRGRGYVPAEANKREDQPIGVIPIDSIYTPVSRVSYQVENTRVGQV |
| TDYDKLTIDVWTDGSIGPKEAISLGAKILTEHLNIFVGLTDEAQNAEIMVEKEDDQKEKVLEMT |
| IEELDLSVRSYNCLKRAGINTVQELTQKTEEDMMKVRNLGRKSLEEVKAKLAELGLSLRKDDGR |
| RAA |
| SEQ ID NO. 2 |
| SGSSMTGRLVQYGRHRQRRSYARISEVLELPNLIEIQTSSYQWFLDEGLREMFREISPIEDFSG |
| NLSLEFIDYSLGEPKYTVEEAKERDVTYAAPLRVKVRLINKETGEVKEQDVFMGDFPLMTETGT |
| FlINGAERVIVSRLVRSPSVYYSDKVDKNGKRGYSATVIPNRGAWLEYETDAKDVVYVRIDRTR |
| KLPVTVLLRALGFSSDQEIIDLLGDNEYLRNTLEKDNTDSTEKALIEIYERLRPGEPPTLENAK |
| NLLASRFFDPKRYDLASVGRYKINKKLHIKNRLFNQRLAETIIDPETKEVIAEAGAMIDRRTLN |
| RLLPYLEKGVGLQTYRPAEGVVDGDISVQTIKIYAPNDPDGEKVINVIGNGFIAEDVKHITPAD |
| IIASISYFFNLLHGVGDTDDIDHLGNRRLRSVGELLQNQFRIGLSRMERVVRERMSIQDTNTIT |
| PQQLINIRPVIAAIKEFFGSSQLSQFMDQTNPLAELTHKRRLSALGPGGLTRERAGFEVRDVHY |
| SHYGRMCPIETPEGPNIGLINSLSTYAKVNKFGFIETPYRRVDPETGRVTDQIDYLTADEEDNY |
| VVAQANVPLAEDGTFLEENVVARFRGENIVVKRDRVDYMDVSPKQVVSAATACIPFLENDDSNR |
| ALMGANMQRQAVPLLEPEAPIVGTGMEYVSAKDSGAAVICKHRGIVERVEAKEIWVRRLIEVDG |
| KEVKGDLDKYRLLKFVRSNQGTCYNQRPIVKKGDIVEKGEILADGPSMDKGELALGRNVLVAFM |
| TWDGYNYEDAIIMSERLVKEDVYTSIHIEEYEAESRDTKLGPEEITRDIPNVGEDALKNLDERG |
| IVRIGAEVKDGDLLVGKVTPKGMTELTAEERLLHAIFGEKAREVRDTSLRVPHGGGIVLDVKVF |
| NREDGDELPPGVNQLVRVYIVQKRKISEGDKMAGRHGNKGVISRILPEEDMPFLPDGTPIDIML |
| NPLGVPSRMNIGQVFELHLGMAAKKLGLHIASPVFDGATEEDVWNILEEAGLARDAKTVLYDGR |
| TGEPFDNRVSVGIMYMIKLAHMVDDKLHARSTGPYSLVTQQPLGGKAQFGGQRFGEMEVWALEA |
| YGAAYTLQEILTVKSDDVVGRVKTYEAIVKGENIPEPGVPESFKVLIKELQSLGMDVTILTSDE |
| QEVNMENFDDDDDHAPDAIMVDVKPAEREEAGEEKDAVTKEGRRAA |
| SEQ ID NO. 3 |
| SGSSMLDVNKFEYMKIGLASPEKIRSWSYGEVKKPETINYRTLKPEKDGLFERIFGPTKDWECH |
| CGKYKRVRYKGVVCDRCGVEVTRSKVRRERMGHIELAAPVSHIWYFKGIPSRMGLVLDMSPRAL |
| EEVIYFASYVVTDPGDTPLEKKQLLSEKEYRAYREKYGQSFQASMGAEAIKKLLQDIDLDKEVA |
| ALKEELKTAQGQRRARIIKRLEVLEAFRSSGNDPAWMVLDVLPVIPPELRPMVQLDGGRFATSD |
| LNDLYRRVINRNNRLKRLLDLGAPNIIVQNEKRMLQEAVDALIDNGRRGRPVTGPGNRPLKSLS |
| HMLKGKKGRFRQNLLGKRVDYSGRSVIVVGPNLKMYQCGLPKEMALELFKPFVMKELVERGLAH |
| NIKSAKRKIERVHPEVWDVLEDVIKEHPVLLNRAPTLHRLGIQAFEPTLVEGRAIRLHPLVCTA |
| YNADFDGDQMAVHVPLSAEAQAEARLLMLAAQNILNPKDGKPVVTPSQDMVLGNYYLTMEREGA |
| IGEGMVFKDTDEALLAYHNGYVHLHSRIAIHAGSLKNETFTEEQNNKLLLTTVGKLIFNEILPN |
| SFPYINEPTTENIEGRTPDKYFLDKGVNVREEIRKRELVPPFKKKVLGQIIAEVFKRFKITETS |

TABLE 1-continued

| Sequence Listings |
| --- |
| KMLDRMKDLGFQYSTKAGITIGVADIVVLPEKQEILDEAQAKVDTVLKQFRRGLITDEERYERV ISIWSAAKDKIQDRLMKSLDKRNPIFMMSDSGARGNASNFTQLAGMRGLMANPAGRIIELPIKS SFREGLTVLEYFISTHGARKGLADTALKTADSGYLTRRLVDVAQDVIVREEDCGTDRGILARAL TDGTEVVVKLEERLVGRYAHKTVRHPETGEVIVRKDEMITEDIANEIIKAGITEVWIRSVFACN TRHGVCKKCYGRNMATGMDVEVGEAVGIIAAQSIGEPGTQLTMRTFHTGGVAGDDITQGLPRVQ ELFEARNPKGQAVISEIDGTVISINETRDNQYEIVVQSEVETRTYVAPYNARLKVEEGQRVERG QELTEGSVDPKQLLRVRDITSVQEYLLREVQKVYRMQGVEISDKHIEVMVRQMLRKVRVIDAGD TDVLPGTLLDVHQFTDVNAKALREGKRPATARQVLLGITKASLETDSFLSASFQETTRVLTDA AIKGKRDELLGLKENVIIGKLVPAGTGMARYRKVKPAVKKETAGGTVSSKGRRAA |
| SEQ ID NO. 4 |
| SGSSMLDVNKFEYMKIGLASPEKIRSWSYGEVKKPETINYRTLKPEKDGLFCERIFGPTKDWEC HCGKYKRVRYKGVVCDRCGVEVTRSKVRRERMGHIELAAPVSHIWYFKGIPSRMGLVLDMSPRA LEEVIYFASYVVTDPGDTPLEKKQLLSEKEYRAYREKYGQSFQASMGAEAIKKLLQDIDLDKEV AALKEELKTAQGQRRARIIKRLEVLEAFRSSGNDPAWMVLDVLPVIPPELRPMVQLDGGRFATS DLNDLYRRVINRNNRLKRLLDLGAPNIIVQNEKRMLQEAVDALIDNGRRGRPVTGPGNRPLKSL SHMLKGKKGRFRQNLLGKRVDYSGRSVIVVGPNLKMYQCGLPKEMALELFKPFVMKELVERGLA HNIKSAKRKIERVHPEVWDVLEDVIKEHPVLNRAPTLHRLGIQAFEPTLVEGRAIRLHPLVCTA YNADFDGDQMAVHVPLSAEAQAEARLLMLAAQNILNPKDGKPVVTPSQDMVLGNYYLTMEREGA IGEGMVFKDTDEALLAYHNGYVHLHSRIAIHAGSLKNETFTEEQNNKLLLTTVGKLIFNEILPN SFPYINEPTTENIEGRTPDKYFLDKGVNVREEIRKRELVPPFKKKVLGQIIAEVFKRFKITETS KMLDRMKDLGFQYSTKAGITIGVADIVVLPEKQEILDEAQAKVDTVLKQFRRGLITDEERYERV ISIWSAAKDKIQDRLMKSLDKRNPIFMMSDSGARGNASNFTQLAGMRGLMANPAGRIIELPIKS SFREGLTVLEYFISTHGARKGLADTALKTADSGYLTRRLVDVAQDVIVREEDCGTDRGILARAL TDGTEVVVKLEERLVGRYAHKTVRHPETGEVIVRKDEMITEDIANEIIKAGITEVWIRSVFACN TRHGVCKKCYGRNMATGMDVEVGEAVGIIAAQSIGEPGTQLTMRTFHTGGVAGDDITQGLPRVQ ELFEARNPKGQAVISEIDGTVISINETRDNQYEIVVQSEVETRTYVAPYNARLKVEEGQRVERG QELTEGSVDPKQLLRVRDITSVQEYLLREVQKVYRMQGVEISDKHIEVMVRQMLRKVRVIDAGD TDVLPGTLLDVHQFTDVNAKALREGKRPATARQVLLGITKASLETDSFLSASFQETTRVLTDA AIKGKRDELLGLKENVIIGKLVPAGTGMARYRKVKPAVKKETAGGTVSSKGRRAA |
| SEQ ID NO. 5 |
| SGSSMSLQQQYSPEELQEMSFVELANLILLDKREALPFDQLVREAAALAGISEEEMEARLAQYY TDLNIDGRFICVGENVWGRAWYPFDQTEDETVTIVKPKKKKKALDDEYDEYDELLEDEDLDYDD LDEYDEEELELDEDELLEDEEFDLDEDVAFDDDILGDEEFELGDAPLDEELDLEEPEEDEGRRA A |
| SEQ ID NO. 6 |
| SGSSMLYPSIDLLMQKVDSKYKLVTVVAKRARELQDGAELMVKKPVSKKFVGQALEEIAGDKVE LVEEEKGRRAA |
| SEQ ID NO. 7 |
| MHHHHHHGKPIPNPLLGLDSTENLYFQGIDPFTMAEKPAQSKQAEAAGESLEQVKEQLAELGKK RGILTYEEIAERLSGFDLDSDQMDEYYEYLAEQGIEVISESDLEADPDIDDLAKEEEFDLNDLS VPPGVKINDPVRMYLKEIGRVPLLSAEEEIELAKRIEQGDEEAKRRLTEANLRLVVSIAKRYVG RGMLFLDLIQEGNMGLIKAVEKFDYRKGYKFSTYATWWIRQAITRAIADQARTIRIPVHMVETI NKLIRVQRQLLQDLGREPTPEEIAEEMDLTPEKVREILKIAQEPVSLETPIGEEDDSHLGDFIE DQDATSPSEHAAYELLKEQLEDVLDTLTDREENVLRLRFGLDDGRTRTLEEVGKVFGVTRERIR QIEAKALRKLRHPSRSKRLKDFLE |
| SEQ ID NO. 8 |
| SGSSMNLVLMGLPGAGKGTQAGKIVEAYGIPHISTGDMFRAAIKEGTPLGLQAKQYMDRGDLVP DELQAKQYMDRGDLVPDEGFLLDGFPRTVAQAEALETLLSEIGRKLDYVIHIDVRQEVLMERLT GRRICRNCGATYHLVFHPPAKPGVCDKCGGDLYQRPDNEATVANRLEVNMKQMKLLLDFYEQKG YLRHINGEQEMEKVFADICEVLGGLARGRRAA |
| SEQ ID NO. 9 |
| SGSSMGQEKLYIEKELSWLSFNERVLQEAADKSNPLIERMRFLGIYSNNLDEFYKVRFAELKRR IIISEEQGSNSHSRHLLGKIQSRVLKADQEFDGLYNELLLEMARNQIFLINERQLSVNQQNWLR HYFKQYLRQHITPILINPDTDLVQFLKDDYTYLAVEIIRGDTIRYALLEIPSDKVPRFVNLPPE APRRRKPMILLDNILRYCLDDIFKGFFDYDALNAYSMKMTRDAEYDLVHEMEASLMELMSSSLK QRLTAEPVRFVYQRDMPNALVEVLREKLTISRYDSIVPGGRYHNFKDFINFPNVGKANLVNKPL PRLRHIWFDKAQFRNGFDAIRERDVLLYYPYHTFEHVLELLRQASFDPSVLAIKINIYRVAKDS RIIDSMIHAAHNGKKVTVVVELQARFDEEANIHWAKRLTEAGVHVIFSAPGLKIHAKLFLISRK ENGEVVRYAHIGTGNFNEKTARLYTDYSLLTADARITNEVRRVFNFIENPYRPVTFDYLMVSPQ NSRRLLYEMVDREIANAQQGLPSGITLKLNNLVDKGLVDRLYAASSSGVPVNLLVRGMCSLIPN LEGISDNIRAISIVDRYLEHDRVYIFENGGDKKVYLSSADWMTRNIDYRIEVATPLLDPRLKQR VLDIIDILFSDTVKARYIDKELSNRYVPRGNRRKVRAQLAIYDYIKSLEQPEGRRAA |
| SEQ ID NO. 10 |
| MRLLPEESWLQFNRRVLRQSERPDFPLLERMRFLAIWNRNLDEFFAARIAKPFLKHRGSAHLRL LKEAEDQARLAEGRYRALLAEAAPHLKILEPEELDDLDWLYFRVFLAEVVVPKTDLIAWEAAKE ASHGALYFASEDHLVRLPQDLPRLLKVPGREGTYVRLGALMRARSDLFLPRESPLYEFRVLRLL ESERARADWDELAQALEGRQEGLSTLLVAERGFPKGWLEGLQEALGLLPEEVILLSPPLNLTLV ETLVAEGPSRWRFPPLEPKRPRAFMKNPLKRLQEKDLVLYHPFEDYAALERFAEAALSEEVEEV YATLYRIGEANPLAEALIQAARAGKRVHVLLEPRARFDELLNLSWYLRFLRAGVAVLPLSERKV HAKALLLLTQKGGYAHLGTGNYNPQNGRQYTDFSLFTARKEVVMEVAEFFRALQEGRTPRLNLL KTGEAIQELLLEHIRAESHPKGRILLKCNHLTDPALLEALARAADKGARVDLIVRSTLTLLHPR |

TABLE 1-continued

| Sequence Listings |
|---|
| FRARSLVGRFLEHARVAAFYQGGRWALYLTSADLMPRNFQNRFELLFPVLDKEGKAKVLEVLKR<br>QLKDDRNAFLLSPKGETPLWGGRHDAQRILAW |
| SEQ ID NO. 11<br>MHHHHHHGKPIPNPLLGLDSTENLYFQGIDPFTMRLLPEESWLQFNRRVLRQSERPDFPLLERM<br>RFLAIWNRNLDEFFAARIAKPFLKHRGSEAHLRLLKEAEDQARLAEGRYRALLAEAAPHLKILE<br>PEELDDLDWLYFRVFLAEVVVPKTDLIAWEAAKEASHGALYFASEDHLVRLPQDLPRLLKVPGR<br>EGTYVRLGALMRARSDLFLPRESPLYEFRVLRLLESERARADWDELAQALEGRQEGLSTLLVAE<br>RGFPKGWLEGLQEALGLLPEEVILLSPPLNLTLVETLVAEGPSRWRFPPLEPKRPRAFMKNPLK<br>RLQEKDLVLYHPFEDYAALERFAEAALSEEVEEVYATLYRIGEANPLAEALIQAARAGKRVHVL<br>LEPRARFDELLNLSWYLRFLRAGVAVLPLSERKVHAKALLLLTQKGGYAHLGTGNYNPQNGRQY<br>TDFSLFTARKEVVMEVAEFFRALQEGRTPRLNLLKTGEAIQELLLEHIRAESHPKGRILLKCNH<br>LTDPALLEALARAADKGARVDLIVRSTLTLLHPRFRARSLVGRFLEHARVAAFYQGGRWALYLT<br>SADLMPRNFQNRFELLFPVLDKEGKAKVLEVLKRQLKDDRNAFLLSPKGETPLWGGRHDAQRIA<br>W |
| SEQ ID NO. 12<br>MPITINNFRYSDPVNNDTIIMMEPPYCKGLDIYYKAFKITDRIWIVPERYEFGTKPEDFNPPSS<br>LIEGASEYYDPNYLRTDSDKDRFLQTMVKLFNRIKNNVAGEALLDKIINAIPYLGNSYSLLDKF<br>DTNSNSVSFNLLEQDPSGATTKSAMLTNLIIFGPGPVLNKNEVRGIVLRVDNKNYFPCRDGFGS<br>IMQMAFCPEYVPTFDNVIENITSLTIGKSKYFQDPALLLMHELIHVLHGLYGMQVSSHEIIPSK<br>QEIYMQHTYPISAEELFTFGGQDANLISIDIKNDLYEKTLNDYKAIANKLSQVTSCNDPNIDID<br>SYKQIYQQKYQFDKDSNGQYIVNEDKFQILYNSIMYGFTEIELGKKFNIKTRLSYFSMNHDPVK<br>IPNLLDDTIYNDTEGFNIESKDLKSEYKGQNMRVNTNAFRNVDGSGLVSKLIGLCKKIIPPTNI<br>RENLYNRTA |
| SEQ ID NO. 13<br>MHELIHVL |
| SEQ ID NO. 14<br>SLTDLGGELCIKIKNEDLTFIAEKNSFSEEPFQDEIVSYNTKNKPLNFNYSLDKIIVDYNLQSK<br>ITLPNDRTTPVTKGIPYAPEYKSNAASTIEIHNIDDNTIYQYLYAQKSPTTLQRITMTNSVDDA<br>LINSTKIYSYFPSVISKVNQGAQGILFLQWVRDIIDDFTNESSQKTTIDKISDVSTIVPYIGPA<br>LNIVKQGYEGNFIGALETTGVVLLLEYIPEITLPVIAALSIAESSTQKEKIIKTIDNFLEKRYE<br>KWIEVYKLVKAKWLGTVNTQFQKRSYQMYRSLEYQVDAIKKIIDYEYKIYSGPDKEQIADEINN<br>LKNKLEEKANKAMININIFMRESSRSFLVNQMINEAKKQLLEFDTQSKNILMQYIKANSKFIGI<br>TELKKLESKINKVFSTPIPFSYSKNLDCWVDNEEDIDVILKKSTILNLDINNDIISDISGFNSS<br>VITYPDAQLVPGINGKAIHLVNNESSEVIVHKAMDIEYNDMFNNFTVSFWLRVPKVSASHLEQY<br>GTNEYSIISSMKKHSLSIGSGWSVSLKGNNLIWTLKDSAGEVRQITFRDLPDKFNAYLANKWVF<br>ITITNDRLSSANLYINGVLMGSAEITGLGAIREDNNITLKLDRCNNNNQYVSIDKFRIFCKALN<br>PKEIEKLYTSYLSITFLRDFWGNPLRYDTEYYLIPVASSSKDVQLKNITDYMYLTNAPSYTNGK<br>LNIYYRRLYNGLKFIIKRYTPNNEIDSFVKSGDFIKLYVSYNNNEHIVGYPKDGNAFNNLDRIL<br>RVGYNAPGIPLYKKMEAVKLRDLKTYSVQLKLYDDKNASLGLVGTHNGQIGNDPNRDILIASNW<br>YFNHLKDKILGCDWYFVPTDEGWTNDGSA |
| SEQ ID NO. 15<br>ENLYFQS |
| SEQ ID NO. 16<br>GSGSNGSSGSVSMAIIKEFMRFKVHMEGSVNGHEFEIEGEGEGRPYEGTQTAKLKVTKGGPLPF<br>AWDILSPQFMYGSKAYVKHPADIPDYLKLSFPEGFKWERVMNFEDGGVVTVTQDSSLQDGEFIY<br>KVKLRGTNFPSDGPVMQKKTMGWEASSERMYPEDGALKGEIKQRLKLKDGGHYDAEVKTTYKAK<br>KPVQLPGAYNVNIKLDITSHNEDYTIVEQYERAEGRHSTGGMDELYRSGGGHHHHHHGDL |
| SEQ ID NO. 17<br>MPITINNFRYSDPVNNDTIIMMEPPYCKGLDIYYKAFKITDRIWIVPERYEFGTKPEDFNPPSS<br>LIEGASEYYDPNYLRTDSDKDRFLQTMVKLFNRIKNNVAGEALLDKIINAIPYLGNSYSLLDKF<br>DTNSNSVSFNLLEQDPSGATTKSAMLTNLIIFGPGPVLNKNEVRGIVLRVDNKNYFPCRDGFGS<br>IMQMAFCPEYVPTFDNVIENITSLTIGKSKYFQDPALLLMHELIHVLHGLYGMQVSSHEIIPSK<br>QEIYMQHTYPISAEELFTFGGQDANLISIDIKNDLYEKTLNDYKAIANKLSQVTSCNDPNIDID<br>SYKQIYQQKYQFDKDSNGQYIVNEDKFQILYNSIMYGFTEIELGKKFNIKTRLSYFSMNHDPVK<br>IPNLLDDTIYNDTEGFNIESKDLKSEYKGQNMRVNTNAFRNVDGSGLVSKLIGLCKKIIPPTNI<br>RENLYNRTASLTDLGGELCIKIKNEDLTFIAEKNSFSEEPFQDEIVSYNTKNKPLNFNYSLDKI<br>IVDYNLQSKITLPNDRTTPVTKGIPYAPEYKSNAASTIEIHNIDDNTIYQYLYAQKSPTTLQRI<br>TMTNSVDDALINSTKIYSYFPSVISKVNQGAQGILFLQWVRDIIDDFTNESSQKTTIDKISDVS<br>TIVPYIGPALNIVKQGYEGNFIGALETTGVVLLLEYIPEITLPVIAALSIAESSTQKEKIIKTI<br>DNFLEKRYEKWIEVYKLVKAKWLGTVNTQFQKRSYQMYRSLEYQVDAIKKIIDYEYKIYSGPDK<br>EQIADEINNLKNKLEEKANKAMININIFMRESSRSFLVNQMINEAKKQLLEFDTQSKNILMQYI<br>KANSKFIGITELKKLESKINKVFSTPIPFSYSKNLDCWVDNEEDIDVILKKSTILNLDINNDII<br>SDISGFNSSVITYPDAQLVPGINGKAIHLVNNESSEVIVHKAMDIEYNDMFNNFTVSFWLRVPK<br>VSASHLEQYGTNEYSIISSMKKHSLSIGSGWSVSLKGNNLIWTLKDSAGEVRQITFRDLPDKFN<br>AYLANKWVFITITNDRLSSANLYINGVLMGSAEITGLGAIREDNNITLKLDRCNNNNQYVSIDK<br>FRIFCKALNPKEIEKLYTSYLSITFLRDFWGNPLRYDTEYYLIPVASSSKDVQLKNITDYMYLT<br>NAPSYTNGKLNIYYRRLYNGLKFIIKRYTPNNEIDSFVKSGDFIKLYVSYNNNEHIVGYPKDGN<br>AFNNLDRILRVGYNAPGIPLYKKMEAVKLRDLKTYSVQLKLYDDKNASLGLVGTHNGQIGNDPN<br>RDILIASNWYFNHLKDKILGCDWYFVPTDEGWTNDGSAENLYFQSGSGSNGSSGSVSMAIIKEF<br>MRFKVHMEGSVNGHEFEIEGEGEGRPYEGTQTAKLKVTKGGPLPFAWDILSPQFMYGSKAYVKH<br>PADIPDYLKLSFPEGFKWERVMNFEDGGVVIVTQDSSLQDGEFIYKVKLRGINFPSDGPVMQKK |

TABLE 1-continued

Sequence Listings

TMGWEASSERMYPEDGALKGEIKQRLKLKDGGHYDAEVKTTYKAKKPVQLPGAYNVNIKLDIIS
HNEDYTIVEQYERAEGRHSTGGMDELYRSGGGHHHHHHGDL

SEQ ID NO. 18
ATTCTGCAATCCTATTGTTTATCATACCTGATATATGAAGATACGACACTAGGAGTGA
TGGCCATG

SEQ ID NO. 19
TAATACGACTCACTATAGGGGAATTGTGAGCGGATAACAATTCC

SEQ ID NO. 20
CCTCTAGAAATAATTTTGTTTAACTTTAAGAAGGAGATATACC

SEQ ID NO. 21
ATGCCAATAACCATAAATAATTTTAGATATAGTGATCCTGTTAATAATGATACAATTATTATGA
TGGAGCCACCATACTGTAAGGGTCTAGATATCTATTATAAGGCTTTCAAAATAACAGATCGTAT
TTGGATAGTGCCGGAAAGGTATGAATTTGGGACAAAACCTGAAGATTTTAACCCACCATCTTCA
TTAATAGAAGGTGCATCTGAGTATTACGATCCAAATTATTTAAGGACTGATTCTGATAAAGATA
GATTTTTACAAACCATGGTAAAACTGTTTAACAGAATTAAAAACAATGTAGCAGGTGAAGCCTT
ATTAGATAAGATAATAAATGCCATACCTTACCTTGGAAATTCATATTCCTTACTAGACAAGTTT
GATACAAACTCTAATTCAGTATC/TTTTAATTTATCAGAACAAGACCCCAGTGGAGCAACTACA
AAATCAGCAATGCTGACAAATTTAATAATATTTGGACCTGGGCCTGTTTTAAATAAAAATGAGG
TTAGAGGTATTGTATTGAGGGTAGATAATAAAAATTACTTCCCATGTAGAGATGGTTTTGGTTC
AATAATGCAAATGGCATTTTGCCCAGAATATATACCCACTTTTGATAATGTAATAGAAAATATT
ACGTCACTCACTATTGGCAAAAGCAAATATTTTCAAGATCCAGCATTACTATTAATGCACGAAC
TTATACATGTACTACATGGTTTATACGGAATGCAGGTATCAAGCCATGAAATTATTCCATCCAA
ACAAGAAATTTATATGCAGCATACATATCCAATAAGTGCTGAAGAACTATTCACTTTTGGCGGA
CAGGATGCTAATCTTATAAGTATTGATATAAAAAACGATTTATATGAAAAAACTTTAAATGATT
ATAAAGCTATAGCTAACAAACTTAGTCAAGTCACTAGCTGCAATGATCCCAACATTGATATTGA
TAGCTACAAACAAATATATCAACAAAAATATCAATTCGATAAAGATAGCAATGGACAATATATT
GTAAATGAGGATAAATTTCAGATACTATATAATAGCATAATGTATGGTTTTACAGAGATTGAAT
TGGGAAAAAAATTTAATATAAAAACTAGACTTTCTTATTTTAGTATGAATCATGACCCTGTAAA
AATTCCAAATTTATTAGATGATACAATTTACAATGATACAGAAGGATTTAATATAGAAAGCAAA
GATCTGAAATCTGAATATAAAGGTCAAAATATGAGGGTAAATACAAATGCTTTTAGAAATGTTG
ATGGATCAGGCCTAGTTTCAAAACTTATTGGCTTATGTAAAAAAATTATACCACCAACAAATAT
AAGAGAAAATTTATATAATAGAACTGCATCATTAACAGATTTAGGAGGAGAATTATGTATAAAA
ATTAAAAATGAAGATTTAACTTTTATAGCTGAAAAAAATAGCTTTTCAGAAGAACCATTTCAAG
ATGAAACAGTTAGTTATAATACAAAAAATAAACCATTAAATTTTAATTATTCGCTAGATAAAAT
TATTTTAGATTATAATCTACAAAGTAAAATTACATTACCTAATGATAGGACAACCCCAGTTACA
AAAGGAATTCCATATGCTCCAAAATATAAAAGTAATGCTGCAAGTACAATAGAAATACATAATA
TTGATGACAATACAATATATCAATATTTGTATGCTCAAAAATCTCCTACAACTCTACAAAGAAT
AACTATGACTAATTCTGTCGATGACGCATTAATAAATTCCACCAAAATATATTCATATTTTCCA
TCTGTAATCAGTAAAGTTAACCAAGGTGCACAAGGAATTTTATTCTTACAGTGGGTGAGAGATA
TAATTGATGATTTACCAATGAATCTTCACAAAAAACTACTATTGATAAAATTTCAGATGTATCC
ACTATTGTTCCTTATATAGGACCCGCATTAAACATTGTAAAACAAGGCTATGAGGGAAACTTTA
TAGGTGCTTTAGAAACTACCGGAGTGGTTTTATTATTGGAATATATTCCAGAAATTACTTTACC
AGTAATTGCAGCTTTATCTATAGCAGAAAGTAGCACACAAAAAGAAAAGATAATAAAAACAATA
GATAACTTTTTAGAAAAAAGATATGAAAAATGGATTGAAGTATATAAACTAATAAAAGCAAAAT
GGTTAGGCACAGTTAATACGCAATTCCAAAAAAGAAGTTATCAAATGTATAGATCTTTAGAATA
TCAAGTAGATGCAATAAAAAAAATAATAGACTATGAATATAAAATATATTCAGGACCTGATAAG
GAACAAATTGCCGACGAAATTAATAATCTGAAAAACAAACTTGAAGAAAAGGCTAATAAAGCAA
TGATAAACATAAATATATTTATGAGGGAAAGTTCTAGATCATTTTTAGTTAATCAAATGATTAA
CGAAGCTAAAAAGCAGTTATTAGAGTTTGATACTCAAAGCAAAAATATTTTAATGCAGTATATA
AAAGCAAATTCTAAATTTATAGGTATAACTGAACTAAAAAAATTAGAATCAAAAATAAACAAAG
TTTTTCAACACCAATTCCATTTTCTTATTCTAAAAATCTGGATTGTTGGGTTGATAATGAAGA
AGATATAGATGTTATATTAAAAAAGAGTACAATTTTAAATTTAGATATTAATAATGATATTATA
TCAGATATATCTGGGTTTAATTCATCTGTAATAACATATCCAGATGCTCAATTGGTGCCCGGAA
TAAATGGCAAAGCAATACATTTAGTAAACAATGAATCTTCTGAAGTTATAGTGCATAAAGCTAT
GGATATTGAATATAATGATATGTTTAATAATTTTACCGTTAGCTTTTGGTTGAGGGTTCCTAAA
GTATCTGCTAGTCATTTAGAACAATATGGCACAAATGAGTATTCAATAATTAGCTCTATGAAAA
AATATAGTCTATCAATAGGATCTGGTTGGAGTGTATCACTTAAAGGTAATAACTTAATATGGAC
TTTAAAAGATTCCGCGGGAGAAGTTAGACAAATAACTTTTAGTGATTTATCTGATAAATTTAAT
GCTTATTTAGCAAATAAATGGGTTTTTATAACTATTACTAATGATAGATTATCTTCTGCTAATT
TGTATATAAATGGAGTACTTATGAAAAATGCAGAAATTACCGGTTTAGGAGCTATTAGAGAGGA
TAATAATATAACATTAAAACTAGATAGATGTAATAATAATAATCAATACGTTTCTATTGATAAA
TTTAGGATATTTTGCAAAGCATTAAATCCAAAAGAGATTGAAAAATTATACACAAGTTATTTAT
CTATAACCTTTTTAAGAGACTTCTGGGGAAACCCTTTACGATATGATACAGAATATTATTTAAT
ACCAGTAGCTTCTAGTTCTAAAGATGTTCAATTGAAAAATATAACAGATTATATGTATTTGACA
AATGCGCCATCGTATACTAACGGAAAATTGAATATATATTATAGAAGGTTATATAGTGGACTAA
AATTTATTATAAAAAGATATACACCTAATAATGAAATAGATTCTTTTGTTAAATCAGGTGATTT
TATTAAATTATATGTATCATATAACAATAATGAGCACATTGTAGGTTATCCGAAAGATGGAAAT
GCCTTTAATAATCTTGATAGAATTCTAAGAGTAGGTTATAATGCCCCAGGTATCCCTCTTTATA
AAAAAATGGAAGCAGTAAAATTGCGTGATTTAAAAACCTATTCTGTACAACTTAAATTATATGA
TGATAAAAATGCATCTTTAGGACTAGTAGGTATCCGTAATGGTCAAATAGGCAACGATCCAAAT
AGGGATATATTAATTGCAAGCAACTGGTACTTTAATCATTTAAAAGATAAAACTTTAACATGTG
ATTGGTACTTTGTACCTACAGATGAAGGATGGACAAATGATTAA

TABLE 1-continued

| Sequence Listings |
|---|
| SEQ ID NO. 22<br>GAAAACCTGTACTTCCAATCCAATATTGGTAGTGGGAGCAACGGCAGCAGCGGATCCGTGAGCA<br>AGGGCGAGGAGGATAACATGGCCATCATCAAGGAGTTCATGCGCTTCAAGGTGCACATGGAGGG<br>CTCCGTGAACGGCCACGAGTTCGAGATCGAGGGCGAGGGCGAGGGCCGCCCCTACGAGGGCACC<br>CAGACCGCCAAGCTGAAGGTGACCAAGGGTGGCCCCCTGCCCTTCGCCTGGGACATCCTGTCCC<br>CTCAGTTCATGTACGGCTCCAAGGCCTACGTGAAGCACCCCGCCGACATCCCCGACTACTTGAA<br>GCTGTCCTTCCCCGAGGGCTTCAAGTGGGAGCGCGTGATGAACTTCGAGGACGGCGGCGTGGTG<br>ACCGTGACCCAGGACTCCTCCCTCCAGGACGGCGAGTTCATCTACAAGGTGAAGCTGCGCGGCA<br>CCAACTTCCCCTCCGACGGCCCCGTAATGCAGAAGAAGACCATGGGCTGGGAGGCCTCCTCCGA<br>GCGGATGTACCCCGAGGACGGCGCCCTGAAGGGCGAGATCAAGCAGAGGCTGAAGCTGAAGGAC<br>GGCGGCCACTACGACGCTGAGGTCAAGACCACCTACAAGGCCAAGAAGCCCGTGCAGCTGCCCG<br>GCGCCTACAACGTCAACATCAAGTTGGACATCACCTCCCACAACGAGGACTACACCATCGTGGA<br>ACAGTACGAACGCGCCGAGGGCCGCCACTCCACCGGCGGCATGGACGAGCTGTACAAGTAAGCG<br>GCCGCACTCGAGCACCACCACCACCACCACTGA |
| SEQ ID NO. 23<br>MERTFVMIKPDGVRRGLVGEILARFERKGFRIAALKLMQISQELAERHYAEHREKPFFPGLVRF<br>ITSGPVVAMVLEGPGVVAEVRKMMGATHPKDALPGTIRGDFATTIDENVIHGSATLEDAQREIA<br>LFFRPEELL |

TABLE 1

| Amino Acid Sequence for recombinant TaqPPK showing: 6xHis-Tag; V5 epitope tag and TEV cleavage site (SEQ ID NO. 11)<br>His6 V5 tag TEV \/ TaqPPK |
|---|
| MHHHHHHGKPIPNPLLGLDSTENLYFQGIDPFTMRLLPEESWLQFNRRVL<br>RQSERPDFPLLERMRFLAIWNRNLDEFFAARIAKPFLKHRGSEAHLRLLK<br>EAEDQARLAEGRYRALLAEAAPHLKILEPEELDDLDWLYFRVFLAEVVVP<br>KTDLIANEAAKEASHGALYFASEDHLVRLPQDLPRLLKVPGREGTYVRLG<br>ALMRARSDLFLPRESPLYEFRVLRLLESERARADWDELAQALEGRQEGLS<br>TLLVAERGFPKGWLEGLQEALGLLPEEVILLSPPLNLTLVETLVAEGPSR<br>WRFPPLEPKRPRAFMKNPLKRLQEKDLVLYHPFEDYAALERFAEAALSEE<br>VEEVYATLYRIGEANPLAEALIQAARAGKRVHVLLEPRARFDELLNLSWY<br>LRFLRAGVAVLPLSERKVHAKALLLLTQKGGYAHLGIGNYNPQNGRQYTD<br>FSLFTARKEVVMEVAEFFRALQEGRTPRLNLLKTGEAIQELLLEHIRAES<br>HPKGRILLKCNHLTDPALLEALARAADKGARVDLIVRSTLTLLHPRFRAR<br>SLVGRFLEHARVAAFYQGGRWALYLTSADLMPRNFQNRFELLFPVLDKEG<br>KAKVLEVLKRQLKDDRNAFLLSPKGETPLWGGRHDAQRILAW |

TABLE 2

Reaction mixtures of NDPK reactions reflective of the ping-pong mechanism of XDP + YTP -> XTP + TDP

| ADP/GTP | | ADP/GTP | |
|---|---|---|---|
| 4 | 5× Reaction Buffer | 4 | 5× Reaction Buffer |
| 1 | 100 mM GTP | 0 | 100 mM GTP |

TABLE 2-continued

Reaction mixtures of NDPK reactions reflective of the ping-pong mechanism of XDP + YTP -> XTP + TDP

| | | | |
|---|---|---|---|
| 0.5 | 200 mM ADP | 0.5 | 200 mM ADP |
| 1 | 5.0 mg/ml NDPK | 1 | 5.0 mg/ml NDPK |
| 13.5 | dH2O | 14.5 | dH2O |
| 20 | TOTAL | 20 | TOTAL |
| ADP/CTP | | ADP/CTP | |
| 4 | 5× Reaction Buffer | 4 | 5× Reaction Buffer |
| 1 | 100 mM CTP | 0 | 100 mM CTP |
| 0.5 | 200 mM ADP | 0.5 | 200 mM ADP |
| 1 | 5.0 mg/ml NDPK | 1 | 5.0 mg/ml NDPK |
| 13.5 | dH2O | 14.5 | dH2O |
| 20 | TOTAL | 20 | TOTAL |
| ADP/GTP | | ADP/GTP | |
| 4 | 5× Reaction Buffer | 4 | 5× Reaction Buffer |
| 1 | 100 mM GTP | 1 | 100 mM GTP |
| 0 | 200 mM ADP | 0.5 | 200 mM ADP |
| 1 | 5.0 mg/ml NDPK | 0 | 5.0 mg/ml NDPK |
| 14 | dH2O | 14.5 | dH2O |
| 20 | TOTAL | 20 | TOTAL |

What is claimed is:

1. A cell-free protein expression system comprising:
a bioreactor having:
a reaction mixture containing isolated cell-free reaction components necessary for in vitro macromolecule synthesis;
at least one isolated nucleic acid synthesis template; and
a cellular adenosine triphosphate (ATP) energy regeneration system comprising:
purified Adenosyl Kinase (AdK) enzyme according to SEQ ID NO: 8, or fragment thereof, or an Adk enzyme having a sequence having at least 95% sequence homology with SEQ ID NO: 8, that catalyzes the conversion of adenosine diphosphate into adenosine triphosphate (ATP) and adenosine monophosphate (AMP);
purified Polyphosphate Kinase (PPK) enzyme according to SEQ ID NO: 11, or fragment thereof, or a PPK enzyme having a sequence having at least 95% sequence homology with SEQ ID NO: 11, that catalyzes the reversible formation of ATP from ADP and inorganic polyphosphate (PPi);
isolated PPi; and
isolated adenosine monophosphate (AMP);
wherein said AdK and PPK enzymes work synergistically to regenerate cellular ATP energy from PPi and AMP.

2. The system of claim 1, wherein said isolated cell-free reaction components are selected from the group consisting of:
amino acids;
polyphosphate;
Tris-Acetate;
$Mg(OAc)_2$;
$K^+$-glutamate;
amino-acetate;
NaCl;
KCl;
$MgCl_2$;
DTT;
octyl-b-glycoside;
NAD;
NADP;
sorbitol;
FADH;
ATP;
GTP;
UTP;
CTP;
CoA;
PLP; and
SAM.

3. The system of claim 1, wherein said isolated cell-free reaction components are selected from the group consisting of:
2 mM of each natural amino acid;
1 mg/ml polyphosphate;
5 mM Tris-Acetate;
4 mM $Mg(OAc)_2$;
12 mM $K^+$-glutamate;
1 mM amino-acetate;
100 mM NaCl;
10 mM KCl;
5 mM $MgCl_2$;
0.1 mM DTT;
0.2% octyl-b-glycoside;
0.8 mM NAD;
0.4 mM NADP;
200 mM sorbitol;
0.5 mM FADH;
1.5 mM ATP;
1 mM GTP, UTP, CTP each;
1 mM CoA;
2 mM PLP; and
0.2 mM SAM.

4. The system of claim 1, further comprising purified thermostable RNA polymerase (RNAP).

5. The system of claim 4, wherein RNAP comprises RNAP isolated from *Geobacillus stearothermophilus* (Gst RNAP).

6. The system of claim 5, wherein said Gst RNAP comprises RNAP subunits:
subunit alpha according to SEQ ID NO: 1;
subunit beta according to SEQ ID NO: 2;
subunit beta' according to SEQ ID NO: 3 or subunit beta' according to SEQ ID NO: 4;
subunit delta according to SEQ ID NO: 5; and
subunit omega according to SEQ ID NO: 6.

7. The system of claim 1, further comprising tRNAs isolated from *Geobacillus.*

8. The system of claim 1, further comprising tRNAs isolated from *E. coli* mre600.

9. The system of claim 1, further comprising a quantity of isolated Sorbitol-dehydrogenase (SDH).

10. The system of claim 9, wherein said SDH is isolated from *Geobacillus stearothermophilus* (Gst SDH).

11. The system of claim 10, further comprising a quantity of isolated sorbitol.

12. The system of claim 1, wherein said macromolecule comprises a polypeptide.

13. The system of claim 1, wherein said at least one isolated nucleic acid synthesis template comprises at least one isolated linear DNA template.

14. The system of claim 13, wherein said at least one isolated nucleic acid synthesis template comprises at least one isolated codon optimized nucleic acid synthesis template.

15. The system of claim 1, wherein said at least one isolated nucleic acid synthesis template comprises at least one isolated nucleic acid synthesis template having:

at least one target expression product gene operably linked to a promoter;

at least one ribosome binding site (RBS);

at least one expression product cleavage site; and at least one tag.

16. The system of claim 15, wherein said promoter comprises either an RhIII promoter according to SEQ ID NO: 18, or a T7 promoter according to SEQ ID NO: 19.

17. The system of claim 15, wherein said at least one target expression product gene operably linked to a promoter comprises a tentoxilysin (TetNT) gene operably linked to a promoter.

18. The system of claim 17, wherein said TetNT gene comprises a recombinant a first construct coding for a TetNT light chain according to SEQ ID NO: 12, with an autocatalytic protease site according to SEQ ID NO: 13 and disulfide bridge forming cysteines, and a second construct coding for a TetNT heavy chain according to SEQ ID NO: 14 and containing a partially integrated TEV site according to SEQ ID NO: 15, and mCherry-His6 according to SEQ ID NO: 16.

19. The system of claim 17, wherein said TetNT gene comprises a recombinant TetNT gene according to SEQ ID NO: 21.

20. The system of claim 15, wherein said RBS comprises an RBS according to SEQ ID NO: 20.

21. The system of claim 15, wherein said at least one expression product cleavage site comprises a TEV site according to SEQ ID NO: 15.

22. The system of claim 15, wherein said at least one target expression product is a peptide according to SEQ ID NO: 17.

23. The system of claim 1, wherein said purified AdK enzyme comprises a purified thermostable AdK enzyme, or fragment thereof.

24. The system of claim 23, wherein said purified thermostable AdK enzyme comprises purified thermostable *Geobacillus stearothermophilus* AdK enzyme (Gst Adk), or fragment thereof.

25. The system of claim 1, wherein said purified PPK enzyme comprises purified thermostable PPK enzyme, or fragment thereof.

26. The system of claim 25, wherein said purified thermostable PPK enzyme comprises purified thermostable *Thermus aquaticus* PPK enzyme (TaqPPK), or fragment thereof.

27. The system of claim 1, wherein the quantity of purified Gst Adk enzyme is greater than the quantity of purified TaqPPK enzyme.

28. The system of claim 27, wherein the molar ratio of purified Gst Adk:purified TaqPPK is 3:1.

29. The system of claim 1, wherein said isolated PPi comprises a PPi concentration range that maintains the equilibrium of the ATP regeneration reaction.

30. The system of claim 29, wherein said PPi concentration range that maintains the equilibrium of the ATP regeneration reaction comprises a concentration range of 0.2-2 mg/ml PPi in a 100 μl volume ATP regenerating reaction.

* * * * *

SEQUENCE LISTING

```
<160> NUMBER OF SEQ ID NOS: 25

<210> SEQ ID NO 1
<211> LENGTH: 323
<212> TYPE: PRT
<213> ORGANISM: Geobacillus Stearothermphilus

<400> SEQUENCE: 1

Ser Gly Ser Ser Met Ile Glu Ile Glu Lys Pro Lys Ile Glu Thr Val
1               5                   10                  15

Glu Leu Ser Glu Asp Ala Lys Tyr Gly Lys Phe Val Val Glu Pro Leu
            20                  25                  30

Glu Arg Gly Tyr Gly Thr Thr Leu Gly Asn Ser Leu Arg Arg Ile Leu
```

```
        35                  40                  45

Leu Ser Ser Leu Pro Gly Ala Ala Val Thr Ser Val Gln Ile Asp Gly
    50                  55                  60

Val Leu His Glu Phe Ser Thr Ile Asp Gly Val Val Glu Asp Val Thr
65                  70                  75                  80

Ala Ile Ile Leu Asn Ile Lys Lys Leu Ala Leu Lys Ile Tyr Ser Asp
                85                  90                  95

Glu Glu Lys Thr Leu Glu Ile Asp Val Gln Gly Glu Gly Val Val Thr
            100                 105                 110

Ala Ala Asp Ile Thr His Asp Ser Asp Val Glu Ile Leu Asn Pro Asp
        115                 120                 125

Leu His Ile Ala Thr Leu Ala Glu Gly Gly Arg Leu Arg Met Arg Met
    130                 135                 140

Thr Ala Lys Arg Gly Arg Gly Tyr Val Pro Ala Glu Ala Asn Lys Arg
145                 150                 155                 160

Glu Asp Gln Pro Ile Gly Val Ile Pro Ile Asp Ser Ile Tyr Thr Pro
                165                 170                 175

Val Ser Arg Val Ser Tyr Gln Val Glu Asn Thr Arg Val Gly Gln Val
            180                 185                 190

Thr Asp Tyr Asp Lys Leu Thr Ile Asp Val Trp Thr Asp Gly Ser Ile
        195                 200                 205

Gly Pro Lys Glu Ala Ile Ser Leu Gly Ala Lys Ile Leu Thr Glu His
    210                 215                 220

Leu Asn Ile Phe Val Gly Leu Thr Asp Glu Ala Gln Asn Ala Glu Ile
225                 230                 235                 240

Met Val Glu Lys Glu Asp Asp Gln Lys Glu Lys Val Leu Glu Met Thr
                245                 250                 255

Ile Glu Glu Leu Asp Leu Ser Val Arg Ser Tyr Asn Cys Leu Lys Arg
            260                 265                 270

Ala Gly Ile Asn Thr Val Gln Glu Leu Thr Gln Lys Thr Glu Glu Asp
        275                 280                 285

Met Met Lys Val Arg Asn Leu Gly Arg Lys Ser Leu Glu Glu Val Lys
    290                 295                 300

Ala Lys Leu Ala Glu Leu Gly Leu Ser Leu Arg Lys Asp Asp Gly Arg
305                 310                 315                 320

Arg Ala Ala


<210> SEQ ID NO 2
<211> LENGTH: 1198
<212> TYPE: PRT
<213> ORGANISM: Geobacillus Stearothermphilus

<400> SEQUENCE: 2

Ser Gly Ser Ser Met Thr Gly Arg Leu Val Gln Tyr Gly Arg His Arg
1               5                   10                  15

Gln Arg Arg Ser Tyr Ala Arg Ile Ser Glu Val Leu Glu Leu Pro Asn
            20                  25                  30

Leu Ile Glu Ile Gln Thr Ser Ser Tyr Gln Trp Phe Leu Asp Glu Gly
        35                  40                  45

Leu Arg Glu Met Phe Arg Glu Ile Ser Pro Ile Glu Asp Phe Ser Gly
    50                  55                  60

Asn Leu Ser Leu Glu Phe Ile Asp Tyr Ser Leu Gly Glu Pro Lys Tyr
65                  70                  75                  80

Thr Val Glu Glu Ala Lys Glu Arg Asp Val Thr Tyr Ala Ala Pro Leu
```

-continued

```
                85                  90                  95

Arg Val Lys Val Arg Leu Ile Asn Lys Glu Thr Gly Glu Val Lys Glu
            100                 105                 110

Gln Asp Val Phe Met Gly Asp Phe Pro Leu Met Thr Glu Thr Gly Thr
        115                 120                 125

Phe Ile Ile Asn Gly Ala Glu Arg Val Ile Val Ser Arg Leu Val Arg
    130                 135                 140

Ser Pro Ser Val Tyr Tyr Ser Asp Lys Val Asp Lys Asn Gly Lys Arg
145                 150                 155                 160

Gly Tyr Ser Ala Thr Val Ile Pro Asn Arg Gly Ala Trp Leu Glu Tyr
                165                 170                 175

Glu Thr Asp Ala Lys Asp Val Val Tyr Val Arg Ile Asp Arg Thr Arg
            180                 185                 190

Lys Leu Pro Val Thr Val Leu Leu Arg Ala Leu Gly Phe Ser Ser Asp
        195                 200                 205

Gln Glu Ile Ile Asp Leu Leu Gly Asp Asn Glu Tyr Leu Arg Asn Thr
    210                 215                 220

Leu Glu Lys Asp Asn Thr Asp Ser Thr Glu Lys Ala Leu Ile Glu Ile
225                 230                 235                 240

Tyr Glu Arg Leu Arg Pro Gly Glu Pro Pro Thr Leu Glu Asn Ala Lys
                245                 250                 255

Asn Leu Leu Ala Ser Arg Phe Phe Asp Pro Lys Arg Tyr Asp Leu Ala
            260                 265                 270

Ser Val Gly Arg Tyr Lys Ile Asn Lys Lys Leu His Ile Lys Asn Arg
        275                 280                 285

Leu Phe Asn Gln Arg Leu Ala Glu Thr Ile Ile Asp Pro Glu Thr Lys
    290                 295                 300

Glu Val Ile Ala Glu Ala Gly Ala Met Ile Asp Arg Arg Thr Leu Asn
305                 310                 315                 320

Arg Leu Leu Pro Tyr Leu Glu Lys Gly Val Gly Leu Gln Thr Tyr Arg
                325                 330                 335

Pro Ala Glu Gly Val Val Asp Gly Asp Ile Ser Val Gln Thr Ile Lys
            340                 345                 350

Ile Tyr Ala Pro Asn Asp Pro Asp Gly Glu Lys Val Ile Asn Val Ile
        355                 360                 365

Gly Asn Gly Phe Ile Ala Glu Asp Val Lys His Ile Thr Pro Ala Asp
    370                 375                 380

Ile Ile Ala Ser Ile Ser Tyr Phe Phe Asn Leu Leu His Gly Val Gly
385                 390                 395                 400

Asp Thr Asp Asp Ile Asp His Leu Gly Asn Arg Arg Leu Arg Ser Val
                405                 410                 415

Gly Glu Leu Leu Gln Asn Gln Phe Arg Ile Gly Leu Ser Arg Met Glu
            420                 425                 430

Arg Val Val Arg Glu Arg Met Ser Ile Gln Asp Thr Asn Thr Ile Thr
        435                 440                 445

Pro Gln Gln Leu Ile Asn Ile Arg Pro Val Ile Ala Ala Ile Lys Glu
    450                 455                 460

Phe Phe Gly Ser Ser Gln Leu Ser Gln Phe Met Asp Gln Thr Asn Pro
465                 470                 475                 480

Leu Ala Glu Leu Thr His Lys Arg Arg Leu Ser Ala Leu Gly Pro Gly
                485                 490                 495

Gly Leu Thr Arg Glu Arg Ala Gly Phe Glu Val Arg Asp Val His Tyr
            500                 505                 510
```

-continued

```
Ser His Tyr Gly Arg Met Cys Pro Ile Glu Thr Pro Glu Gly Pro Asn
        515                 520                 525

Ile Gly Leu Ile Asn Ser Leu Ser Thr Tyr Ala Lys Val Asn Lys Phe
    530                 535                 540

Gly Phe Ile Glu Thr Pro Tyr Arg Arg Val Asp Pro Glu Thr Gly Arg
545                 550                 555                 560

Val Thr Asp Gln Ile Asp Tyr Leu Thr Ala Asp Glu Glu Asp Asn Tyr
                565                 570                 575

Val Val Ala Gln Ala Asn Val Pro Leu Ala Glu Asp Gly Thr Phe Leu
            580                 585                 590

Glu Glu Asn Val Val Ala Arg Phe Arg Gly Glu Asn Ile Val Val Lys
        595                 600                 605

Arg Asp Arg Val Asp Tyr Met Asp Val Ser Pro Lys Gln Val Val Ser
    610                 615                 620

Ala Ala Thr Ala Cys Ile Pro Phe Leu Glu Asn Asp Asp Ser Asn Arg
625                 630                 635                 640

Ala Leu Met Gly Ala Asn Met Gln Arg Gln Ala Val Pro Leu Leu Glu
                645                 650                 655

Pro Glu Ala Pro Ile Val Gly Thr Gly Met Glu Tyr Val Ser Ala Lys
            660                 665                 670

Asp Ser Gly Ala Ala Val Ile Cys Lys His Arg Gly Ile Val Glu Arg
        675                 680                 685

Val Glu Ala Lys Glu Ile Trp Val Arg Arg Leu Ile Glu Val Asp Gly
    690                 695                 700

Lys Glu Val Lys Gly Asp Leu Asp Lys Tyr Arg Leu Leu Lys Phe Val
705                 710                 715                 720

Arg Ser Asn Gln Gly Thr Cys Tyr Asn Gln Arg Pro Ile Val Lys Lys
                725                 730                 735

Gly Asp Ile Val Glu Lys Gly Glu Ile Leu Ala Asp Gly Pro Ser Met
            740                 745                 750

Asp Lys Gly Glu Leu Ala Leu Gly Arg Asn Val Leu Val Ala Phe Met
        755                 760                 765

Thr Trp Asp Gly Tyr Asn Tyr Glu Asp Ala Ile Ile Met Ser Glu Arg
    770                 775                 780

Leu Val Lys Glu Asp Val Tyr Thr Ser Ile His Ile Glu Glu Tyr Glu
785                 790                 795                 800

Ala Glu Ser Arg Asp Thr Lys Leu Gly Pro Glu Glu Ile Thr Arg Asp
                805                 810                 815

Ile Pro Asn Val Gly Glu Asp Ala Leu Lys Asn Leu Asp Glu Arg Gly
            820                 825                 830

Ile Val Arg Ile Gly Ala Glu Val Lys Asp Gly Asp Leu Leu Val Gly
        835                 840                 845

Lys Val Thr Pro Lys Gly Met Thr Glu Leu Thr Ala Glu Glu Arg Leu
    850                 855                 860

Leu His Ala Ile Phe Gly Glu Lys Ala Arg Glu Val Arg Asp Thr Ser
865                 870                 875                 880

Leu Arg Val Pro His Gly Gly Gly Ile Val Leu Asp Val Lys Val Phe
                885                 890                 895

Asn Arg Glu Asp Gly Asp Glu Leu Pro Pro Gly Val Asn Gln Leu Val
            900                 905                 910

Arg Val Tyr Ile Val Gln Lys Arg Lys Ile Ser Glu Gly Asp Lys Met
        915                 920                 925
```

-continued

```
Ala Gly Arg His Gly Asn Lys Gly Val Ile Ser Arg Ile Leu Pro Glu
    930                 935                 940

Glu Asp Met Pro Phe Leu Pro Asp Gly Thr Pro Ile Asp Ile Met Leu
945                 950                 955                 960

Asn Pro Leu Gly Val Pro Ser Arg Met Asn Ile Gly Gln Val Phe Glu
                965                 970                 975

Leu His Leu Gly Met Ala Ala Lys Lys Leu Gly Leu His Ile Ala Ser
            980                 985                 990

Pro Val Phe Asp Gly Ala Thr Glu  Glu Asp Val Trp Asn  Ile Leu Glu
        995                 1000                 1005

Glu Ala  Gly Leu Ala Arg Asp  Ala Lys Thr Val Leu  Tyr Asp Gly
    1010                 1015                 1020

Arg Thr  Gly Glu Pro Phe Asp  Asn Arg Val Ser Val  Gly Ile Met
    1025                 1030                 1035

Tyr Met  Ile Lys Leu Ala His  Met Val Asp Asp Lys  Leu His Ala
    1040                 1045                 1050

Arg Ser  Thr Gly Pro Tyr Ser  Leu Val Thr Gln Gln  Pro Leu Gly
    1055                 1060                 1065

Gly Lys  Ala Gln Phe Gly Gly  Gln Arg Phe Gly Glu  Met Glu Val
    1070                 1075                 1080

Trp Ala  Leu Glu Ala Tyr Gly  Ala Ala Tyr Thr Leu  Gln Glu Ile
    1085                 1090                 1095

Leu Thr  Val Lys Ser Asp Asp  Val Val Gly Arg Val  Lys Thr Tyr
    1100                 1105                 1110

Glu Ala  Ile Val Lys Gly Glu  Asn Ile Pro Glu Pro  Gly Val Pro
    1115                 1120                 1125

Glu Ser  Phe Lys Val Leu Ile  Lys Glu Leu Gln Ser  Leu Gly Met
    1130                 1135                 1140

Asp Val  Thr Ile Leu Thr Ser  Asp Glu Gln Glu Val  Asn Met Glu
    1145                 1150                 1155

Asn Phe  Asp Asp Asp Asp Asp  His Ala Pro Asp Ala  Ile Met Val
    1160                 1165                 1170

Asp Val  Lys Pro Ala Glu Arg  Glu Glu Ala Gly Glu  Glu Lys Asp
    1175                 1180                 1185

Ala Val  Thr Lys Glu Gly Arg  Arg Ala Ala
    1190                 1195


<210> SEQ ID NO 3
<211> LENGTH: 1207
<212> TYPE: PRT
<213> ORGANISM: Geobacillus Stearothermphilus

<400> SEQUENCE: 3

Ser Gly Ser Ser Met Leu Asp Val Asn Lys Phe Glu Tyr Met Lys Ile
1               5                   10                  15

Gly Leu Ala Ser Pro Glu Lys Ile Arg Ser Trp Ser Tyr Gly Glu Val
            20                  25                  30

Lys Lys Pro Glu Thr Ile Asn Tyr Arg Thr Leu Lys Pro Glu Lys Asp
        35                  40                  45

Gly Leu Phe Glu Arg Ile Phe Gly Pro Thr Lys Asp Trp Glu Cys His
    50                  55                  60

Cys Gly Lys Tyr Lys Arg Val Arg Tyr Lys Gly Val Val Cys Asp Arg
65                  70                  75                  80

Cys Gly Val Glu Val Thr Arg Ser Lys Val Arg Arg Glu Arg Met Gly
                85                  90                  95
```

-continued

```
His Ile Glu Leu Ala Ala Pro Val Ser His Ile Trp Tyr Phe Lys Gly
            100                 105                 110

Ile Pro Ser Arg Met Gly Leu Val Leu Asp Met Ser Pro Arg Ala Leu
        115                 120                 125

Glu Glu Val Ile Tyr Phe Ala Ser Tyr Val Val Thr Asp Pro Gly Asp
    130                 135                 140

Thr Pro Leu Glu Lys Lys Gln Leu Leu Ser Glu Lys Glu Tyr Arg Ala
145                 150                 155                 160

Tyr Arg Glu Lys Tyr Gly Gln Ser Phe Gln Ala Ser Met Gly Ala Glu
                165                 170                 175

Ala Ile Lys Lys Leu Leu Gln Asp Ile Asp Leu Asp Lys Glu Val Ala
            180                 185                 190

Ala Leu Lys Glu Glu Leu Lys Thr Ala Gln Gly Gln Arg Arg Ala Arg
        195                 200                 205

Ile Ile Lys Arg Leu Glu Val Leu Glu Ala Phe Arg Ser Ser Gly Asn
    210                 215                 220

Asp Pro Ala Trp Met Val Leu Asp Val Leu Pro Val Ile Pro Pro Glu
225                 230                 235                 240

Leu Arg Pro Met Val Gln Leu Asp Gly Gly Arg Phe Ala Thr Ser Asp
                245                 250                 255

Leu Asn Asp Leu Tyr Arg Arg Val Ile Asn Arg Asn Asn Arg Leu Lys
            260                 265                 270

Arg Leu Leu Asp Leu Gly Ala Pro Asn Ile Ile Val Gln Asn Glu Lys
        275                 280                 285

Arg Met Leu Gln Glu Ala Val Asp Ala Leu Ile Asp Asn Gly Arg Arg
    290                 295                 300

Gly Arg Pro Val Thr Gly Pro Gly Asn Arg Pro Leu Lys Ser Leu Ser
305                 310                 315                 320

His Met Leu Lys Gly Lys Lys Gly Arg Phe Arg Gln Asn Leu Leu Gly
                325                 330                 335

Lys Arg Val Asp Tyr Ser Gly Arg Ser Val Ile Val Val Gly Pro Asn
            340                 345                 350

Leu Lys Met Tyr Gln Cys Gly Leu Pro Lys Glu Met Ala Leu Glu Leu
        355                 360                 365

Phe Lys Pro Phe Val Met Lys Glu Leu Val Glu Arg Gly Leu Ala His
    370                 375                 380

Asn Ile Lys Ser Ala Lys Arg Lys Ile Glu Arg Val His Pro Glu Val
385                 390                 395                 400

Trp Asp Val Leu Glu Asp Val Ile Lys Glu His Pro Val Leu Leu Asn
                405                 410                 415

Arg Ala Pro Thr Leu His Arg Leu Gly Ile Gln Ala Phe Glu Pro Thr
            420                 425                 430

Leu Val Glu Gly Arg Ala Ile Arg Leu His Pro Leu Val Cys Thr Ala
        435                 440                 445

Tyr Asn Ala Asp Phe Asp Gly Asp Gln Met Ala Val His Val Pro Leu
    450                 455                 460

Ser Ala Glu Ala Gln Ala Glu Ala Arg Leu Leu Met Leu Ala Ala Gln
465                 470                 475                 480

Asn Ile Leu Asn Pro Lys Asp Gly Lys Pro Val Val Thr Pro Ser Gln
                485                 490                 495

Asp Met Val Leu Gly Asn Tyr Tyr Leu Thr Met Glu Arg Glu Gly Ala
            500                 505                 510
```

-continued

```
Ile Gly Glu Gly Met Val Phe Lys Asp Thr Asp Glu Ala Leu Leu Ala
        515                 520                 525

Tyr His Asn Gly Tyr Val His Leu His Ser Arg Ile Ala Ile His Ala
    530                 535                 540

Gly Ser Leu Lys Asn Glu Thr Phe Thr Glu Glu Gln Asn Asn Lys Leu
545                 550                 555                 560

Leu Leu Thr Thr Val Gly Lys Leu Ile Phe Asn Glu Ile Leu Pro Asn
                565                 570                 575

Ser Phe Pro Tyr Ile Asn Glu Pro Thr Thr Glu Asn Ile Glu Gly Arg
            580                 585                 590

Thr Pro Asp Lys Tyr Phe Leu Asp Lys Gly Val Asn Val Arg Glu Glu
        595                 600                 605

Ile Arg Lys Arg Glu Leu Val Pro Pro Phe Lys Lys Lys Val Leu Gly
    610                 615                 620

Gln Ile Ile Ala Glu Val Phe Lys Arg Phe Lys Ile Thr Glu Thr Ser
625                 630                 635                 640

Lys Met Leu Asp Arg Met Lys Asp Leu Gly Phe Gln Tyr Ser Thr Lys
                645                 650                 655

Ala Gly Ile Thr Ile Gly Val Ala Asp Ile Val Val Leu Pro Glu Lys
            660                 665                 670

Gln Glu Ile Leu Asp Glu Ala Gln Ala Lys Val Asp Thr Val Leu Lys
        675                 680                 685

Gln Phe Arg Arg Gly Leu Ile Thr Asp Glu Glu Arg Tyr Glu Arg Val
    690                 695                 700

Ile Ser Ile Trp Ser Ala Ala Lys Asp Lys Ile Gln Asp Arg Leu Met
705                 710                 715                 720

Lys Ser Leu Asp Lys Arg Asn Pro Ile Phe Met Met Ser Asp Ser Gly
                725                 730                 735

Ala Arg Gly Asn Ala Ser Asn Phe Thr Gln Leu Ala Gly Met Arg Gly
            740                 745                 750

Leu Met Ala Asn Pro Ala Gly Arg Ile Ile Glu Leu Pro Ile Lys Ser
        755                 760                 765

Ser Phe Arg Glu Gly Leu Thr Val Leu Glu Tyr Phe Ile Ser Thr His
    770                 775                 780

Gly Ala Arg Lys Gly Leu Ala Asp Thr Ala Leu Lys Thr Ala Asp Ser
785                 790                 795                 800

Gly Tyr Leu Thr Arg Arg Leu Val Asp Val Ala Gln Asp Val Ile Val
                805                 810                 815

Arg Glu Glu Asp Cys Gly Thr Asp Arg Gly Ile Leu Ala Arg Ala Leu
            820                 825                 830

Thr Asp Gly Thr Glu Val Val Val Lys Leu Glu Glu Arg Leu Val Gly
        835                 840                 845

Arg Tyr Ala His Lys Thr Val Arg His Pro Glu Thr Gly Glu Val Ile
    850                 855                 860

Val Arg Lys Asp Glu Met Ile Thr Glu Asp Ile Ala Asn Glu Ile Ile
865                 870                 875                 880

Lys Ala Gly Ile Thr Glu Val Trp Ile Arg Ser Val Phe Ala Cys Asn
                885                 890                 895

Thr Arg His Gly Val Cys Lys Lys Cys Tyr Gly Arg Asn Met Ala Thr
            900                 905                 910

Gly Met Asp Val Glu Val Gly Glu Ala Val Gly Ile Ile Ala Ala Gln
        915                 920                 925

Ser Ile Gly Glu Pro Gly Thr Gln Leu Thr Met Arg Thr Phe His Thr
```

-continued

```
    930                 935                 940

Gly Gly Val Ala Gly Asp Asp Ile Thr Gln Gly Leu Pro Arg Val Gln
945                 950                 955                 960

Glu Leu Phe Glu Ala Arg Asn Pro Lys Gly Gln Ala Val Ile Ser Glu
                965                 970                 975

Ile Asp Gly Thr Val Ile Ser Ile Asn Glu Thr Arg Asp Asn Gln Tyr
            980                 985                 990

Glu Ile Val Val Gln Ser Glu Val  Glu Thr Arg Thr Tyr  Val Ala Pro
        995                 1000                1005

Tyr Asn  Ala Arg Leu Lys Val  Glu Glu Gly Gln Arg  Val Glu Arg
    1010                1015                1020

Gly Gln  Glu Leu Thr Glu Gly  Ser Val Asp Pro Lys  Gln Leu Leu
    1025                1030                1035

Arg Val  Arg Asp Ile Thr Ser  Val Gln Glu Tyr Leu  Leu Arg Glu
    1040                1045                1050

Val Gln  Lys Val Tyr Arg Met  Gln Gly Val Glu Ile  Ser Asp Lys
    1055                1060                1065

His Ile  Glu Val Met Val Arg  Gln Met Leu Arg Lys  Val Arg Val
    1070                1075                1080

Ile Asp  Ala Gly Asp Thr Asp  Val Leu Pro Gly Thr  Leu Leu Asp
    1085                1090                1095

Val His  Gln Phe Thr Asp Val  Asn Ala Lys Ala Leu  Arg Glu Gly
    1100                1105                1110

Lys Arg  Pro Ala Thr Ala Arg  Gln Val Leu Leu Gly  Ile Thr Lys
    1115                1120                1125

Ala Ser  Leu Glu Thr Asp Ser  Phe Leu Ser Ala Ala  Ser Phe Gln
    1130                1135                1140

Glu Thr  Thr Arg Val Leu Thr  Asp Ala Ala Ile Lys  Gly Lys Arg
    1145                1150                1155

Asp Glu  Leu Leu Gly Leu Lys  Glu Asn Val Ile Ile  Gly Lys Leu
    1160                1165                1170

Val Pro  Ala Gly Thr Gly Met  Ala Arg Tyr Arg Lys  Val Lys Pro
    1175                1180                1185

Ala Val  Lys Lys Glu Thr Ala  Gly Gly Thr Val Ser  Ser Lys Gly
    1190                1195                1200

Arg Arg  Ala Ala
    1205


<210> SEQ ID NO 4
<211> LENGTH: 1207
<212> TYPE: PRT
<213> ORGANISM: Geobacillus Stearothermphilus

<400> SEQUENCE: 4

Ser Gly Ser Ser Met Leu Asp Val Asn Lys Phe Glu Tyr Met Lys Ile
1               5                   10                  15

Gly Leu Ala Ser Pro Glu Lys Ile Arg Ser Trp Ser Tyr Gly Glu Val
            20                  25                  30

Lys Lys Pro Glu Thr Ile Asn Tyr Arg Thr Leu Lys Pro Glu Lys Asp
        35                  40                  45

Gly Leu Phe Cys Glu Arg Ile Phe Gly Pro Thr Lys Asp Trp Glu Cys
    50                  55                  60

His Cys Gly Lys Tyr Lys Arg Val Arg Tyr Lys Gly Val Val Cys Asp
65                  70                  75                  80
```

-continued

```
Arg Cys Gly Val Glu Val Thr Arg Ser Lys Val Arg Arg Glu Arg Met
                85                  90                  95

Gly His Ile Glu Leu Ala Ala Pro Val Ser His Ile Trp Tyr Phe Lys
            100                 105                 110

Gly Ile Pro Ser Arg Met Gly Leu Val Leu Asp Met Ser Pro Arg Ala
        115                 120                 125

Leu Glu Glu Val Ile Tyr Phe Ala Ser Tyr Val Val Thr Asp Pro Gly
    130                 135                 140

Asp Thr Pro Leu Glu Lys Lys Gln Leu Leu Ser Glu Lys Glu Tyr Arg
145                 150                 155                 160

Ala Tyr Arg Glu Lys Tyr Gly Gln Ser Phe Gln Ala Ser Met Gly Ala
                165                 170                 175

Glu Ala Ile Lys Lys Leu Leu Gln Asp Ile Asp Leu Asp Lys Glu Val
            180                 185                 190

Ala Ala Leu Lys Glu Glu Leu Lys Thr Ala Gln Gly Gln Arg Arg Ala
        195                 200                 205

Arg Ile Ile Lys Arg Leu Glu Val Leu Glu Ala Phe Arg Ser Ser Gly
    210                 215                 220

Asn Asp Pro Ala Trp Met Val Leu Asp Val Leu Pro Val Ile Pro Pro
225                 230                 235                 240

Glu Leu Arg Pro Met Val Gln Leu Asp Gly Gly Arg Phe Ala Thr Ser
                245                 250                 255

Asp Leu Asn Asp Leu Tyr Arg Arg Val Ile Asn Arg Asn Asn Arg Leu
            260                 265                 270

Lys Arg Leu Leu Asp Leu Gly Ala Pro Asn Ile Ile Val Gln Asn Glu
        275                 280                 285

Lys Arg Met Leu Gln Glu Ala Val Asp Ala Leu Ile Asp Asn Gly Arg
    290                 295                 300

Arg Gly Arg Pro Val Thr Gly Pro Gly Asn Arg Pro Leu Lys Ser Leu
305                 310                 315                 320

Ser His Met Leu Lys Gly Lys Lys Gly Arg Phe Arg Gln Asn Leu Leu
                325                 330                 335

Gly Lys Arg Val Asp Tyr Ser Gly Arg Ser Val Ile Val Val Gly Pro
            340                 345                 350

Asn Leu Lys Met Tyr Gln Cys Gly Leu Pro Lys Glu Met Ala Leu Glu
        355                 360                 365

Leu Phe Lys Pro Phe Val Met Lys Glu Leu Val Glu Arg Gly Leu Ala
    370                 375                 380

His Asn Ile Lys Ser Ala Lys Arg Lys Ile Glu Arg Val His Pro Glu
385                 390                 395                 400

Val Trp Asp Val Leu Glu Asp Val Ile Lys Glu His Pro Val Leu Asn
                405                 410                 415

Arg Ala Pro Thr Leu His Arg Leu Gly Ile Gln Ala Phe Glu Pro Thr
            420                 425                 430

Leu Val Glu Gly Arg Ala Ile Arg Leu His Pro Leu Val Cys Thr Ala
        435                 440                 445

Tyr Asn Ala Asp Phe Asp Gly Asp Gln Met Ala Val His Val Pro Leu
    450                 455                 460

Ser Ala Glu Ala Gln Ala Glu Ala Arg Leu Leu Met Leu Ala Ala Gln
465                 470                 475                 480

Asn Ile Leu Asn Pro Lys Asp Gly Lys Pro Val Val Thr Pro Ser Gln
                485                 490                 495

Asp Met Val Leu Gly Asn Tyr Tyr Leu Thr Met Glu Arg Glu Gly Ala
```

-continued

```
            500                 505                 510

Ile Gly Glu Gly Met Val Phe Lys Asp Thr Asp Glu Ala Leu Leu Ala
        515                 520                 525

Tyr His Asn Gly Tyr Val His Leu His Ser Arg Ile Ala Ile His Ala
    530                 535                 540

Gly Ser Leu Lys Asn Glu Thr Phe Thr Glu Glu Gln Asn Asn Lys Leu
545                 550                 555                 560

Leu Leu Thr Thr Val Gly Lys Leu Ile Phe Asn Glu Ile Leu Pro Asn
                565                 570                 575

Ser Phe Pro Tyr Ile Asn Glu Pro Thr Thr Glu Asn Ile Glu Gly Arg
            580                 585                 590

Thr Pro Asp Lys Tyr Phe Leu Asp Lys Gly Val Asn Val Arg Glu Glu
        595                 600                 605

Ile Arg Lys Arg Glu Leu Val Pro Pro Phe Lys Lys Lys Val Leu Gly
    610                 615                 620

Gln Ile Ile Ala Glu Val Phe Lys Arg Phe Lys Ile Thr Glu Thr Ser
625                 630                 635                 640

Lys Met Leu Asp Arg Met Lys Asp Leu Gly Phe Gln Tyr Ser Thr Lys
                645                 650                 655

Ala Gly Ile Thr Ile Gly Val Ala Asp Ile Val Val Leu Pro Glu Lys
            660                 665                 670

Gln Glu Ile Leu Asp Glu Ala Gln Ala Lys Val Asp Thr Val Leu Lys
        675                 680                 685

Gln Phe Arg Arg Gly Leu Ile Thr Asp Glu Glu Arg Tyr Glu Arg Val
    690                 695                 700

Ile Ser Ile Trp Ser Ala Ala Lys Asp Lys Ile Gln Asp Arg Leu Met
705                 710                 715                 720

Lys Ser Leu Asp Lys Arg Asn Pro Ile Phe Met Met Ser Asp Ser Gly
                725                 730                 735

Ala Arg Gly Asn Ala Ser Asn Phe Thr Gln Leu Ala Gly Met Arg Gly
            740                 745                 750

Leu Met Ala Asn Pro Ala Gly Arg Ile Ile Glu Leu Pro Ile Lys Ser
        755                 760                 765

Ser Phe Arg Glu Gly Leu Thr Val Leu Glu Tyr Phe Ile Ser Thr His
    770                 775                 780

Gly Ala Arg Lys Gly Leu Ala Asp Thr Ala Leu Lys Thr Ala Asp Ser
785                 790                 795                 800

Gly Tyr Leu Thr Arg Arg Leu Val Asp Val Ala Gln Asp Val Ile Val
                805                 810                 815

Arg Glu Glu Asp Cys Gly Thr Asp Arg Gly Ile Leu Ala Arg Ala Leu
            820                 825                 830

Thr Asp Gly Thr Glu Val Val Val Lys Leu Glu Glu Arg Leu Val Gly
        835                 840                 845

Arg Tyr Ala His Lys Thr Val Arg His Pro Glu Thr Gly Glu Val Ile
    850                 855                 860

Val Arg Lys Asp Glu Met Ile Thr Glu Asp Ile Ala Asn Glu Ile Ile
865                 870                 875                 880

Lys Ala Gly Ile Thr Glu Val Trp Ile Arg Ser Val Phe Ala Cys Asn
                885                 890                 895

Thr Arg His Gly Val Cys Lys Lys Cys Tyr Gly Arg Asn Met Ala Thr
            900                 905                 910

Gly Met Asp Val Glu Val Gly Glu Ala Val Gly Ile Ile Ala Ala Gln
        915                 920                 925
```

Ser Ile Gly Glu Pro Gly Thr Gln Leu Thr Met Arg Thr Phe His Thr
930 935 940

Gly Gly Val Ala Gly Asp Asp Ile Thr Gln Gly Leu Pro Arg Val Gln
945 950 955 960

Glu Leu Phe Glu Ala Arg Asn Pro Lys Gly Gln Ala Val Ile Ser Glu
965 970 975

Ile Asp Gly Thr Val Ile Ser Ile Asn Glu Thr Arg Asp Asn Gln Tyr
980 985 990

Glu Ile Val Val Gln Ser Glu Val Glu Thr Arg Thr Tyr Val Ala Pro
995 1000 1005

Tyr Asn Ala Arg Leu Lys Val Glu Glu Gly Gln Arg Val Glu Arg
1010 1015 1020

Gly Gln Glu Leu Thr Glu Gly Ser Val Asp Pro Lys Gln Leu Leu
1025 1030 1035

Arg Val Arg Asp Ile Thr Ser Val Gln Glu Tyr Leu Leu Arg Glu
1040 1045 1050

Val Gln Lys Val Tyr Arg Met Gln Gly Val Glu Ile Ser Asp Lys
1055 1060 1065

His Ile Glu Val Met Val Arg Gln Met Leu Arg Lys Val Arg Val
1070 1075 1080

Ile Asp Ala Gly Asp Thr Asp Val Leu Pro Gly Thr Leu Leu Asp
1085 1090 1095

Val His Gln Phe Thr Asp Val Asn Ala Lys Ala Leu Arg Glu Gly
1100 1105 1110

Lys Arg Pro Ala Thr Ala Arg Gln Val Leu Leu Gly Ile Thr Lys
1115 1120 1125

Ala Ser Leu Glu Thr Asp Ser Phe Leu Ser Ala Ala Ser Phe Gln
1130 1135 1140

Glu Thr Thr Arg Val Leu Thr Asp Ala Ala Ile Lys Gly Lys Arg
1145 1150 1155

Asp Glu Leu Leu Gly Leu Lys Glu Asn Val Ile Ile Gly Lys Leu
1160 1165 1170

Val Pro Ala Gly Thr Gly Met Ala Arg Tyr Arg Lys Val Lys Pro
1175 1180 1185

Ala Val Lys Lys Glu Thr Ala Gly Gly Thr Val Ser Ser Lys Gly
1190 1195 1200

Arg Arg Ala Ala
1205

<210> SEQ ID NO 5
<211> LENGTH: 193
<212> TYPE: PRT
<213> ORGANISM: Geobacillus Stearothermphilus

<400> SEQUENCE: 5

Ser Gly Ser Ser Met Ser Leu Gln Gln Gln Tyr Ser Pro Glu Glu Leu
1 5 10 15

Gln Glu Met Ser Phe Val Glu Leu Ala Asn Leu Ile Leu Leu Asp Lys
20 25 30

Arg Glu Ala Leu Pro Phe Asp Gln Leu Val Arg Glu Ala Ala Ala Leu
35 40 45

Ala Gly Ile Ser Glu Glu Glu Met Glu Ala Arg Leu Ala Gln Tyr Tyr
50 55 60

Thr Asp Leu Asn Ile Asp Gly Arg Phe Ile Cys Val Gly Glu Asn Val

```
65                  70                  75                  80

Trp Gly Arg Ala Trp Tyr Pro Phe Asp Gln Thr Glu Asp Glu Thr Val
                85                  90                  95

Thr Ile Val Lys Pro Lys Lys Lys Lys Lys Ala Leu Asp Asp Glu Tyr
            100                 105                 110

Asp Glu Tyr Asp Glu Leu Leu Glu Asp Glu Asp Leu Asp Tyr Asp Asp
        115                 120                 125

Leu Asp Glu Tyr Asp Glu Glu Leu Glu Leu Asp Glu Asp Glu Leu
    130                 135                 140

Leu Glu Asp Glu Glu Phe Asp Leu Asp Glu Asp Val Ala Phe Asp Asp
145                 150                 155                 160

Asp Ile Leu Gly Asp Glu Glu Phe Glu Leu Gly Asp Ala Pro Leu Asp
                165                 170                 175

Glu Glu Leu Asp Leu Glu Glu Pro Glu Glu Asp Glu Gly Arg Arg Ala
            180                 185                 190

Ala


<210> SEQ ID NO 6
<211> LENGTH: 75
<212> TYPE: PRT
<213> ORGANISM: Geobacillus Stearothermphilus

<400> SEQUENCE: 6

Ser Gly Ser Ser Met Leu Tyr Pro Ser Ile Asp Leu Leu Met Gln Lys
1               5                   10                  15

Val Asp Ser Lys Tyr Lys Leu Val Thr Val Val Ala Lys Arg Ala Arg
            20                  25                  30

Glu Leu Gln Asp Gly Ala Glu Leu Met Val Lys Lys Pro Val Ser Lys
        35                  40                  45

Lys Phe Val Gly Gln Ala Leu Glu Glu Ile Ala Gly Asp Lys Val Glu
    50                  55                  60

Leu Val Glu Glu Glu Lys Gly Arg Arg Ala Ala
65                  70                  75


<210> SEQ ID NO 7
<211> LENGTH: 408
<212> TYPE: PRT
<213> ORGANISM: Geobacillus Stearothermphilus

<400> SEQUENCE: 7

Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
            20                  25                  30

Thr Met Ala Glu Lys Pro Ala Gln Ser Lys Gln Ala Glu Ala Ala Gly
        35                  40                  45

Glu Ser Leu Glu Gln Val Lys Glu Gln Leu Ala Glu Leu Gly Lys Lys
    50                  55                  60

Arg Gly Ile Leu Thr Tyr Glu Glu Ile Ala Glu Arg Leu Ser Gly Phe
65                  70                  75                  80

Asp Leu Asp Ser Asp Gln Met Asp Glu Tyr Tyr Glu Tyr Leu Ala Glu
                85                  90                  95

Gln Gly Ile Glu Val Ile Ser Glu Ser Asp Leu Glu Ala Asp Pro Asp
            100                 105                 110

Ile Asp Asp Leu Ala Lys Glu Glu Glu Phe Asp Leu Asn Asp Leu Ser
        115                 120                 125
```

-continued

```
Val Pro Pro Gly Val Lys Ile Asn Asp Pro Val Arg Met Tyr Leu Lys
    130                 135                 140

Glu Ile Gly Arg Val Pro Leu Leu Ser Ala Glu Glu Glu Ile Glu Leu
145                 150                 155                 160

Ala Lys Arg Ile Glu Gln Gly Asp Glu Glu Ala Lys Arg Arg Leu Thr
                165                 170                 175

Glu Ala Asn Leu Arg Leu Val Val Ser Ile Ala Lys Arg Tyr Val Gly
            180                 185                 190

Arg Gly Met Leu Phe Leu Asp Leu Ile Gln Glu Gly Asn Met Gly Leu
        195                 200                 205

Ile Lys Ala Val Glu Lys Phe Asp Tyr Arg Lys Gly Tyr Lys Phe Ser
    210                 215                 220

Thr Tyr Ala Thr Trp Trp Ile Arg Gln Ala Ile Thr Arg Ala Ile Ala
225                 230                 235                 240

Asp Gln Ala Arg Thr Ile Arg Ile Pro Val His Met Val Glu Thr Ile
                245                 250                 255

Asn Lys Leu Ile Arg Val Gln Arg Gln Leu Leu Gln Asp Leu Gly Arg
            260                 265                 270

Glu Pro Thr Pro Glu Glu Ile Ala Glu Glu Met Asp Leu Thr Pro Glu
        275                 280                 285

Lys Val Arg Glu Ile Leu Lys Ile Ala Gln Glu Pro Val Ser Leu Glu
    290                 295                 300

Thr Pro Ile Gly Glu Glu Asp Asp Ser His Leu Gly Asp Phe Ile Glu
305                 310                 315                 320

Asp Gln Asp Ala Thr Ser Pro Ser Glu His Ala Ala Tyr Glu Leu Leu
                325                 330                 335

Lys Glu Gln Leu Glu Asp Val Leu Asp Thr Leu Thr Asp Arg Glu Glu
            340                 345                 350

Asn Val Leu Arg Leu Arg Phe Gly Leu Asp Asp Gly Arg Thr Arg Thr
        355                 360                 365

Leu Glu Glu Val Gly Lys Val Phe Gly Val Thr Arg Glu Arg Ile Arg
    370                 375                 380

Gln Ile Glu Ala Lys Ala Leu Arg Lys Leu Arg His Pro Ser Arg Ser
385                 390                 395                 400

Lys Arg Leu Lys Asp Phe Leu Glu
                405


<210> SEQ ID NO 8
<211> LENGTH: 224
<212> TYPE: PRT
<213> ORGANISM: Geobacillus Stearothermphilus

<400> SEQUENCE: 8

Ser Gly Ser Ser Met Asn Leu Val Leu Met Gly Leu Pro Gly Ala Gly
1               5                   10                  15

Lys Gly Thr Gln Ala Gly Lys Ile Val Glu Ala Tyr Gly Ile Pro His
            20                  25                  30

Ile Ser Thr Gly Asp Met Phe Arg Ala Ala Ile Lys Glu Gly Thr Pro
        35                  40                  45

Leu Gly Leu Gln Ala Lys Gln Tyr Met Asp Arg Gly Asp Leu Val Pro
    50                  55                  60

Asp Glu Leu Gln Ala Lys Gln Tyr Met Asp Arg Gly Asp Leu Val Pro
65                  70                  75                  80

Asp Glu Gly Phe Leu Leu Asp Gly Phe Pro Arg Thr Val Ala Gln Ala
```

-continued

```
                85                  90                  95

Glu Ala Leu Glu Thr Leu Leu Ser Glu Ile Gly Arg Lys Leu Asp Tyr
            100                 105                 110

Val Ile His Ile Asp Val Arg Gln Glu Val Leu Met Glu Arg Leu Thr
        115                 120                 125

Gly Arg Arg Ile Cys Arg Asn Cys Gly Ala Thr Tyr His Leu Val Phe
    130                 135                 140

His Pro Pro Ala Lys Pro Gly Val Cys Asp Lys Cys Gly Gly Asp Leu
145                 150                 155                 160

Tyr Gln Arg Pro Asp Asn Glu Ala Thr Val Ala Asn Arg Leu Glu Val
                165                 170                 175

Asn Met Lys Gln Met Lys Leu Leu Leu Asp Phe Tyr Glu Gln Lys Gly
            180                 185                 190

Tyr Leu Arg His Ile Asn Gly Glu Gln Glu Met Glu Lys Val Phe Ala
        195                 200                 205

Asp Ile Cys Glu Val Leu Gly Gly Leu Ala Arg Gly Arg Arg Ala Ala
    210                 215                 220


<210> SEQ ID NO 9
<211> LENGTH: 697
<212> TYPE: PRT
<213> ORGANISM: Escherichia Coli

<400> SEQUENCE: 9

Ser Gly Ser Ser Met Gly Gln Glu Lys Leu Tyr Ile Glu Lys Glu Leu
1               5                   10                  15

Ser Trp Leu Ser Phe Asn Glu Arg Val Leu Gln Glu Ala Ala Asp Lys
            20                  25                  30

Ser Asn Pro Leu Ile Glu Arg Met Arg Phe Leu Gly Ile Tyr Ser Asn
        35                  40                  45

Asn Leu Asp Glu Phe Tyr Lys Val Arg Phe Ala Glu Leu Lys Arg Arg
    50                  55                  60

Ile Ile Ile Ser Glu Glu Gln Gly Ser Asn Ser His Ser Arg His Leu
65                  70                  75                  80

Leu Gly Lys Ile Gln Ser Arg Val Leu Lys Ala Asp Gln Glu Phe Asp
                85                  90                  95

Gly Leu Tyr Asn Glu Leu Leu Leu Glu Met Ala Arg Asn Gln Ile Phe
            100                 105                 110

Leu Ile Asn Glu Arg Gln Leu Ser Val Asn Gln Gln Asn Trp Leu Arg
        115                 120                 125

His Tyr Phe Lys Gln Tyr Leu Arg Gln His Ile Thr Pro Ile Leu Ile
    130                 135                 140

Asn Pro Asp Thr Asp Leu Val Gln Phe Leu Lys Asp Asp Tyr Thr Tyr
145                 150                 155                 160

Leu Ala Val Glu Ile Ile Arg Gly Asp Thr Ile Arg Tyr Ala Leu Leu
                165                 170                 175

Glu Ile Pro Ser Asp Lys Val Pro Arg Phe Val Asn Leu Pro Pro Glu
            180                 185                 190

Ala Pro Arg Arg Arg Lys Pro Met Ile Leu Leu Asp Asn Ile Leu Arg
        195                 200                 205

Tyr Cys Leu Asp Asp Ile Phe Lys Gly Phe Phe Asp Tyr Asp Ala Leu
    210                 215                 220

Asn Ala Tyr Ser Met Lys Met Thr Arg Asp Ala Glu Tyr Asp Leu Val
225                 230                 235                 240
```

-continued

```
His Glu Met Glu Ala Ser Leu Met Glu Leu Met Ser Ser Ser Leu Lys
                245                 250                 255

Gln Arg Leu Thr Ala Glu Pro Val Arg Phe Val Tyr Gln Arg Asp Met
            260                 265                 270

Pro Asn Ala Leu Val Glu Val Leu Arg Glu Lys Leu Thr Ile Ser Arg
        275                 280                 285

Tyr Asp Ser Ile Val Pro Gly Gly Arg Tyr His Asn Phe Lys Asp Phe
    290                 295                 300

Ile Asn Phe Pro Asn Val Gly Lys Ala Asn Leu Val Asn Lys Pro Leu
305                 310                 315                 320

Pro Arg Leu Arg His Ile Trp Phe Asp Lys Ala Gln Phe Arg Asn Gly
                325                 330                 335

Phe Asp Ala Ile Arg Glu Arg Asp Val Leu Leu Tyr Tyr Pro Tyr His
            340                 345                 350

Thr Phe Glu His Val Leu Glu Leu Leu Arg Gln Ala Ser Phe Asp Pro
        355                 360                 365

Ser Val Leu Ala Ile Lys Ile Asn Ile Tyr Arg Val Ala Lys Asp Ser
    370                 375                 380

Arg Ile Ile Asp Ser Met Ile His Ala Ala His Asn Gly Lys Lys Val
385                 390                 395                 400

Thr Val Val Val Glu Leu Gln Ala Arg Phe Asp Glu Glu Ala Asn Ile
                405                 410                 415

His Trp Ala Lys Arg Leu Thr Glu Ala Gly Val His Val Ile Phe Ser
            420                 425                 430

Ala Pro Gly Leu Lys Ile His Ala Lys Leu Phe Leu Ile Ser Arg Lys
        435                 440                 445

Glu Asn Gly Glu Val Val Arg Tyr Ala His Ile Gly Thr Gly Asn Phe
    450                 455                 460

Asn Glu Lys Thr Ala Arg Leu Tyr Thr Asp Tyr Ser Leu Leu Thr Ala
465                 470                 475                 480

Asp Ala Arg Ile Thr Asn Glu Val Arg Arg Val Phe Asn Phe Ile Glu
                485                 490                 495

Asn Pro Tyr Arg Pro Val Thr Phe Asp Tyr Leu Met Val Ser Pro Gln
            500                 505                 510

Asn Ser Arg Arg Leu Leu Tyr Glu Met Val Asp Arg Glu Ile Ala Asn
        515                 520                 525

Ala Gln Gln Gly Leu Pro Ser Gly Ile Thr Leu Lys Leu Asn Asn Leu
    530                 535                 540

Val Asp Lys Gly Leu Val Asp Arg Leu Tyr Ala Ala Ser Ser Ser Gly
545                 550                 555                 560

Val Pro Val Asn Leu Leu Val Arg Gly Met Cys Ser Leu Ile Pro Asn
                565                 570                 575

Leu Glu Gly Ile Ser Asp Asn Ile Arg Ala Ile Ser Ile Val Asp Arg
            580                 585                 590

Tyr Leu Glu His Asp Arg Val Tyr Ile Phe Glu Asn Gly Gly Asp Lys
        595                 600                 605

Lys Val Tyr Leu Ser Ser Ala Asp Trp Met Thr Arg Asn Ile Asp Tyr
    610                 615                 620

Arg Ile Glu Val Ala Thr Pro Leu Leu Asp Pro Arg Leu Lys Gln Arg
625                 630                 635                 640

Val Leu Asp Ile Ile Asp Ile Leu Phe Ser Asp Thr Val Lys Ala Arg
                645                 650                 655

Tyr Ile Asp Lys Glu Leu Ser Asn Arg Tyr Val Pro Arg Gly Asn Arg
```

660 665 670

Arg Lys Val Arg Ala Gln Leu Ala Ile Tyr Asp Tyr Ile Lys Ser Leu
675 680 685

Glu Gln Pro Glu Gly Arg Arg Ala Ala
690 695

<210> SEQ ID NO 10
<211> LENGTH: 608
<212> TYPE: PRT
<213> ORGANISM: Thermus aquaticus

<400> SEQUENCE: 10

Met Arg Leu Leu Pro Glu Glu Ser Trp Leu Gln Phe Asn Arg Arg Val
1 5 10 15

Leu Arg Gln Ser Glu Arg Pro Asp Phe Pro Leu Leu Glu Arg Met Arg
20 25 30

Phe Leu Ala Ile Trp Asn Arg Asn Leu Asp Glu Phe Phe Ala Ala Arg
35 40 45

Ile Ala Lys Pro Phe Leu Lys His Arg Gly Ser Ala His Leu Arg Leu
50 55 60

Leu Lys Glu Ala Glu Asp Gln Ala Arg Leu Ala Glu Gly Arg Tyr Arg
65 70 75 80

Ala Leu Leu Ala Glu Ala Ala Pro His Leu Lys Ile Leu Glu Pro Glu
85 90 95

Glu Leu Asp Asp Leu Asp Trp Leu Tyr Phe Arg Val Phe Leu Ala Glu
100 105 110

Val Val Val Pro Lys Thr Asp Leu Ile Ala Trp Glu Ala Ala Lys Glu
115 120 125

Ala Ser His Gly Ala Leu Tyr Phe Ala Ser Glu Asp His Leu Val Arg
130 135 140

Leu Pro Gln Asp Leu Pro Arg Leu Leu Lys Val Pro Gly Arg Glu Gly
145 150 155 160

Thr Tyr Val Arg Leu Gly Ala Leu Met Arg Ala Arg Ser Asp Leu Phe
165 170 175

Leu Pro Arg Glu Ser Pro Leu Tyr Glu Phe Arg Val Leu Arg Leu Leu
180 185 190

Glu Ser Glu Arg Ala Arg Ala Asp Trp Asp Glu Leu Ala Gln Ala Leu
195 200 205

Glu Gly Arg Gln Glu Gly Leu Ser Thr Leu Leu Val Ala Glu Arg Gly
210 215 220

Phe Pro Lys Gly Trp Leu Glu Gly Leu Gln Glu Ala Leu Gly Leu Leu
225 230 235 240

Pro Glu Glu Val Ile Leu Leu Ser Pro Pro Leu Asn Leu Thr Leu Val
245 250 255

Glu Thr Leu Val Ala Glu Gly Pro Ser Arg Trp Arg Phe Pro Pro Leu
260 265 270

Glu Pro Lys Arg Pro Arg Ala Phe Met Lys Asn Pro Leu Lys Arg Leu
275 280 285

Gln Glu Lys Asp Leu Val Leu Tyr His Pro Phe Glu Asp Tyr Ala Ala
290 295 300

Leu Glu Arg Phe Ala Glu Ala Ala Leu Ser Glu Glu Val Glu Glu Val
305 310 315 320

Tyr Ala Thr Leu Tyr Arg Ile Gly Glu Ala Asn Pro Leu Ala Glu Ala
325 330 335

-continued

```
Leu Ile Gln Ala Ala Arg Ala Gly Lys Arg Val His Val Leu Leu Glu
            340                 345                 350

Pro Arg Ala Arg Phe Asp Glu Leu Leu Asn Leu Ser Trp Tyr Leu Arg
        355                 360                 365

Phe Leu Arg Ala Gly Val Ala Val Leu Pro Leu Ser Glu Arg Lys Val
    370                 375                 380

His Ala Lys Ala Leu Leu Leu Leu Thr Gln Lys Gly Gly Tyr Ala His
385                 390                 395                 400

Leu Gly Thr Gly Asn Tyr Asn Pro Gln Asn Gly Arg Gln Tyr Thr Asp
                405                 410                 415

Phe Ser Leu Phe Thr Ala Arg Lys Glu Val Val Met Glu Val Ala Glu
            420                 425                 430

Phe Phe Arg Ala Leu Gln Glu Gly Arg Thr Pro Arg Leu Asn Leu Leu
        435                 440                 445

Lys Thr Gly Glu Ala Ile Gln Glu Leu Leu Leu Glu His Ile Arg Ala
    450                 455                 460

Glu Ser His Pro Lys Gly Arg Ile Leu Leu Lys Cys Asn His Leu Thr
465                 470                 475                 480

Asp Pro Ala Leu Leu Glu Ala Leu Ala Arg Ala Ala Asp Lys Gly Ala
                485                 490                 495

Arg Val Asp Leu Ile Val Arg Ser Thr Leu Thr Leu Leu His Pro Arg
            500                 505                 510

Phe Arg Ala Arg Ser Leu Val Gly Arg Phe Leu Glu His Ala Arg Val
        515                 520                 525

Ala Ala Phe Tyr Gln Gly Gly Arg Trp Ala Leu Tyr Leu Thr Ser Ala
    530                 535                 540

Asp Leu Met Pro Arg Asn Phe Gln Asn Arg Phe Glu Leu Leu Phe Pro
545                 550                 555                 560

Val Leu Asp Lys Glu Gly Lys Ala Lys Val Leu Glu Val Leu Lys Arg
                565                 570                 575

Gln Leu Lys Asp Asp Arg Asn Ala Phe Leu Leu Ser Pro Lys Gly Glu
            580                 585                 590

Thr Pro Leu Trp Gly Gly Arg His Asp Ala Gln Arg Ile Leu Ala Trp
        595                 600                 605


<210> SEQ ID NO 11
<211> LENGTH: 641
<212> TYPE: PRT
<213> ORGANISM: Thermus aquaticus

<400> SEQUENCE: 11

Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
            20                  25                  30

Thr Met Arg Leu Leu Pro Glu Glu Ser Trp Leu Gln Phe Asn Arg Arg
        35                  40                  45

Val Leu Arg Gln Ser Glu Arg Pro Asp Phe Pro Leu Leu Glu Arg Met
    50                  55                  60

Arg Phe Leu Ala Ile Trp Asn Arg Asn Leu Asp Glu Phe Phe Ala Ala
65                  70                  75                  80

Arg Ile Ala Lys Pro Phe Leu Lys His Arg Gly Ser Glu Ala His Leu
                85                  90                  95

Arg Leu Leu Lys Glu Ala Glu Asp Gln Ala Arg Leu Ala Glu Gly Arg
            100                 105                 110
```

-continued

```
Tyr Arg Ala Leu Leu Ala Glu Ala Ala Pro His Leu Lys Ile Leu Glu
        115                 120                 125

Pro Glu Glu Leu Asp Asp Leu Asp Trp Leu Tyr Phe Arg Val Phe Leu
    130                 135                 140

Ala Glu Val Val Val Pro Lys Thr Asp Leu Ile Ala Trp Glu Ala Ala
145                 150                 155                 160

Lys Glu Ala Ser His Gly Ala Leu Tyr Phe Ala Ser Glu Asp His Leu
                165                 170                 175

Val Arg Leu Pro Gln Asp Leu Pro Arg Leu Leu Lys Val Pro Gly Arg
            180                 185                 190

Glu Gly Thr Tyr Val Arg Leu Gly Ala Leu Met Arg Ala Arg Ser Asp
        195                 200                 205

Leu Phe Leu Pro Arg Glu Ser Pro Leu Tyr Glu Phe Arg Val Leu Arg
    210                 215                 220

Leu Leu Glu Ser Glu Arg Ala Arg Ala Asp Trp Asp Glu Leu Ala Gln
225                 230                 235                 240

Ala Leu Glu Gly Arg Gln Glu Gly Leu Ser Thr Leu Leu Val Ala Glu
                245                 250                 255

Arg Gly Phe Pro Lys Gly Trp Leu Glu Gly Leu Gln Glu Ala Leu Gly
            260                 265                 270

Leu Leu Pro Glu Glu Val Ile Leu Leu Ser Pro Pro Leu Asn Leu Thr
        275                 280                 285

Leu Val Glu Thr Leu Val Ala Glu Gly Pro Ser Arg Trp Arg Phe Pro
    290                 295                 300

Pro Leu Glu Pro Lys Arg Pro Arg Ala Phe Met Lys Asn Pro Leu Lys
305                 310                 315                 320

Arg Leu Gln Glu Lys Asp Leu Val Leu Tyr His Pro Phe Glu Asp Tyr
                325                 330                 335

Ala Ala Leu Glu Arg Phe Ala Glu Ala Ala Leu Ser Glu Glu Val Glu
            340                 345                 350

Glu Val Tyr Ala Thr Leu Tyr Arg Ile Gly Glu Ala Asn Pro Leu Ala
        355                 360                 365

Glu Ala Leu Ile Gln Ala Ala Arg Ala Gly Lys Arg Val His Val Leu
    370                 375                 380

Leu Glu Pro Arg Ala Arg Phe Asp Glu Leu Leu Asn Leu Ser Trp Tyr
385                 390                 395                 400

Leu Arg Phe Leu Arg Ala Gly Val Ala Val Leu Pro Leu Ser Glu Arg
                405                 410                 415

Lys Val His Ala Lys Ala Leu Leu Leu Leu Thr Gln Lys Gly Gly Tyr
            420                 425                 430

Ala His Leu Gly Thr Gly Asn Tyr Asn Pro Gln Asn Gly Arg Gln Tyr
        435                 440                 445

Thr Asp Phe Ser Leu Phe Thr Ala Arg Lys Glu Val Val Met Glu Val
    450                 455                 460

Ala Glu Phe Phe Arg Ala Leu Gln Glu Gly Arg Thr Pro Arg Leu Asn
465                 470                 475                 480

Leu Leu Lys Thr Gly Glu Ala Ile Gln Glu Leu Leu Leu Glu His Ile
                485                 490                 495

Arg Ala Glu Ser His Pro Lys Gly Arg Ile Leu Leu Lys Cys Asn His
            500                 505                 510

Leu Thr Asp Pro Ala Leu Leu Glu Ala Leu Ala Arg Ala Ala Asp Lys
        515                 520                 525
```

```
Gly Ala Arg Val Asp Leu Ile Val Arg Ser Thr Leu Thr Leu Leu His
    530                 535                 540

Pro Arg Phe Arg Ala Arg Ser Leu Val Gly Arg Phe Leu Glu His Ala
545                 550                 555                 560

Arg Val Ala Ala Phe Tyr Gln Gly Gly Arg Trp Ala Leu Tyr Leu Thr
                565                 570                 575

Ser Ala Asp Leu Met Pro Arg Asn Phe Gln Asn Arg Phe Glu Leu Leu
            580                 585                 590

Phe Pro Val Leu Asp Lys Glu Gly Lys Ala Lys Val Leu Glu Val Leu
        595                 600                 605

Lys Arg Gln Leu Lys Asp Asp Arg Asn Ala Phe Leu Leu Ser Pro Lys
    610                 615                 620

Gly Glu Thr Pro Leu Trp Gly Gly Arg His Asp Ala Gln Arg Ile Ala
625                 630                 635                 640

Trp


<210> SEQ ID NO 12
<211> LENGTH: 457
<212> TYPE: PRT
<213> ORGANISM: Clostridium Tetani

<400> SEQUENCE: 12

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255
```

-continued

```
Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala
    450                 455


<210> SEQ ID NO 13
<211> LENGTH: 8
<212> TYPE: PRT
<213> ORGANISM: Clostridium Tetani

<400> SEQUENCE: 13

Met His Glu Leu Ile His Val Leu
1               5


<210> SEQ ID NO 14
<211> LENGTH: 861
<212> TYPE: PRT
<213> ORGANISM: Clostridium Tetani

<400> SEQUENCE: 14

Ser Leu Thr Asp Leu Gly Gly Glu Leu Cys Ile Lys Ile Lys Asn Glu
1               5                   10                  15

Asp Leu Thr Phe Ile Ala Glu Lys Asn Ser Phe Ser Glu Glu Pro Phe
            20                  25                  30

Gln Asp Glu Ile Val Ser Tyr Asn Thr Lys Asn Lys Pro Leu Asn Phe
        35                  40                  45

Asn Tyr Ser Leu Asp Lys Ile Ile Val Asp Tyr Asn Leu Gln Ser Lys
    50                  55                  60

Ile Thr Leu Pro Asn Asp Arg Thr Thr Pro Val Thr Lys Gly Ile Pro
65                  70                  75                  80

Tyr Ala Pro Glu Tyr Lys Ser Asn Ala Ala Ser Thr Ile Glu Ile His
                85                  90                  95

Asn Ile Asp Asp Asn Thr Ile Tyr Gln Tyr Leu Tyr Ala Gln Lys Ser
            100                 105                 110
```

-continued

```
Pro Thr Thr Leu Gln Arg Ile Thr Met Thr Asn Ser Val Asp Asp Ala
        115                 120                 125

Leu Ile Asn Ser Thr Lys Ile Tyr Ser Tyr Phe Pro Ser Val Ile Ser
    130                 135                 140

Lys Val Asn Gln Gly Ala Gln Gly Ile Leu Phe Leu Gln Trp Val Arg
145                 150                 155                 160

Asp Ile Ile Asp Asp Phe Thr Asn Glu Ser Ser Gln Lys Thr Thr Ile
                165                 170                 175

Asp Lys Ile Ser Asp Val Ser Thr Ile Val Pro Tyr Ile Gly Pro Ala
            180                 185                 190

Leu Asn Ile Val Lys Gln Gly Tyr Glu Gly Asn Phe Ile Gly Ala Leu
        195                 200                 205

Glu Thr Thr Gly Val Val Leu Leu Leu Glu Tyr Ile Pro Glu Ile Thr
    210                 215                 220

Leu Pro Val Ile Ala Ala Leu Ser Ile Ala Glu Ser Ser Thr Gln Lys
225                 230                 235                 240

Glu Lys Ile Ile Lys Thr Ile Asp Asn Phe Leu Glu Lys Arg Tyr Glu
                245                 250                 255

Lys Trp Ile Glu Val Tyr Lys Leu Val Lys Ala Lys Trp Leu Gly Thr
            260                 265                 270

Val Asn Thr Gln Phe Gln Lys Arg Ser Tyr Gln Met Tyr Arg Ser Leu
        275                 280                 285

Glu Tyr Gln Val Asp Ala Ile Lys Lys Ile Ile Asp Tyr Glu Tyr Lys
    290                 295                 300

Ile Tyr Ser Gly Pro Asp Lys Glu Gln Ile Ala Asp Glu Ile Asn Asn
305                 310                 315                 320

Leu Lys Asn Lys Leu Glu Glu Lys Ala Asn Lys Ala Met Ile Asn Ile
                325                 330                 335

Asn Ile Phe Met Arg Glu Ser Ser Arg Ser Phe Leu Val Asn Gln Met
            340                 345                 350

Ile Asn Glu Ala Lys Lys Gln Leu Leu Glu Phe Asp Thr Gln Ser Lys
        355                 360                 365

Asn Ile Leu Met Gln Tyr Ile Lys Ala Asn Ser Lys Phe Ile Gly Ile
    370                 375                 380

Thr Glu Leu Lys Lys Leu Glu Ser Lys Ile Asn Lys Val Phe Ser Thr
385                 390                 395                 400

Pro Ile Pro Phe Ser Tyr Ser Lys Asn Leu Asp Cys Trp Val Asp Asn
                405                 410                 415

Glu Glu Asp Ile Asp Val Ile Leu Lys Lys Ser Thr Ile Leu Asn Leu
            420                 425                 430

Asp Ile Asn Asn Asp Ile Ile Ser Asp Ile Ser Gly Phe Asn Ser Ser
        435                 440                 445

Val Ile Thr Tyr Pro Asp Ala Gln Leu Val Pro Gly Ile Asn Gly Lys
    450                 455                 460

Ala Ile His Leu Val Asn Asn Glu Ser Ser Glu Val Ile Val His Lys
465                 470                 475                 480

Ala Met Asp Ile Glu Tyr Asn Asp Met Phe Asn Asn Phe Thr Val Ser
                485                 490                 495

Phe Trp Leu Arg Val Pro Lys Val Ser Ala Ser His Leu Glu Gln Tyr
            500                 505                 510

Gly Thr Asn Glu Tyr Ser Ile Ile Ser Ser Met Lys Lys His Ser Leu
        515                 520                 525

Ser Ile Gly Ser Gly Trp Ser Val Ser Leu Lys Gly Asn Asn Leu Ile
```

```
    530                 535                 540

Trp Thr Leu Lys Asp Ser Ala Gly Glu Val Arg Gln Ile Thr Phe Arg
545                 550                 555                 560

Asp Leu Pro Asp Lys Phe Asn Ala Tyr Leu Ala Asn Lys Trp Val Phe
                565                 570                 575

Ile Thr Ile Thr Asn Asp Arg Leu Ser Ser Ala Asn Leu Tyr Ile Asn
            580                 585                 590

Gly Val Leu Met Gly Ser Ala Glu Ile Thr Gly Leu Gly Ala Ile Arg
        595                 600                 605

Glu Asp Asn Asn Ile Thr Leu Lys Leu Asp Arg Cys Asn Asn Asn Asn
    610                 615                 620

Gln Tyr Val Ser Ile Asp Lys Phe Arg Ile Phe Cys Lys Ala Leu Asn
625                 630                 635                 640

Pro Lys Glu Ile Glu Lys Leu Tyr Thr Ser Tyr Leu Ser Ile Thr Phe
                645                 650                 655

Leu Arg Asp Phe Trp Gly Asn Pro Leu Arg Tyr Asp Thr Glu Tyr Tyr
            660                 665                 670

Leu Ile Pro Val Ala Ser Ser Ser Lys Asp Val Gln Leu Lys Asn Ile
        675                 680                 685

Thr Asp Tyr Met Tyr Leu Thr Asn Ala Pro Ser Tyr Thr Asn Gly Lys
    690                 695                 700

Leu Asn Ile Tyr Tyr Arg Arg Leu Tyr Asn Gly Leu Lys Phe Ile Ile
705                 710                 715                 720

Lys Arg Tyr Thr Pro Asn Asn Glu Ile Asp Ser Phe Val Lys Ser Gly
                725                 730                 735

Asp Phe Ile Lys Leu Tyr Val Ser Tyr Asn Asn Asn Glu His Ile Val
            740                 745                 750

Gly Tyr Pro Lys Asp Gly Asn Ala Phe Asn Asn Leu Asp Arg Ile Leu
        755                 760                 765

Arg Val Gly Tyr Asn Ala Pro Gly Ile Pro Leu Tyr Lys Lys Met Glu
    770                 775                 780

Ala Val Lys Leu Arg Asp Leu Lys Thr Tyr Ser Val Gln Leu Lys Leu
785                 790                 795                 800

Tyr Asp Asp Lys Asn Ala Ser Leu Gly Leu Val Gly Thr His Asn Gly
                805                 810                 815

Gln Ile Gly Asn Asp Pro Asn Arg Asp Ile Leu Ile Ala Ser Asn Trp
            820                 825                 830

Tyr Phe Asn His Leu Lys Asp Lys Ile Leu Gly Cys Asp Trp Tyr Phe
        835                 840                 845

Val Pro Thr Asp Glu Gly Trp Thr Asn Asp Gly Ser Ala
    850                 855                 860


<210> SEQ ID NO 15
<211> LENGTH: 7
<212> TYPE: PRT
<213> ORGANISM: Artificial Sequence
<220> FEATURE:
<223> OTHER INFORMATION: TEV site

<400> SEQUENCE: 15

Glu Asn Leu Tyr Phe Gln Ser
1               5


<210> SEQ ID NO 16
<211> LENGTH: 252
<212> TYPE: PRT
```

<213> ORGANISM: Artificial Sequence
<220> FEATURE:
<223> OTHER INFORMATION: mCherry-His6

<400> SEQUENCE: 16

```
Gly Ser Gly Ser Asn Gly Ser Ser Gly Ser Val Ser Met Ala Ile Ile
1               5                   10                  15

Lys Glu Phe Met Arg Phe Lys Val His Met Glu Gly Ser Val Asn Gly
            20                  25                  30

His Glu Phe Glu Ile Glu Gly Glu Gly Glu Gly Arg Pro Tyr Glu Gly
        35                  40                  45

Thr Gln Thr Ala Lys Leu Lys Val Thr Lys Gly Gly Pro Leu Pro Phe
    50                  55                  60

Ala Trp Asp Ile Leu Ser Pro Gln Phe Met Tyr Gly Ser Lys Ala Tyr
65                  70                  75                  80

Val Lys His Pro Ala Asp Ile Pro Asp Tyr Leu Lys Leu Ser Phe Pro
                85                  90                  95

Glu Gly Phe Lys Trp Glu Arg Val Met Asn Phe Glu Asp Gly Gly Val
            100                 105                 110

Val Thr Val Thr Gln Asp Ser Ser Leu Gln Asp Gly Glu Phe Ile Tyr
        115                 120                 125

Lys Val Lys Leu Arg Gly Thr Asn Phe Pro Ser Asp Gly Pro Val Met
    130                 135                 140

Gln Lys Lys Thr Met Gly Trp Glu Ala Ser Ser Glu Arg Met Tyr Pro
145                 150                 155                 160

Glu Asp Gly Ala Leu Lys Gly Glu Ile Lys Gln Arg Leu Lys Leu Lys
                165                 170                 175

Asp Gly Gly His Tyr Asp Ala Glu Val Lys Thr Thr Tyr Lys Ala Lys
            180                 185                 190

Lys Pro Val Gln Leu Pro Gly Ala Tyr Asn Val Asn Ile Lys Leu Asp
        195                 200                 205

Ile Thr Ser His Asn Glu Asp Tyr Thr Ile Val Glu Gln Tyr Glu Arg
    210                 215                 220

Ala Glu Gly Arg His Ser Thr Gly Gly Met Asp Glu Leu Tyr Arg Ser
225                 230                 235                 240

Gly Gly Gly His His His His His His Gly Asp Leu
                245                 250
```

<210> SEQ ID NO 17
<211> LENGTH: 1577
<212> TYPE: PRT
<213> ORGANISM: Clostridium Tetani

<400> SEQUENCE: 17

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95
```

-continued

```
Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510
```

-continued

```
Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
```

-continued

```
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                 1005

Gly Glu  Val Arg Gln Ile Thr  Phe Arg Asp Leu Pro  Asp Lys Phe
    1010                 1015                 1020

Asn Ala  Tyr Leu Ala Asn Lys  Trp Val Phe Ile Thr  Ile Thr Asn
    1025                 1030                 1035

Asp Arg  Leu Ser Ser Ala Asn  Leu Tyr Ile Asn Gly  Val Leu Met
    1040                 1045                 1050

Gly Ser  Ala Glu Ile Thr Gly  Leu Gly Ala Ile Arg  Glu Asp Asn
    1055                 1060                 1065

Asn Ile  Thr Leu Lys Leu Asp  Arg Cys Asn Asn Asn  Asn Gln Tyr
    1070                 1075                 1080

Val Ser  Ile Asp Lys Phe Arg  Ile Phe Cys Lys Ala  Leu Asn Pro
    1085                 1090                 1095

Lys Glu  Ile Glu Lys Leu Tyr  Thr Ser Tyr Leu Ser  Ile Thr Phe
    1100                 1105                 1110

Leu Arg  Asp Phe Trp Gly Asn  Pro Leu Arg Tyr Asp  Thr Glu Tyr
    1115                 1120                 1125

Tyr Leu  Ile Pro Val Ala Ser  Ser Ser Lys Asp Val  Gln Leu Lys
    1130                 1135                 1140

Asn Ile  Thr Asp Tyr Met Tyr  Leu Thr Asn Ala Pro  Ser Tyr Thr
    1145                 1150                 1155

Asn Gly  Lys Leu Asn Ile Tyr  Tyr Arg Arg Leu Tyr  Asn Gly Leu
    1160                 1165                 1170

Lys Phe  Ile Ile Lys Arg Tyr  Thr Pro Asn Asn Glu  Ile Asp Ser
    1175                 1180                 1185

Phe Val  Lys Ser Gly Asp Phe  Ile Lys Leu Tyr Val  Ser Tyr Asn
    1190                 1195                 1200

Asn Asn  Glu His Ile Val Gly  Tyr Pro Lys Asp Gly  Asn Ala Phe
    1205                 1210                 1215

Asn Asn  Leu Asp Arg Ile Leu  Arg Val Gly Tyr Asn  Ala Pro Gly
    1220                 1225                 1230

Ile Pro  Leu Tyr Lys Lys Met  Glu Ala Val Lys Leu  Arg Asp Leu
    1235                 1240                 1245

Lys Thr  Tyr Ser Val Gln Leu  Lys Leu Tyr Asp Asp  Lys Asn Ala
    1250                 1255                 1260

Ser Leu  Gly Leu Val Gly Thr  His Asn Gly Gln Ile  Gly Asn Asp
    1265                 1270                 1275

Pro Asn  Arg Asp Ile Leu Ile  Ala Ser Asn Trp Tyr  Phe Asn His
    1280                 1285                 1290

Leu Lys  Asp Lys Ile Leu Gly  Cys Asp Trp Tyr Phe  Val Pro Thr
    1295                 1300                 1305

Asp Glu  Gly Trp Thr Asn Asp  Gly Ser Ala Glu Asn  Leu Tyr Phe
    1310                 1315                 1320

Gln Ser  Gly Ser Gly Ser Asn  Gly Ser Ser Gly Ser  Val Ser Met
    1325                 1330                 1335
```

```
Ala Ile  Ile Lys Glu Phe Met  Arg Phe Lys Val His  Met Glu Gly
    1340                 1345                 1350

Ser Val  Asn Gly His Glu Phe  Glu Ile Glu Gly Glu  Gly Glu Gly
    1355                 1360                 1365

Arg Pro  Tyr Glu Gly Thr Gln  Thr Ala Lys Leu Lys  Val Thr Lys
    1370                 1375                 1380

Gly Gly  Pro Leu Pro Phe Ala  Trp Asp Ile Leu Ser  Pro Gln Phe
    1385                 1390                 1395

Met Tyr  Gly Ser Lys Ala Tyr  Val Lys His Pro Ala  Asp Ile Pro
    1400                 1405                 1410

Asp Tyr  Leu Lys Leu Ser Phe  Pro Glu Gly Phe Lys  Trp Glu Arg
    1415                 1420                 1425

Val Met  Asn Phe Glu Asp Gly  Gly Val Val Thr Val  Thr Gln Asp
    1430                 1435                 1440

Ser Ser  Leu Gln Asp Gly Glu  Phe Ile Tyr Lys Val  Lys Leu Arg
    1445                 1450                 1455

Gly Thr  Asn Phe Pro Ser Asp  Gly Pro Val Met Gln  Lys Lys Thr
    1460                 1465                 1470

Met Gly  Trp Glu Ala Ser Ser  Glu Arg Met Tyr Pro  Glu Asp Gly
    1475                 1480                 1485

Ala Leu  Lys Gly Glu Ile Lys  Gln Arg Leu Lys Leu  Lys Asp Gly
    1490                 1495                 1500

Gly His  Tyr Asp Ala Glu Val  Lys Thr Thr Tyr Lys  Ala Lys Lys
    1505                 1510                 1515

Pro Val  Gln Leu Pro Gly Ala  Tyr Asn Val Asn Ile  Lys Leu Asp
    1520                 1525                 1530

Ile Thr  Ser His Asn Glu Asp  Tyr Thr Ile Val Glu  Gln Tyr Glu
    1535                 1540                 1545

Arg Ala  Glu Gly Arg His Ser  Thr Gly Gly Met Asp  Glu Leu Tyr
    1550                 1555                 1560

Arg Ser  Gly Gly Gly His His  His His His His Gly  Asp Leu
    1565                 1570                 1575
```

<210> SEQ ID NO 18
<211> LENGTH: 72
<212> TYPE: DNA
<213> ORGANISM: Geobacillus Stearothermphilus

<400> SEQUENCE: 18

```
attctgcaaa atcctattgt ttatcatacc tgatataatg aaaagatacg acactaggag     60

tgaatggcca tg                                                         72
```

<210> SEQ ID NO 19
<211> LENGTH: 44
<212> TYPE: DNA
<213> ORGANISM: Bacteriophage T7

<400> SEQUENCE: 19

```
taatacgact cactataggg gaattgtgag cggataacaa ttcc                      44
```

<210> SEQ ID NO 20
<211> LENGTH: 43
<212> TYPE: DNA
<213> ORGANISM: bacteriophage t7

<400> SEQUENCE: 20

-continued

```
cctctagaaa taattttgtt taactttaag aaggagatat acc                    43


<210> SEQ ID NO 21
<211> LENGTH: 3947
<212> TYPE: DNA
<213> ORGANISM: Clostridium Tetani

<400> SEQUENCE: 21

atgccaataa ccataaataa ttttagatat agtgatcctg ttaataatga tacaattatt     60

atgatggagc caccatactg taagggtcta gatatctatt ataaggcttt caaaataaca    120

gatcgtattt ggatagtgcc ggaaaggtat gaatttggga caaaacctga agattttaac    180

ccaccatctt cattaataga aggtgcatct gagtattacg atccaaatta tttaaggact    240

gattctgata aagatagatt tttacaaacc atggtaaaac tgtttaacag aattaaaaac    300

aatgtagcag gtgaagcctt attagataag ataataaatg ccataccta ccttggaaat    360

tcatattcct tactagacaa gtttgataca aactctaatt cagtatcttt taatttatca    420

gaacaagacc ccagtggagc aactacaaaa tcagcaatgc tgacaaattt aataatattt    480

ggacctgggc ctgttttaaa taaaaatgag gttagaggta ttgtattgag ggtagataat    540

aaaaattact tcccatgtag agatggtttt ggttcaataa tgcaaatggc attttgccca    600

gaatatatac ccacttttga taatgtaata gaaaatatta cgtcactcac tattggcaaa    660

agcaaatatt ttcaagatcc agcattacta ttaatgcacg aacttataca tgtactacat    720

ggtttatacg gaatgcaggt atcaagccat gaaattattc catccaaaca agaaatttat    780

atgcagcata catatccaat aagtgctgaa gaactattca cttttggcgg acaggatgct    840

aatcttataa gtattgatat aaaaaacgat ttatatgaaa aaactttaaa tgattataaa    900

gctatagcta acaaacttag tcaagtcact agctgcaatg atcccaacat tgatattgat    960

agctacaaac aaatatatca acaaaaatat caattcgata aagatagcaa tggacaatat   1020

attgtaaatg aggataaatt tcagatacta tataatagca taatgtatgg ttttacagag   1080

attgaattgg gaaaaaaatt taatataaaa actagacttt cttattttag tatgaatcat   1140

gaccctgtaa aaattccaaa tttattagat gatacaattt acaatgatac agaaggattt   1200

aatatagaaa gcaaagatct gaaatctgaa tataaaggtc aaaatatgag ggtaaataca   1260

aatgctttta gaaatgttga tggatcaggc ctagtttcaa aacttattgg cttatgtaaa   1320

aaaattatac caccaacaaa tataagagaa aatttatata atagaactgc atcattaaca   1380

gatttaggag gagaattatg tataaaaatt aaaaatgaag atttaacttt tatagctgaa   1440

aaaaatagct tttcagaaga accatttcaa gatgaaacag ttagttataa tacaaaaaat   1500

aaaccattaa attttaatta ttcgctagat aaaattattt tagattataa tctacaaagt   1560

aaaattacat tacctaatga taggacaacc ccagttacaa aaggaattcc atatgctcca   1620

aaatataaaa gtaatgctgc aagtacaata gaaatacata atattgatga caatacaata   1680

tatcaatatt tgtatgctca aaaatctcct acaactctac aaagaataac tatgactaat   1740

tctgtcgatg acgcattaat aaattccacc aaaatatatt catattttcc atctgtaatc   1800

agtaaagtta accaaggtgc acaaggaatt ttattcttac agtgggtgag agatataatt   1860

gatgatttac caatgaatct tcacaaaaaa ctactattga taaaatttca gatgtatcca   1920

ctattgttcc ttatatagga cccgcattaa acattgtaaa acaaggctat gagggaaact   1980

ttataggtgc tttagaaact accggagtgg ttttattatt ggaatatatt ccagaaatta   2040

ctttaccagt aattgcagct ttatctatag cagaaagtag cacacaaaaa gaaaagataa   2100
```

```
taaaaacaat agataacttt ttagaaaaaa gatatgaaaa atggattgaa gtatataaac   2160
taataaaagc aaaatggtta ggcacagtta atacgcaatt ccaaaaaaga agttatcaaa   2220
tgtatagatc tttagaatat caagtagatg caataaaaaa aataatagac tatgaatata   2280
aaatatattc aggacctgat aaggaacaaa ttgccgacga aattaataat ctgaaaaaca   2340
aacttgaaga aaaggctaat aaagcaatga taaacataaa tatatttatg agggaaagtt   2400
ctagatcatt tttagttaat caaatgatta acgaagctaa aaagcagtta ttagagtttg   2460
atactcaaag caaaaatatt ttaatgcagt atataaaagc aaattctaaa tttataggta   2520
taactgaact aaaaaaatta gaatcaaaaa taaacaaagt tttttcaaca ccaattccat   2580
tttcttattc taaaaatctg gattgttggg ttgataatga agaagatata gatgttatat   2640
taaaaaagag tacaatttta aatttagata ttaataatga tattatatca gatatatctg   2700
ggtttaattc atctgtaata acatatccag atgctcaatt ggtgcccgga ataaatggca   2760
aagcaataca tttagtaaac aatgaatctt ctgaagttat agtgcataaa gctatggata   2820
ttgaatataa tgatatgttt aataatttta ccgttagctt ttggttgagg gttcctaaag   2880
tatctgctag tcatttagaa caatatggca caaatgagta ttcaataatt agctctatga   2940
aaaaatatag tctatcaata ggatctggtt ggagtgtatc acttaaaggt aataacttaa   3000
tatggacttt aaaagattcc gcgggagaag ttagacaaat aacttttagt gatttatctg   3060
ataaatttaa tgcttattta gcaaataaat gggtttttat aactattact aatgatagat   3120
tatcttctgc taatttgtat ataaatggag tacttatgaa aaatgcagaa attaccggtt   3180
taggagctat tagagaggat aataatataa cattaaaact agatagatgt aataataata   3240
atcaatacgt ttctattgat aaatttagga tattttgcaa agcattaaat ccaaaagaga   3300
ttgaaaaatt atacacaagt tatttatcta taaccttttt aagagacttc tggggaaacc   3360
ctttacgata tgatacagaa tattatttaa taccagtagc ttctagttct aaagatgttc   3420
aattgaaaaa tataacagat tatatgtatt tgacaaatgc gccatcgtat actaacggaa   3480
aattgaatat atattataga aggttatata gtggactaaa atttattata aaaagatata   3540
cacctaataa tgaaatagat tcttttgtta aatcaggtga ttttattaaa ttatatgtat   3600
catataacaa taatgagcac attgtaggtt atccgaaaga tggaaatgcc tttaataatc   3660
ttgatagaat tctaagagta ggttataatg ccccaggtat ccctctttat aaaaaaatgg   3720
aagcagtaaa attgcgtgat ttaaaaacct attctgtaca acttaaatta tatgatgata   3780
aaaatgcatc tttaggacta gtaggtatcc gtaatggtca aataggcaac gatccaaata   3840
gggatatatt aattgcaagc aactggtact ttaatcattt aaaagataaa actttaacat   3900
gtgattggta ctttgtacct acagatgaag gatggacaaa tgattaa                 3947
```

<210> SEQ ID NO 22
<211> LENGTH: 801
<212> TYPE: DNA
<213> ORGANISM: Artificial Sequence
<220> FEATURE:
<223> OTHER INFORMATION: TEVsite, mCherry, His6

<400> SEQUENCE: 22

```
gaaaacctgt acttccaatc caatattggt agtgggagca acggcagcag cggatccgtg     60
agcaagggcg aggaggataa catggccatc atcaaggagt tcatgcgctt caaggtgcac    120
atggagggct ccgtgaacgg ccacgagttc gagatcgagg gcgagggcga gggccgcccc    180
```

-continued

```
tacgagggca cccagaccgc caagctgaag gtgaccaagg gtggccccct gcccttcgcc    240

tgggacatcc tgtcccctca gttcatgtac ggctccaagg cctacgtgaa gcaccccgcc    300

gacatccccg actacttgaa gctgtccttc cccgagggct tcaagtggga gcgcgtgatg    360

aacttcgagg acggcggcgt ggtgaccgtg acccaggact cctccctcca ggacggcgag    420

ttcatctaca aggtgaagct gcgcggcacc aacttcccct ccgacggccc cgtaatgcag    480

aagaagacca tgggctggga ggcctcctcc gagcggatgt accccgagga cggcgccctg    540

aagggcgaga tcaagcagag gctgaagctg aaggacggcg gccactacga cgctgaggtc    600

aagaccacct acaaggccaa gaagcccgtg cagctgcccg gcgcctacaa cgtcaacatc    660

aagttggaca tcacctccca caacgaggac tacaccatcg tggaacagta cgaacgcgcc    720

gagggccgcc actccaccgg cggcatggac gagctgtaca agtaagcggc cgcactcgag    780

caccaccacc accaccactg a                                              801
```

<210> SEQ ID NO 23
<211> LENGTH: 137
<212> TYPE: PRT
<213> ORGANISM: Thermus thermophilus

<400> SEQUENCE: 23

```
Met Glu Arg Thr Phe Val Met Ile Lys Pro Asp Gly Val Arg Arg Gly
1               5                   10                  15

Leu Val Gly Glu Ile Leu Ala Arg Phe Glu Arg Lys Gly Phe Arg Ile
            20                  25                  30

Ala Ala Leu Lys Leu Met Gln Ile Ser Gln Glu Leu Ala Glu Arg His
        35                  40                  45

Tyr Ala Glu His Arg Glu Lys Pro Phe Phe Pro Gly Leu Val Arg Phe
    50                  55                  60

Ile Thr Ser Gly Pro Val Val Ala Met Val Leu Glu Gly Pro Gly Val
65                  70                  75                  80

Val Ala Glu Val Arg Lys Met Met Gly Ala Thr His Pro Lys Asp Ala
                85                  90                  95

Leu Pro Gly Thr Ile Arg Gly Asp Phe Ala Thr Thr Ile Asp Glu Asn
            100                 105                 110

Val Ile His Gly Ser Ala Thr Leu Glu Asp Ala Gln Arg Glu Ile Ala
        115                 120                 125

Leu Phe Phe Arg Pro Glu Glu Leu Leu
    130                 135
```

<210> SEQ ID NO 24
<211> LENGTH: 9
<212> TYPE: PRT
<213> ORGANISM: Artificial Sequence
<220> FEATURE:
<223> OTHER INFORMATION: RNAP Supplement

<400> SEQUENCE: 24

```
Gly Ser Ala His His His His His His
1               5
```

<210> SEQ ID NO 25
<211> LENGTH: 33
<212> TYPE: PRT

-continued

```
<213> ORGANISM: Thermus aquaticus

<400> SEQUENCE: 25

Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
            20                  25                  30

Thr
```